US007087714B2

(12) United States Patent
Pasternak et al.

(10) Patent No.: US 7,087,714 B2
(45) Date of Patent: Aug. 8, 2006

(54) MU-OPIOD RECEPTOR SPLICE VARIANT POLYPEPTIDES

(75) Inventors: Gavril W. Pasternak, New York, NY (US); Ying-Xian Pan, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 580 days.

(21) Appl. No.: 10/185,083

(22) Filed: Jun. 28, 2002

(65) Prior Publication Data

US 2003/0050467 A1 Mar. 13, 2003

Related U.S. Application Data

(60) Provisional application No. 60/302,072, filed on Jun. 29, 2001.

(51) Int. Cl.

*C07K 1/00* (2006.01)
*C07K 14/00* (2006.01)
*C07K 17/00* (2006.01)
*G01N 33/53* (2006.01)
*G01N 33/567* (2006.01)

(52) U.S. Cl. ........................ 530/350; 435/7.1; 435/7.2

(58) Field of Classification Search ................ 530/350, 530/402; 435/7.1, 7.2

See application file for complete search history.

(56) References Cited

U.S. PATENT DOCUMENTS 4,946,778 A 8/1990 Ladner et al.
6,103,492 A 8/2000 Yu

OTHER PUBLICATIONS

Abbadie et al. (1999) "Neurons in the dorsal column white matter of the spinal cord: complex neuropilin an unexpected location" Proc. Natl. Acad. Sci. USA 96:260-265.

Bare et al. (1994) "Expression of two variants of the human μ opioid receptor mRNA in SK-N-SH cells and human brain" FEBS Lett. 354:213-6.

Chen et al. (1993)"Molecular cloning and functional expression of a μ-opioid receptor from rat brain" Mol. Pharmacol. 44:8-12.

Cole et al. (1985) "Monoclonal Antibodies and Cancer Therapy" Alan R. Liss, Inc., pp. 77-96.

Cote et al. (1983) "Generation of human monoclonal antibodies reactive with cellular antigens" Proc. Natl. Acad. Sci. USA 80:2026-2030.

Delfs et al. (1994) "Expression of μ opioid receptor mRNA in rat brain: an in situ hybridization study at the single cell level"0 J. Comp. Neurol. 345:46-68.

Elliott et al. (1994) "The NMDA receptor antagonists, LY274614 and MK-801, and the nitric oxide synthase inhibitor, NG-nitro-L-arginine, attenuate analgesic tolerance to the μ-opioid morphine but not to κ opioids" Pain 56:69-75.

Evans et al. (1981) "Establishment in culture of pluripotential cells from mouse embryos" Nature 292:154-6.

Giros et al. (1995) "Chromosomal localization of opioid peptide and receptor genes in the mouse" Life Sci. 56:369-375.

Guiramand et al. (1995) "Alternative splicing of the dopamine D2 receptor directs specificity of coupling to G-proteins" J. Biol. Chem. 270:7354-58.

Huse et al. (1999) "Generation of a large combinatorial library of the immunoglobulin repertoire in phage lambda" Science 246:1275-81.

Kolesnikov et al. (1994) "1-Aminocyclopropane carboxylic acid (ACPC) prevents μ and δ opioid tolerance" Life Sci. 55:1393-98.

Kolesnikov et al. (1993) "Blockade of tolerance to morphine but not to κ opioids by a nitric oxide synthase inhibitor" Proc. Natl. Acad. Sci. USA 90:5162-5166.

Liang et al. (1995) "Cloning and characterization of the promoter region of the mouse μ opioid receptor gene" Brain Res. 679:82-88.

Lowry et al. (1951) "Protein measurement with the folin phenol reagent" J. Biol. Chem. 193:265-75.

Lucas et al. (1995) "New players in the 5-HT receptor field: genes and knockouts" TiPS 16:246-252.

Lutz et al. (1992) "Opioid receptors and their pharmacological profiles" J. Receptor Res. 12:267-286.

Min et al. (1994) "Genomic Structure analysis of promoter sequence of a mouse μ opioid receptor gene" Proc. Natl. Acad. Sci. USA 91:9081-85.

Morrison et al. (1984) "Chimeric human antibody molecules: mouse antigen-binding domains with human constant region domains" Proc. Natl. Acad. Sci. USA 81:6851-55.

Neuberger et al. (1984) "Recombinant antibodies possessing novel effector functions" Nature 312:604-8.

Olson et al. (1989) "Endogenous opiates: 1988" Peptides 10:1253-1280.

Pan et al. (1994) "Cloning, Expression and Classification of a $\kappa_3$—Related opioid receptor using Antisense Oligodeoxynucleotides" Regul. Pept. 54:217-218.

(Continued)

*Primary Examiner*—Robert S. Landsman
(74) *Attorney, Agent, or Firm*—Edwards & Angell LLP; Amy M. Leahy

(57) ABSTRACT

The present invention encompasses novel splice variant forms of the mu-opioid receptor-1 (MOR-1) and the polynucleotide sequences encoding the MOR-1 splice variants. The invention further encompasses methods of screening for compositions regulating the MOR-1 splice variant activities and the development of therapeutic modalities directed to regulating activity. Regulation of the MOR-1 splice variant activities may impact the physiologic process of analgesia.

8 Claims, 38 Drawing Sheets

OTHER PUBLICATIONS

Pan et al. (1996) “Dissociation of affinity and efficacy in KOR-3 chimeras” FEBS Lett. 395:207-10.
Pasternak (1993) “Pharmacological mechanisms of opioid analgesics” Clin. Neuropharmacol. 16:1-18.
Pasternak et al. (1995) “Mapping of opioid receptors using antisense oligodeoxynucleotides: correlating their molecular biology and pharmacology” TiPS 16:344-50.
Reisine et al. (1993) “Molecular Biology of opioid receptors” Trends Neurosci. 16:506-510.
Reisine et al. (1996) “Opioid analgesics and antagonists” in Goodman & Gilman’s “The pharmacological basis of therapeutics” 9th Ed. (Harman et al. eds) McGraw-Hill pp. 521-555.
Robertson (1991) “Using embryonic stem cells to introduce mutations into the mouse germ line” Biol. Reprod. 44:238-245.
Rossi et al. (1997) “Antisense mapping of MOR-1 in rats: distinguishing between morphine and morphine-6β-glucuronide antinociception” J. Pharmacol. Exp. Ther. 281:109-114.
Rossi et al. (1996) “Naloxone sensitive orphanin FQ-induced analgesia in mice”Eur. J. Pharmacol. 311:R7-8.
Rossi et al. (1995) “Antisense mapping the MOR-1 opioid receptor: evidence for alternative splicing and a novel morphine-6β-glucuronide receptor” FEBS Lett. 369:192-196.
Sibinga et al. (1988) “Opioid peptides and opioid receptors in cells of the immune system” Annu. Rev. Immunol. 6:219-49.
Simon (1991) “Opioid receptors and endogenous opioid peptides” Medicinal Res. Rev. 11:357-374.
Standifer et al. (1997) “G proteins and opioid receptor-mediated signaling” Cell. Signal. 9:237-248.
Standifer et al. (1996) “Differential blockade of opioid analgesia by antisense oligodeoxy-nucleotides directed against various G protein α subunits” Mol. Pharmacol. 50:293-298.
Takeda et al. (1985) “Construction of chimaeric processed immunoglobulin genes containing mouse variable and human constant region sequences” Nature 314:452-4.
Trujillo et al. (1991) “Inhibition of morphine tolerance and dependence by the NMDA receptor antagonist MK-801” Science 251:85-87.
van den Engh et al. (1992) “Estimating genomic distance from DNA sequence location in cell nuclei by a random walk model” Science 257:1410-1412.
Vanetti et al. (1992) “Cloning and expression of a novel mouse somatostatin receptor (SSTR2B)” FEBS Lett. 311:290-294.
Wang et al. (1993) “μopiate receptor: cDNA cloning and expression” Proc. Natl. Acad. Sci. USA 90:10230-34.
Wolozin et al. (1981) “Classification of multiple morphine and enkephalin binding sites in the central nervous system” Proc. Natl. Acad. Sci. USA 78:6181-84.
Yasuda et al. (1993) “Cloning and functional comparison of κ and δ opioid receptors from mouse brain” Proc. Natl. Acad. Sci. USA 90:6736-6740.
Zimprich et al. (1995) “Cloning and expression of an isoform of the rat μ opioid receptor (rMOR1B ) which differs in agonist induced desensitization from rMOR1” FEBS Lett. 359:142-146.
Du et al. (1996) “Identification of a novel splice variant of the mouse mu opioid receptor” Soc. Neurosci. Ab 22:695.5.
Du et al. (1997) “A splice variant of the mu opioid receptor is present in human SHSY-5Y cells” Soc. Neurosci. Ab. 23:479.3.
Leventhal et al. (1997) “Antisense mapping of the MOR-1 opioid receptor clone: modulation of hyperphagia induced by DAMGO” J. Pharmacol. Exp. Ther. 282:1402-1407.
Leventhal et al. (1996) “Antisense oligodeoxynucleotides against the MOR-1 clone alter weight and ingestive responses in rats” Brain Res. 719:78-84.
Kaufman, D., et al. J. Biol. Chem 270:15877-15883 (1995).
Rossi et al. (1996) Neurosci. Lett. 216:1-4.
Rossi et al. (1994) Life Sci. 54:375-379.
Pan, Y.-X. GenBank Acession #U26915, Submitted May 11, 1995, FEBS Lett. 369 (2-3), 192-196 (1995).
Pan, Ying-Xian, et al., “Identification and characterization of two new human mu opioid receptor splice variants, hMOR-1O and hMOR-1X”, *Science Direct*, Biochemical and Biophysical Research Communications 301 (2003) 1057-1061.

Fig. 3

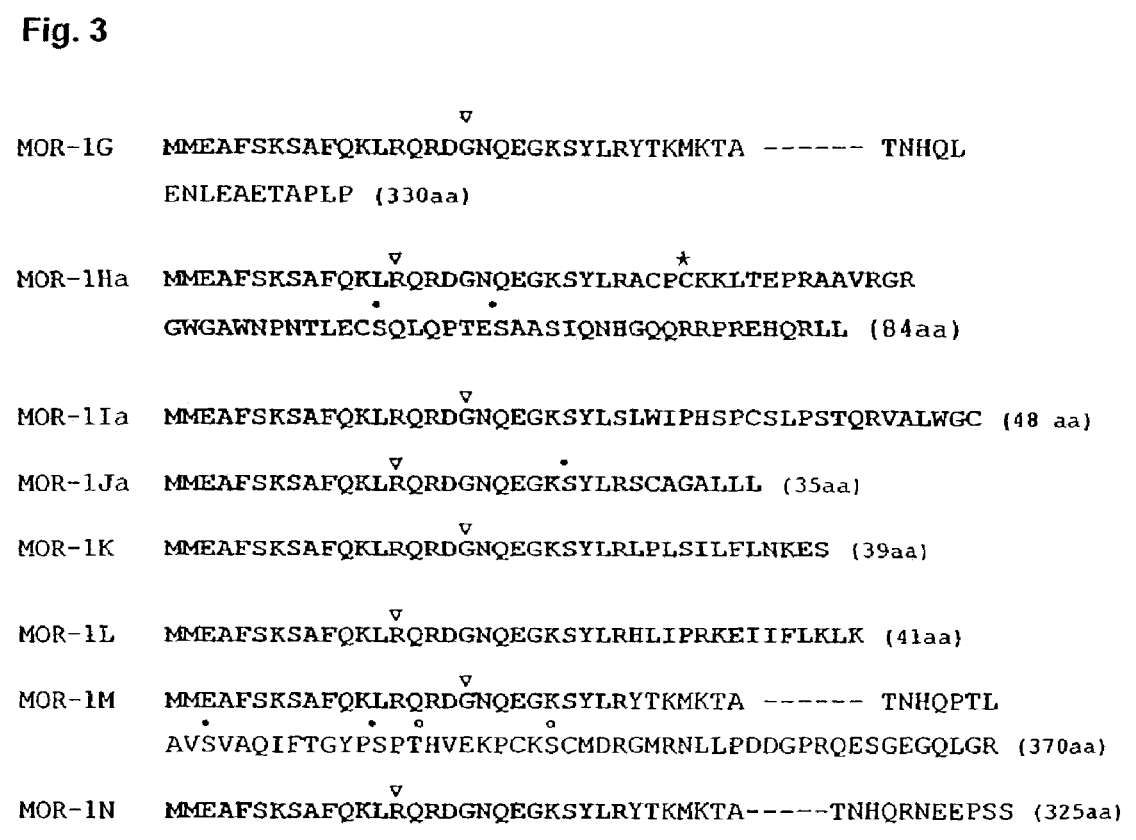

MOR-1G MMEAFSKSAFQKLRQRDGNQEGKSYLRYTKMKTA ------ TNHQL ENLEAETAPLP (330aa)

MOR-1Ha MMEAFSKSAFQKLRQRDGNQEGKSYLRACPCKKLTEPRAAVRGR GWGAWNPNTLECSQLQPTESAASIQNHGQQRRPREHQRLL (84aa)

MOR-1Ia MMEAFSKSAFQKLRQRDGNQEGKSYLSLWIPHSPCSLPSTQRVALWGC (48 aa)

MOR-1Ja MMEAFSKSAFQKLRQRDGNQEGKSYLRSCAGALLL (35aa)

MOR-1K MMEAFSKSAFQKLRQRDGNQEGKSYLRLPLSILFLNKES (39aa)

MOR-1L MMEAFSKSAFQKLRQRDGNQEGKSYLRHLIPRKEIIFLKLK (41aa)

MOR-1M MMEAFSKSAFQKLRQRDGNQEGKSYLRYTKMKTA ------ TNHQPTL AVSVAQIFTGYPSPTHVEKPCKSCMDRGMRNLLPDDGPRQESGEGQLGR (370aa)

MOR-1N MMEAFSKSAFQKLRQRDGNQEGKSYLRYTKMKTA-----TNHQRNEEPSS (325aa)

Fig. 4

Exon 11

TTTACTGTCCTTGAGAATGGAGAGGATCAGCAAAGCTGGGAAGCCCTCCAGGCTCATTTCAGAGA
GAATATTCCACAGAGCTTGAAGGCGCGGGATCTGGGCCGATGATGGAAGCTTTCTCTAAGTCTGC
ATTCCAAAAGCTCAGACAGAGAGATGGAAATCAAGAGGGGAAGAGTTACCTCAGgttggtttctc
ttcagactgtagtga------

Exon 12

--------aaaatgaaatattgagaggtcagtctcttgcagGTCTTGTGCAGGTGCACTGCTGCT
GTGAATTCATGAAGACAACACCCTCCCCTTTAGAAGACAGTGCTTCACAACACTCCCAACTAGCC
TCTGGCTCTGATGTTCACTTTGTCCCCTCTTCTGAAGCAGgtatttattacagatgtc-------

Exon 1

Exon 1b

--------tccttctctctcctccctccctctagCCTCTGGATCCCTCACAGCCCATGCTCCCTC
CCTTCCACTCAGAGAGTGGCGCTTTGGGGATGCTAAGGATGCGCCTCCGTGTACTTCTAAGGTGG
GAGGGGGATACAAGCAGAGGAGAATATCGGACGCTCAGACGTTCCATTCTGCCTGCCGCTCTTCT Exon 1a CTGGTTCCACTAGGGCTTGTCCTTGTAAGAAACTGACGGAGCCTAGGGCAGCTGTGAGAGGAAGA
GGCTGGGGCGCCTGGAACCCGAACACTCTTGAGTGCTCTCAGTTACAGCCTACCGAGTCCGCAGC
AAGCATTCAGAACCATG------

Exon 13

-------- agtaaacactaatcaaattttatttcacagACACCTCATTCCAAGGAAGGAAAT
TATCTTTTTAAAACTGAAATAACTAGGCATTCCAAGCAATGGCGGTGAGCTGATAAAGACT
GAGAGTGTAATGAGTCAGAAAATTGTGTTGGGTTCCCCTCTTGAGTGTGACTAATGTCAAA
AGgtatgcctttgaatcactggtctatctttgc Exon 14

--------gattggggatatattcttcatgctttcagGCTCCCTCTGTCCATTCTTTTCCTGAA
CAAAGAGTCATGACAACTCAAAGAATCAACTGAAAATCAAAATAGAAAATGGGCTAAGGCAACTG
GTCGACCACCACAAAGgtagttcattctctcaagcctcttttaccctt-------

Fig. 6

| Clone | Predicted Peptide Products | | | |
|---|---|---|---|---|
| | Amino Acids | MW (kDal) | Predicted TM Domains | Comments |
| MOR-1G | 330 | 38.0 | 6 | Amino terminus contains the 27 amino acids encoded by exon 11 followed by a sequence identical to the MOR-1 protein coded by exon 2 to end |
| MOR-1H | 84 | 9.6 | 0 | Amino terminus contains the 27 amino acids encoded by exon 11, but the remainder are unique |
| | 398 | 44.4 | 7 | Identical to the MOR-1 protein |
| MOR-1I | 48 | 5.5 | 0 | Amino terminus contains the 27 amino acids encoded by exon 11, but the remainder are unique |
| | 398 | 44.4 | 7 | Identical to the MOR-1 protein |
| MOR-1J | 35 | 3.9 | 0 | Amino terminus contains the 27 amino acids encoded by exon 11, but the remainder are unique |
| | 398 | 44.4 | 7 | Identical to the MOR-1 protein |
| MOR-1K | 39 | 4.6 | 0 | Amino terminus contains the 27 amino acids encoded by exon 11, but the remainder are unique |
| MOR-1L | 41 | 4.9 | 0 | Amino terminus contains the 27 amino acids encoded by exon 11, but the remainder are unique |
| MOR-1M | 370 | 42.3 | 6 | Amino terminus contains the 27 amino acids encoded by exon 11 followed by a sequence identical to the MOR-1C protein coded by exon 2 to end |
| MOR-1N | 325 | 37.5 | 6 | Amino terminus contains the 27 amino acids encoded by exon 11 followed by a sequence identical to the MOR-1D protein coded by exon 2 to end |

| Antisense Target | Suprapinal Analgesia | | Spinal Analgesia | |
|---|---|---|---|---|
| | Morphine | M6G | Morphine | M6G |
| Exon 11a | Inactive | Active | Active | Inactive |
| Exon 11b | Inactive | Active | Active | Inactive |
| Mismatch (exon11) | Inactive | Inactive | Inactive | Inactive |
| Exon 1 | Active | Inactive | Inactive | Inactive |
| Exon 2 | Inactive | Active | Inactive | Inactive |
| Exon 3 | Inactive | Active | Inactive | Active |
| Exon 4 | Active | Inactive | Active | Inactive |
| Exon 6 | Active | Inactive | | |
| Exon 7 | Active | Inactive | | |
| Exon 8 | Active | Inactive | | |
| Exon 9 | Active | Inactive | | |
| Exon 10 | Active | Inactive | | |

Figure 13

MOR-1ha ggcgcgggat ctgggccgat gatggaagct ttctctaagt ctgcattcca aaagctcaga 60
cagagagatg gaaatcaaga ggggaagagt tacctcaggg cttgtccttg taagaaactg 120
acggagccta gggcagctgt gagaggaaga ggctggggcg cctggaaccc gaacactctt 180
gagtgctctc agttacagcc taccgagtcc gcagcaagca ttcagaacca tggacagcag 240
cgccggccca gggaacatca gcgactgctc tgaccccta gctcctgcaa gttgctcccc 300
agcacctggc tcctggctca acttgtccca cgttgatggc aaccagtccg acccatgcgg 360
tcctaaccgc acggggcttg gcgggagcca cagcctgtgc cctcagaccg gcagcccttc 420
catggtcaca gccatcacca tcatggccct ctattctatc gtgtgtgtag tgggcctctt 480
tggaaacttc ctggtcatgt atgtgattgt aagatatacc aaaatgaaga ctgccaccaa 540
catctacatt ttcaaccttg ctctggcaga tgccttagcc actagcacgc tgccctttca 600
gagtgttaac tacctgatgg gaacgtggcc ctttggaaac atcctctgca agatcgtgat 660
ctcaatagac tactacaaca tgttcaccag tatcttcacc ctctgcacca tgagtgtaga 720
ccgctacatt gccgtctgcc acccggtcaa ggccctggat ttccgtaccc cccgaaatgc 780
caaaattgtc aatgtctgca actggatcct ctcttctgcc attggtctgc ccgtaatgtt 840
catggcaacc acaaaataca ggcaggggtc catagattgc accctcacgt tctctcatcc 900
cacatggtac tgggagaacc tgctcaaaat ctgtgtcttc atcttcgcct tcatcatgcc 960
ggtcctcatc atcactgtgt gttatggact gatgatctta cgactcaaga gtgtccgcat 1020
gctgtcgggc tccaaagaaa aggacaggaa cctgcgcagg atcacccgga tggtgctggt 1080
ggtcgtggct gtatttattg tctgctggac cccatccac atctatgtca tcatcaaagc 1140
actgatcacg attccagaaa ccactttcca gactgtttcc tggcacttct gcattgcctt 1200
gggttacaca aacagctgcc tgaacccagt tctttatgcg ttcctggatg aaaacttcaa 1260
acgatgtttt agagagttct gcatcccaac ttcctccaca atcgaacagc aaaactctgc 1320
tcgaatccgt caaaacacta gggaacaccc ctccacggct aatacagtgg atcgaactaa 1380
ccaccagcta gaaaatctgg aagcagaaac tgctccattg ccctaactgg gtcccacgcc 1440

Figure 14
MOR-1ia (SEQ ID NO 16)

ggcgcgggat ctgggccgat gatggaagct ttctctaagt ctgcattcca aaagctcaga
60
cagagagatg gaaatcaaga ggggaagagt tacctcagcc tctggatccc tcacagccca
120
tgctccctcc cttccactca gagagtggcg ctttggggat gctaaggatg cgcctccgtg
180
tacttctaag gtgggagggg gatacaagca gaggagaata tcggacgctc agacgttcca
240
ttctgcctgc cgctcttctc tggttccact agggcttgtc cttgtaagaa actgacggag
300
cctagggcag ctgtgagagg aagaggctgg ggcgcctgga acccgaacac tcttgagtgc
360
tctcagttac agcctaccga gtccgcagca agcattcaga accatggaca gcagcgccgg
420
cccagggaac atcagcgact gctctgaccc cttagctcct gcaagttgct ccccagcacc
480
tggctcctgg ctcaacttgt cccacgttga tggcaaccag tccgacccat gcggtcctaa
540
ccgcacgggg cttggcggga gccacagcct gtgccctcag accggcagcc cttccatggt
600
cacagccatc accatcatgg ccctctattc tatcgtgtgt gtagtgggcc tctttggaaa
660
cttcctggtc atgtatgtga ttgtaagata taccaaaatg aagactgcca ccaacatcta
720
cattttcaac cttgctctgg cagatgcctt agccactagc acgctgccct ttcagagtgt
780
taactacctg atgggaacgt ggccctttgg aaacatcctc tgcaagatcg tgatctcaat
840
agactactac aacatgttca ccagtatctt caccctctgc accatgagtg tagaccgcta
900
cattgccgtc tgccacccgg tcaaggccct ggatttccgt accccccgaa atgccaaaat
960
tgtcaatgtc tgcaactgga tcctctcttc tgccattggt ctgcccgtaa tgttcatggc
1020
aaccacaaaa tacaggcagg ggtccataga ttgcaccctc acgttctctc atcccacatg
1080
gtactgggag aacctgctca aaatctgtgt cttcatcttc gccttcatca tgccggtcct
1140
catcatcact gtgtgttatg gactgatgat cttacgactc aagagtgtcc gcatgctgtc
1200
gggctccaaa gaaaaggaca ggaacctgcg caggatcacc cggatggtgc tggtggtcgt
1260
ggctgtattt attgtctgct ggacccccat ccacatctat gtcatcatca aagcactgat
1320
cacgattcca gaaaccactt tccagactgt ttcctggcac ttctgcattg ccttgggtta
1380
cacaaacagc tgcctgaacc cagttcttta tgcgttcctg gatgaaaact tcaaacgatg
1440
ttttagagag ttctgcatcc caacttcctc cacaatcgaa cagcaaaact ctgctcgaat
1500
ccgtcaaaac actagggaac acccctccac ggctaataca gtggatcgaa ctaaccacca
1560
gctagaaaat ctggaagcag aaactgctcc attgccctaa ctgggtccca cgcc
1614

Figure 15

MOR-1ja (SEQ ID NO 17)

ggcgcgggat ctgggccgat gatggaagct ttctctaagt ctgcattcca aaagctcaga
60
cagagagatg gaaatcaaga ggggaagagt tacctcaggt cttgtgcagg tgcactgctg
120
ctgtgaattc atgaagacaa caccctcccc tttagaagac agtgcttcac aacactccca
180
actagcctct ggctctgatg ttcactttgt cccctcttct gaagcagggc ttgtccttgt
240
aagaaactga cggagcctag ggcagctgtg agaggaagag gctggggcgc ctggaacccg
300
aacactcttg agtgctctca gttacagcct accgagtccg cagcaagcat tcagaaccat
360
ggacagcagc gccggcccag ggaacatcag cgactgctct gaccccttag ctcctgcaag
420
ttgctcccca gcacctggct cctggctcaa cttgtcccac gttgatggca accagtccga
480
cccatgcggt cctaaccgca cggggcttgg cgggagccac agcctgtgcc ctcagaccgg
540
cagcccttcc atggtcacag ccatcaccat catggccctc tattctatcg tgtgtgtagt
600
gggcctcttt ggaaacttcc tggtcatgta tgtgattgta agatatacca aaatgaagac
660
tgccaccaac atctacattt tcaaccttgc tctggcagat gccttagcca ctagcacgct
720
gcccttteag agtgttaact acctgatggg aacgtggccc tttggaaaca tcctctgcaa
780
gatcgtgatc tcaatagact actacaacat gttcaccagt atcttcaccc tctgcaccat
840
gagtgtagac cgctacattg ccgtctgcca cccggtcaag gccctggatt tccgtacccc
900
ccgaaatgcc aaaattgtca atgtctgcaa ctggatcctc tcttctgcca ttggtctgcc
960
cgtaatgttc atggcaacca caaaatacag gcaggggtcc atagattgca ccctcacgtt
1020
ctctcatccc acatggtact gggagaacct gctcaaaatc tgtgtcttca tcttcgcctt
1080
catcatgccg gtcctcatca tcactgtgtg ttatggactg atgatcttac gactcaagag
1140
tgtccgcatg ctgtcgggct ccaaagaaaa ggacaggaac ctgcgcagga tcacccggat
1200
ggtgctggtg gtcgtggctg tatttattgt ctgctggacc cccatccaca tctatgtcat
1260
catcaaagca ctgatcacga ttccagaaac cactttccag actgtttcct ggcacttctg
1320
cattgccttg ggttacacaa acagctgcct gaacccagtt ctttatgcgt tcctggatga
1380
aaacttcaaa cgatgtttta gagagttctg catcccaact tcctccacaa tcgaacagca
1440
aaactctgct cgaatccgtc aaaacactag ggaacacccc tccacggcta atacagtgga
1500
tcgaactaac caccagctag aaaatctgga agcagaaact gctccattgc cctaactggg
1560
tcccacgcc
1569

Figure 16

MOR-1k ggcgcgggat ctgggccgat gatggaagct ttctctaagt ctgcattcca aaagctcaga 60
cagagagatg gaaatcaaga ggggaagagt tacctcaggc tccctctgtc cattcttttc 120
ctgaacaaag agtcatgaca actcaaagaa tcaactgaaa atcaaaatag aaaatgggct 180
aaggcaactg gtcgaccacc acaaagatat accaaaatga agactgccac caacatctac 240
attttcaacc ttgctctggc agatgcctta gccactagca cgctgccctt tcagagtgtt 300
aactacctga tgggaacgtg gccctttgga aacatcctct gcaagatcgt gatctcaata 360
gactactaca acatgttcac cagtatcttc accctctgca ccatgagtgt agaccgctac 420
attgccgtct gccacccggt caaggccctg gatttccgta ccccccgaaa tgccaaaatt 480
gtcaatgtct gcaactggat cctctcttct gccattggtc tgcccgtaat gttcatggca 540
accacaaaat acaggcaggg gtccatagat tgcaccctca cgttctctca tcccacatgg 600
tactgggaga acctgctcaa aatctgtgtc ttcatcttcg ccttcatcat gccggtcctc 660
atcatcactg tgtgttatgg actgatgatc ttacgactca agagtgtccg catgctgtcg 720
ggctccaaag aaaaggacag gaacctgcgc aggatcaccc ggatggtgct ggtggtcgtg 780
gctgtattta ttgtctgctg gacccccatc cacatctatg tcatcatcaa agcactgatc 840
acgattccag aaaccacttt ccagactgtt tcctggcact tctgcattgc cttgggttac 900
acaaacagct gcctgaaccc agttctttat gcgttcctgg atgaaaactt caaacgatgt 960
tttagagagt tctgcatccc aacttcctcc acaatcgaac agcaaaactc tgctcgaatc 1020
cgtcaaaaca ctagggaaca cccctccacg gctaatacag tggatcgaac taaccaccag 1080
ctagaaaatc tggaagcaga aactgctcca ttgccctaac tgggtcccac gcc 1133

Figure 17

MOR-1l ggcgcgggat ctgggccgat gatggaagct ttctctaagt ctgcattcca aaagctcaga 60
cagagagatg gaaatcaaga ggggaagagt tacctcagac acctcattcc aaggaaggaa 120
attatctttt taaaactgaa ataactaggc attccaagca cctggcggtg agctgataaa 180
gactgagagt gtaatgagtc agaaaattgt gttgggttcc cctcttgagt gtgactaatg 240
tcaaaagata taccaaaatg aagactgcca ccaacatcta cattttcaac cttgctctgg 300
cagatgcctt agccactagc acgctgccct ttcagagtgt taactacctg atgggaacgt 360
ggccctttgg aaacatcctc tgcaagatcg tgatctcaat agactactac aacatgttca 420
ccagtatctt caccctctgc accatgagtg tagaccgcta cattgccgtc tgccaccccgg
480
tcaaggccct ggatttccgt acccccccgaa atgccaaaat tgtcaatgtc tgcaactgga
540
tcctctcttc tgccattggt ctgcccgtaa tgttcatggc aaccacaaaa tacaggcagg
600
ggtccataga ttgcaccctc acgttctctc atcccacatg gtactgggag aacctgctca
660
aaatctgtgt cttcatcttc gccttcatca tgccggtcct catcatcact gtgtgttatg
720
gactgatgat cttacgactc aagagtgtcc gcatgctgtc gggctccaaa gaaaaggaca
780
ggaacctgcg caggatcacc cggatggtgc tggtggtcgt ggctgtattt attgtctgct
840
ggacccccat ccacatctat gtcatcatca aagcactgat cacgattcca gaaaccactt
900
tccagactgt ttcctggcac ttctgcattg ccttgggtta cacaaacagc tgcctgaacc
960
cagttcttta tgcgttcctg gatgaaaact tcaaacgatg ttttagagag ttctgcatcc
1020
caacttcctc cacaatcgaa cagcaaaact ctgctcgaat ccgtcaaaac actagggaac
1080
acccctccac ggctaataca gtggatcgaa ctaaccacca gctagaaaat ctggaagcag
1140
aaactgctcc attgccctaa ctgggtccca cgcc
1174

Figure 18

MOR-1n ggcgcgggat ctgggccgat gatggaagct ttctctaagt ctgcattcca aaagctcaga
60
cagagagatg gaaatcaaga ggggaagagt tacctcagat ataccaaaat gaagactgcc
120
accaacatct acattttcaa ccttgctctg gcagatgcct tagccactag cacgctgccc
180
tttcagagtg ttaactacct gatgggaacg tggccctttg gaaacatcct ctgcaagatc
240
gtgatctcaa tagactacta caacatgttc accagtatct tcaccctctg caccatgagt
300
gtagaccgct acattgccgt ctgccacccg gtcaaggccc tggatttccg taccccccga
360
aatgccaaaa ttgtcaatgt ctgcaactgg atcctctctt ctgccattgg tctgcccgta
420
atgttcatgg caaccacaaa atacaggcag gggtccatag attgcaccct cacgttctct
480
catcccacat ggtactggga gaacctgctc aaaatctgtg tcttcatctt cgccttcatc
540
atgccggtcc tcatcatcac tgtgtgttat ggactgatga tcttacgact caagagtgtc
600
cgcatgctgt cgggctccaa agaaaaggac aggaacctgc gcaggatcac ccggatggtg
660
ctggtggtcg tggctgtatt tattgtctgc tggaccccca tccacatcta tgtcatcatc
720
aaagcactga tcacgattcc agaaaccact ttccagactg tttcctggca cttctgcatt
780
gccttgggtt acacaaacag ctgcctgaac ccagttcttt atgcgttcct ggatgaaaac
840
ttcaaacgat gttttagaga gttctgcatc ccaacttcct ccacaatcga acagcaaaac
900 tctgctcgaa tccgtcaaaa cactagggaa cacccctcca cggctaatac agtggatcga
960
actaaccacc agaggaatga ggaaccttct tcctgatgat ggcccaagac aggaatccgg
1020
ggaaggccag cttggcaggt gaatgtcatc cgaacacagg gatgagctgg tgagcagtgt
1080
gg
1082

Figure 19

MOR-1bV ggaacccgaa cactcttgag tgctctcagt tacagcctac cgagtccgca gcaagcattc
60
agaaccatgg acagcagcgc cggcccaggg aacatcagcg actgctctga cccccttagct
120
cctgcaagtt gctccccagc acctggctcc tggctcaact tgtcccacgt tgatggcaac
180
cagtccgacc catgcggtcc taaccgcacg gggcttggcg ggagccacag cctgtgccct
240
cagaccggca gcccttccat ggtcacagcc atcaccatca tggccctcta ttctatcgtg
300
tgtgtagtgg gcctctttgg aaacttcctg gtcatgtatg tgattgtaag atataccaaa
360
atgaagactg ccaccaacat ctacattttc aaccttgctc tggcagatgc cttagccact
420
agcacgctgc cctttcagag tgttaactac ctgatgggaa cgtggccctt tggaaacatc
480
ctctgcaaga tcgtgatctc aatagactac tacaacatgt tcaccagtat cttcaccctc
540
tgcaccatga gtgtagaccg ctacattgcc gtctgccacc cggtcaaggc cctggatttc
600
cgtacccccc gaaatgccaa aattgtcaat gtctgcaact ggatcctctc ttctgccatt
660
ggtctgcccg taatgttcat ggcaaccaca aaatacaggc aggggtccat agattgcacc
720
ctcacgttct ctcatcccac atggtactgg gagaacctgc tcaaaatctg tgtcttcatc
780
ttcgccttca tcatgccggt cctcatcatc actgtgtgtt atggactgat gatcttacga
840
ctcaagagtg tccgcatgct gtcgggctcc aaagaaaagg acaggaacct gcgcaggatc
900
acccggatgg tgctggtggt cgtggctgta tttattgtct gctggacccc catccacatc
960
tatgtcatca tcaaagcact gatcacgatt ccagaaacca ctttccagac tgtttcctgg
1020
cacttctgca ttgccttggg ttacacaaac agctgcctga acccagttct ttatgcgttc
1080
ctggatgaaa acttcaaacg atgttttaga gagttctgca tcccaacttc ctccacaatc
1140
gaacagcaaa actctgctcg aatccgtcaa aacactaggg aacacccctc cacggctaat
1200
acagtggatc gaactaacca ccagtgtgta tgagtgctat gcccacaggg accagaagat
1260
ggtatcagac cttctagaac tgaagtagtg agcagtcccc acccccaccc ccccgcaatg
1320
tgagtagctt ataaaatgat tttatgtact tgttagctct ccatggagca caagataaaa
1380
gtgacatcac agtttgaaat aatagctctt tgatcctaga atgaaagcat ggaaaaaata
1440 agttgggtca tttgtctata ggaaggaagg ggacaaggtg gggacagaga ggactgagaa
1500
gacgtagaca attaaggtag gaagaaggct aatctagata gcacatttac gttccaaatc
1560
cactacttct tcttgtgtgt ctttcaggca caccaaaaac ctcaagaatg cctgaaatgc
1620
agatgtctat cccttaccat cctggttata tgcctacatt tccaacatca gcaattcttc
1680
ataatgatca aaaaaaatgt ttcataacta aaggaaaaac catctgcttc ttttgattta
1740
atgaaactta aatatctctg ggtgtggggg acattaggat gttaaagttt cttcaaagga
1800
aagagataac ttctcatagt gctgaaatgg gtaccctcaa gataggggac aggcaaacag
1860
agtttatgga agatgatatt aagaaagaaa aacatatcaa tcaagaaaaa tagtgttacg
1920
tattttgaca acaaagccta attgataact tacagaaatt aatatatgta gaatgggata
1980
agacttctgt gcattgatga taaatctgct gcttagcccc tgttacaatg tacagctaag
2040
tacgtctttc ttgtctttct ttctgtgctt tcttcacttt gatttaggct aaaatgtcag
2100
ttattcaaag gcccctaata ttgccaaatc cagtctcatt ccagatcctg tagaattaat
2160
attagtttga gttgctcttt cagagaaaat gacatgcagc ccgaatcatt attcacaaag
2220
aaaaagggcc aatccaaggt gaagtgttgc taacactgga aaggtctgaa caaggcctac
2280
tttcctaaca ataacaacgc ctcaagagat cttcaggatg aaatacaact cgaaaaatat
2340
aaattataaa gccctggacg taaatcacaa ggagtaagag gagtctctga catattgggt
2400
aagatagagc cccaagatta atgggaaaga ttctagcaaa cgaacaacca caaactatca
2460
agctgtgtaa acttgtccca gaacctgggt cacagtgaga ggagcaggtg gctctgagaa
2520
gcaagactgc atctggcaaa attgcaaaga aagaaattag ctactagatg gcacaattgg
2580
atgaactcga gaacccagtg gtttatgtag atttgaaaac ctctatcaat ctctgtaacc
2640
atacactgtg tttagttctg atctaaattt aatgatgcta tgacttagct ttataaaatt
2700
ttatctcatt gtattcttag gagcctcagt cagcagagac atgatgtgaa tgaacggact
2760
gattagacaa ggtttcctga acactgaaat acaaaacaaa tagagagctt actagagaaa
2820
attcgtagcc cgaaaattca attatagaaa caaatgagtg ttagagtaga tatggtaagg
2880
cctcagagag gttttatttc atgactaaca acatgaccca aggcacctaa tccatggtga
2940
ttagattaca a
2951

Figure 20
MOR-1bIII
ggaacccgaa cactcttgag tgctctcagt tacagcctac cgagtccgca gcaagcattc
60
agaaccatgg acagcagcgc cggcccaggg aacatcagcg actgctctga ccccttagct
120 cctgcaagtt gctccccagc acctggctcc tggctcaact tgtcccacgt tgatggcaac
180
cagtccgacc catgcggtcc taaccgcacg gggcttggcg ggagccacag cctgtgccct
240
cagaccggca gcccttccat ggtcacagcc atcaccatca tggccctcta ttctatcgtg
300
tgtgtagtgg gcctctttgg aaacttcctg gtcatgtatg tgattgtaag atataccaaa
360
atgaagactg ccaccaacat ctacattttc aaccttgctc tggcagatgc cttagccact
420
agcacgctgc cctttcagag tgttaactac ctgatgggaa cgtggccctt tggaaacatc
480
ctctgcaaga tcgtgatctc aatagactac tacaacatgt tcaccagtat cttcaccctc
540
tgcaccatga gtgtagaccg ctacattgcc gtctgccacc cggtcaaggc cctggatttc
600
cgtacccccc gaaatgccaa aattgtcaat gtctgcaact ggatcctctc ttctgccatt
660
ggtctgcccg taatgttcat ggcaaccaca aaatacaggc aggggtccat agattgcacc
720
ctcacgttct ctcatcccac atggtactgg gagaacctgc tcaaaatctg tgtcttcatc
780
ttcgccttca tcatgccggt cctcatcatc actgtgtgtt atggactgat gatcttacga
840
ctcaagagtg tccgcatgct gtcgggctcc aaagaaaagg acaggaacct gcgcaggatc
900
acccggatgg tgctggtggt cgtggctgta tttattgtct gctggacccc catccacatc
960
tatgtcatca tcaaagcact gatcacgatt ccagaaacca ctttccagac tgtttcctgg
1020
cacttctgca ttgccttggg ttacacaaac agctgcctga acccagttct ttatgcgttc
1080
ctggatgaaa acttcaaacg atgttttaga gagttctgca tcccaacttc ctccacaatc
1140
gaacagcaaa actctgctcg aatccgtcaa aacactaggg aacacccctc cacggctaat
1200
acagtggatc gaactaacca ccagacaagc ctcacacttc agtaatggaa tgagtagatt
1260
aaatcggcga gcaagatggt gggaggagtc aaaatatttt catgccttcc tgtggaactc
1320
caaaggaaga cc
1332

Figure 21

MOR-1bIV ggaacccgaa cactcttgag tgctctcagt tacagcctac cgagtccgca gcaagcattc
60
agaaccatgg acagcagcgc cggcccaggg aacatcagcg actgctctga cccccttagct
120
cctgcaagtt gctccccagc acctggctcc tggctcaact tgtcccacgt tgatggcaac
180
cagtccgacc catgcggtcc taaccgcacg gggcttggcg ggagccacag cctgtgccct
240
cagaccggca gcccttccat ggtcacagcc atcaccatca tggccctcta ttctatcgtg
300
tgtgtagtgg gcctctttgg aaacttcctg gtcatgtatg tgattgtaag atataccaaa
360
atgaagactg ccaccaacat ctacattttc aaccttgctc tggcagatgc cttagccact
420 agcacgctgc cctttcagag tgttaactac ctgatgggaa cgtggccctt tggaaacatc
480
ctctgcaaga tcgtgatctc aatagactac tacaacatgt tcaccagtat cttcaccctc
540
tgcaccatga gtgtagaccg ctacattgcc gtctgccacc cggtcaaggc cctggatttc
600
cgtacccccc gaaatgccaa aattgtcaat gtctgcaact ggatcctctc ttctgccatt
660
ggtctgcccg taatgttcat ggcaaccaca aaatacaggc aggggtccat agattgcacc
720
ctcacgttct ctcatcccac atggtactgg gagaacctgc tcaaaatctg tgtcttcatc
780
ttcgccttca tcatgccggt cctcatcatc actgtgtgtt atggactgat gatcttacga
840
ctcaagagtg tccgcatgct gtcgggctcc aaagaaaagg acaggaacct gcgcaggatc
900
acccggatgg tgctggtggt cgtggctgta tttattgtct gctggacccc catccacatc
960
tatgtcatca tcaaagcact gatcacgatt ccagaaacca ctttccagac tgtttcctgg
1020
cacttctgca ttgccttggg ttacacaaac agctgcctga acccagttct ttatgcgttc
1080
ctggatgaaa acttcaaacg atgttttaga gagttctgca tcccaacttc ctccacaatc
1140
gaacagcaaa actctgctcg aatccgtcaa aacactaggg aacacccctc cacggctaat
1200
acagtggatc gaactaacca ccaggcacac caaaaacctc aagaatgcct gaaatgcaga
1260
tgtctatccc ttaccatcct ggttatatgc ctacatttcc aacatcagca attcttcata
1320
atgatcaaaa aaaatgtttc ataactaaag gaaaaaccat ctgcttcttt tgatttaatg
1380
aaacttaaat atctctgggt gtgggggaca ttaggatgtt aaagtttctt caaaggaaag
1440
agataacttc tcatagtgct gaaatgggta ccctcaagat aggggacagg caaacagagt
1500
ttatggaaga tgatattaag aaagaaaaac atatcaatca agaaaaatag tgttacgtat
1560
tttgacaaca aagcctaatt gataacttac agaaattaat atatgtagaa tgggataaga
1620
cttctgtgca ttgatgataa atctgctgct tagcccctgt tacaatgtac agctaagtac
1680
gtctttcttg tctttctttc tgtgctttct tcactttgat ttaggctaaa atgtcagtta
1740
ttcaaaggcc cctaatattg ccaaatccag tctcattcca gatcctgtag aattaatatt
1800
agtttgagtt gctctttcag agaaaatgac atgcagcccg aatcattatt cacaaagaaa
1860
aagggccaat ccaaggtgaa gtgttgctaa cactggaaag gtctgaacaa ggcctacttt
1920
cctaacaata acaacgcctc aagagatctt caggatgaaa tacaactcga aaaatataaa
1980
ttataaagcc ctggacgtaa atcacaagga gtaagaggag tctctgacat attgggtaag
2040
atagagcccc aagattaatg ggaaagattc tagcaaacga acaaccacaa actatcaagc
2100
tgtgtaaact tgtcccagaa cctgggtcac agtgagagga gcaggtggct ctgagaagca
2160 agactgcatc tggcaaaatt gcaaagaaag aaattagcta ctagatggca caattggatg
2220
aactcgagaa cccagtggtt tatgtagatt tgaaaacctc tatcaatctc tgtaaccata
2280
cactgtgttt agttctgatc taaatttaat gatgctatga cttagcttta taaaatttta
2340
tctcattgta ttcttaggag cctcagtcag cagagacatg atgtgaatga acggactgat
2400
tagacaaggt ttcctgaaca ctgaaataca aaacaaatag agagcttact agagaaaatt
2460
cgtagcccga aaattcaatt atagaaacaa atgagtgtta gagtagatat ggtaaggcct
2520
cagagaggtt ttatttcatg actaacaaca tgacccaagg cacctaatcc atggtgatta
2580
gattacaa
2588

Figure 22

MOR-1o ggaacccgaa cactcttgag tgctctcagt tacagcctac cgagtccgca gcaagcattc
60
agaaccatgg acagcagcgc cggcccaggg aacatcagcg actgctctga cccccttagct
120
cctgcaagtt gctccccagc acctggctcc tggctcaact tgtcccacgt tgatggcaac
180
cagtccgacc catgcggtcc taaccgcacg gggcttggcg ggagccacag cctgtgccct
240
cagaccggca gcccttccat ggtcacagcc atcaccatca tggccctcta ttctatcgtg
300
tgtgtagtgg gcctctttgg aaacttcctg gtcatgtatg tgattgtaag atataccaaa
360
atgaagactg ccaccaacat ctacattttc aaccttgctc tggcagatgc cttagccact
420
agcacgctgc cctttcagag tgttaactac ctgatgggaa cgtggccctt tggaaacatc
480
ctctgcaaga tcgtgatctc aatagactac tacaacatgt tcaccagtat cttcaccctc
540
tgcaccatga gtgtagaccg ctacattgcc gtctgccacc cggtcaaggc cctggatttc
600
cgtacccccc gaaatgccaa aattgtcaat gtctgcaact ggatcctctc ttctgccatt
660
ggtctgcccg taatgttcat ggcaaccaca aaatacaggc aggggtccat agattgcacc
720
ctcacgttct ctcatcccac atggtactgg gagaacctgc tcaaaatctg tgtcttcatc
780
ttcgccttca tcatgccggt cctcatcatc actgtgtgtt atggactgat gatcttacga
840
ctcaagagtg tccgcatgct gtcgggctcc aaagaaaagg acaggaacct gcgcaggatc
900
acccggatgg tgctggtggt cgtggctgta tttattgtct gctggacccc catccacatc
960
tatgtcatca tcaaagcact gatcacgatt ccagaaacca ctttccagac tgtttcctgg
1020
cacttctgca ttgccttggg ttacacaaac agctgcctga acccagttct ttatgcgttc
1080
ctggatgaaa acttcaaacg atgttttaga gagttctgca tcccaacttc ctccacaatc
1140
gaacagcaaa actctgctcg aatccgtcaa aacactaggg aacacccctc cacggctaat
1200 acagtggatc gaactaacca ccagataatg aaatttgaag ctatctaccc taaactgagc 1260
ttcaaatctt gggcattgaa atattttact ttcattagag aaaagaaaag gaacacaaaa 1320
gctggggctc ttcctcccct ccctacgtgt catgctggat ctccctccca ggctcacagg 1380
ggcgtggctg cttggttgct tcctctaaga cacatggggc cttcttatcc ttcctgaccc 1440
acctgacctt cctctaatgg aagcagagcc ccaagctctc tattccagca catccctgtt 1500
ttaaacatag ctgcccttca gattctctaa cgctgccttc gactcccttc cacacccagt 1560
gtttgcatgt cagtgtggat cttgcacagc cagagagtag aagggaagat aattggagaa 1620
gctctgtcct aagtaactaa aaggtttgct ttaaaaatac atccaattag cacttatcat 1680
tatcactgcc tctgc 1695

Figure 23 hMOR-1o cggtgctcct ggctacctcg cacagcgtgc ccgcccggcc gtcagtacca tggacagcag 60
cgctgccccc acgaacgcca gcaattgcac tgatgccttg gcgtactcaa gttgctcccc 120
agcacccagc cccggttcct gggtcaactt gtcccactta gatggcaacc tgtccgaccc 180
atgcggtccg aaccgcaccg acctgggcgg gagagacagc ctgtgccctc cgaccggcag 240
tccctccatg atcacggcca tcacgatcat ggccctctac tccatcgtgt gcgtggtggg 300
gctcttcgga aacttcctgg tcatgtatgt gattgtcaga tacaccaaga tgaagactgc 360
caccaacatc tacattttca accttgctct ggcagatgcc ttagccacca gtaccctgcc 420
cttccagagt gtgaattacc taatgggaac atggccattt ggaaccatcc tttgcaagat 480
agtgatctcc atagattact ataacatgtt caccagcata ttcaccctct gcaccatgag 540
tgttgatcga tacattgcag tctgccaccc tgtcaaggcc ttagatttcc gtactccccg 600
aaatgccaaa attatcaatg tctgcaactg gatcctctct tcagccattg gtcttcctgt 660
aatgttcatg gctacaacaa aatacaggca aggttccata gattgtacac taacattctc 720
tcatccaacc tggtactggg aaaacctgct gaagatctgt gttttcatct tcgccttcat 780
tatgccagtg ctcatcatta ccgtgtgcta tggactgatg atcttgcgcc tcaagagtgt 840
ccgcatgctc tctggctcca aagaaaagga caggaatctt cgaaggatca ccaggatggt 900
gctggtggtg gtggctgtgt tcatcgtctg ctggactccc attcacattt acgtcatcat 960
taaagccttg gttacaatcc cagaaactac gttccagact gtttcttggc acttctgcat 1020
tgctctaggt tacacaaaca gctgcctcaa cccagtcctt tatgcatttc tggatgaaaa 1080
cttcaaacga tgcttcagag agttctgtat cccaacctct tccaacattg agcaacaaaa 1140
ctccactcga attcgtcaga acactagaga ccacccctcc acggccaata cagtggatag
1200
aactaatcat cagtgcctac ctataccttc cctgtcttgc tgggctctag agcatggctg
1260
cttggttgtg taccctggac cactgcaagg acctcttgtc agatatgacc tcccagctat
1320
ccttcactcg tcctgccttc gtggaaatac tgctcccagc ccgtctggtg ggcatttct
1380
cttgagttaa gcatgattat tcttcagttg cccgacactg cccttgactc ccttccaaat
1440
tcggcatttt cacatcagta tggc
1464

Figure 24
hMOR-1p
cggtgctcct ggctacctcg cacagcgtgc ccgcccggcc gtcagtacca tggacagcag
60
cgctgccccc acgaacgcca gcaattgcac tgatgccttg gcgtactcaa gttgctcccc
120
agcacccagc cccggttcct gggtcaactt gtcccactta gatggcaacc tgtccgaccc
180
atgcggtccg aaccgcaccg acctgggcgg gagagacagc ctgtgccctc cgaccggcag
240
tccctccatg atcacggcca tcacgatcat ggccctctac tccatcgtgt gcgtggtggg
300
gctcttcgga aacttcctgg tcatgtatgt gattgtcaga tacaccaaga tgaagactgc
360
caccaacatc tacattttca accttgctct ggcagatgcc ttagccacca gtaccctgcc
420
cttccagagt gtgaattacc taatgggaac atggccattt ggaaccatcc tttgcaagat
480
agtgatctcc atagattact ataacatgtt caccagcata ttcaccctct gcaccatgag
540
tgttgatcga tacattgcag tctgccaccc tgtcaaggcc ttagatttcc gtactccccg
600
aaatgccaaa attatcaatg tctgcaactg gatcctctct tcagccattg gtcttcctgt
660
aatgttcatg gctacaacaa aatacaggca aggttccata gattgtacac taacattctc
720
tcatccaacc tggtactggg aaaacctgct gaagatctgt gttttcatct tcgccttcat
780
tatgccagtg ctcatcatta ccgtgtgcta tggactgatg atcttgcgcc tcaagagtgt
840
ccgcatgctc tctggctcca aagaaaagga caggaatctt cgaaggatca ccaggatggt
900
gctggtggtg gtggctgtgt tcatcgtctg ctggactccc attcacattt acgtcatcat
960
taaagccttg gttacaatcc cagaaactac gttccagact gtttcttggc acttctgcat
1020
tgctctaggt tacacaaaca gctgcctcaa cccagtcctt tatgcatttc tggatgaaaa
1080
cttcaaacga tgcttcagag agttctgtat cccaacctct tccaacattg agcaacaaaa
1140
ctccactcga attcgtcaga acactagaga ccacccctcc acggccaata cagtggatag
1200
aactaatcat cagccaccct tggcagtcag catggcccag atctttacac gatatcctcc
1260
tccgactcat cgtgagaaaa cctgcaatga ttacatgaag aggtagataa tgtattaccc
1320

Figure 25
MOR-1m (SEQ ID NO 27)

```
ttttactgtc cttgagaatg gagaggatca gcaaagctgg gaagccctcc aggctcattt
1
cagagagaat attccacaga gcttgaaggc gcgggatctg ggccgatgat ggaagctttc
61
tctaagtctg cattccaaaa gctcagacag agagatggaa atcaagaggg gaagagttac
121
ctcagatata ccaaaatgaa gactgccacc aacatctaca ttttcaacct tgctctggca
181
gatgccttag ccactagcac gctgcccttt cagagtgtta actacctgat gggaacgtgg
241
ccctttggaa acatcctctg caagatcgtg atctcaatag actactacaa catgttcacc
301
agtatcttca ccctctgcac catgagtgta gaccgctaca ttgccgtctg ccacccggtc
361
aaggccctgg atttccgtac cccccgaaat gccaaaattg tcaatgtctg caactggatc
421
ctctcttctg ccattggtct gcccgtaatg ttcatggcaa ccacaaaata caggcagggg
481
tccatagatt gcaccctcac gttctctcat cccacatggt actgggagaa cctgctcaaa
541
atctgtgtct tcatcttcgc cttcatcatg ccggtcctca tcatcactgt gtgttatgga
601
ctgatgatct tacgactcaa gagtgtccgc atgctgtcgg gctccaaaga aaaggacagg
661
aacctgcgca ggatcacccg gatggtgctg gtggtcgtgg ctgtatttat tgtctgctgg
721
acccccatcc acatctatgt catcatcaaa gcactgatca cgattccaga aaccactttc
781
cagactgttt cctggcactt ctgcattgcc ttgggttaca caaacagctg cctgaaccca
841
gttctttatg cgttcctgga tgaaaacttc aaacgatgtt ttagagagtt ctgcatccca
901
acttcctcca caatcgaaca gcaaaactct gctcgaatcc gtcaaaacac tagggaacac
961
ccctccacgg ctaatacagt ggatcgaact aaccaccagc caaccctggc agtcagcgtg
1021
gcccagatct ttacaggata tccttctccg actcatgttg aaaaaccctg caagagttgc
1081
atggacagag gaatgaggaa ccttcttcct gatgatggcc caagacagga atccggggaa
1141
ggccagcttg gcaggtgaat gtcatccgaa cacagggatg agctggtgag cagtgtgg
1201
```

Figure 26

```
MOR-1Ha (SEQ ID NO 28)
Met Met Glu Ala Phe Ser Lys Ser Ala Phe Gln Lys Leu Arg Gln Arg
1               5                   10                  15
Asp Gly Asn Gln Glu Gly Lys Ser Tyr Leu Arg Ala Cys Pro Cys Lys
            20                  25                  30
Lys Leu Thr Glu Pro Arg Ala Ala Val Arg Gly Arg Gly Trp Gly Ala
        35                  40                  45
Trp Asn Pro Asn Thr Leu Glu Cys Ser Gln Leu Gln Pro Thr Glu Ser
    50                  55                  60
Ala Ala Ser Ile Gln Asn His Gly Gln Gln Arg Arg Pro Arg Glu His
65                  70                  75                  80
Gln Arg Leu Leu
```

Figure 27

```
MOR-1Ia (SEQ ID NO 29)
Met Met Glu Ala Phe Ser Lys Ser Ala Phe Gln Lys Leu Arg Gln Arg
1               5                   10                  15
Asp Gly Asn Gln Glu Gly Lys Ser Tyr Leu Ser Leu Trp Ile Pro His
            20                  25                  30
Ser Pro Cys Ser Leu Pro Ser Thr Gln Arg Val Ala Leu Trp Gly Cys
        35                  40                  45
```

Figure 28

```
MOR-1Ja (SEQ ID NO 30)
Met Met Glu Ala Phe Ser Lys Ser Ala Phe Gln Lys Leu Arg Gln Arg
1               5                   10                  15
Asp Gly Asn Gln Glu Gly Lys Ser Tyr Leu Arg Ser Cys Ala Gly Ala
            20                  25                  30
Leu Leu Leu
        35
```

Figure 29

```
MOR-1L (SEQ ID NO 31)
Met Met Glu Ala Phe Ser Lys Ser Ala Phe Gln Lys Leu Arg Gln Arg
1               5                   10                  15
Asp Gly Asn Gln Glu Gly Lys Ser Tyr Leu Arg Leu Pro Leu Ser Ile
            20                  25                  30
Leu Phe Leu Asn Lys Glu Ser
        35
```

Figure 30

MOR-1K

Met Met Glu Ala Phe Ser Lys Ser Ala Phe Gln Lys Leu Arg Gln Arg
1 5 10 15
Asp Gly Asn Gln Glu Gly Lys Ser Tyr Leu Arg His Leu Ile Pro Arg
20 25 30
Lys Glu Ile Ile Phe Leu Lys Leu Lys
35 40

Figure 31

MOR-1M

Met Met Glu Ala Phe Ser Lys Ser Ala Phe Gln Lys Leu Arg Gln Arg
1
Asp Gly Asn Gln Glu Gly Lys Ser Tyr Leu Arg Tyr Thr Lys Met Lys
17
Thr Ala Thr Asn Ile Tyr Ile Phe Asn Leu Ala Leu Ala Asp Ala Leu
33
Ala Thr Ser Thr Leu Pro Phe Gln Ser Val Asn Tyr Leu Met Gly Thr
49
Trp Pro Phe Gly Asn Ile Leu Cys Lys Ile Val Ile Ser Ile Asp Tyr
65
Tyr Asn Met Phe Thr Ser Ile Phe Thr Leu Cys Thr Met Ser Val Asp
81
Arg Tyr Ile Ala Val Cys His Pro Val Lys Ala Leu Asp Phe Arg Thr
97
Pro Arg Asn Ala Lys Ile Val Asn Val Cys Asn Trp Ile Leu Ser Ser
113
Ala Ile Gly Leu Pro Val Met Phe Met Ala Thr Thr Lys Tyr Arg Gln
139
Gly Ser Ile Asp Cys Thr Leu Thr Phe Ser His Pro Thr Trp Tyr Trp
145
Glu Asn Leu Leu Lys Ile Cys Val Phe Ile Phe Ala Phe Ile Met Pro
161
Val Leu Ile Ile Thr Val Cys Tyr Gly Leu Met Ile Leu Arg Leu Lys
177
Ser Val Arg Met Leu Ser Gly Ser Lys Glu Lys Asp Arg Asn Leu Arg
193
Arg Ile Thr Arg Met Val Leu Val Val Val Ala Val Phe Ile Val Cys
209
Trp Thr Pro Ile His Ile Tyr Val Ile Ile Lys Ala Leu Ile Thr Ile
225
Pro Glu Thr Thr Phe Gln Thr Val Ser Trp His Phe Cys Ile Ala Leu
241
Gly Tyr Thr Asn Ser Cys Leu Asn Pro Val Leu Tyr Ala Phe Leu Asp
257
Glu Asn Phe Lys Arg Cys Phe Arg Glu Phe Cys Ile Pro Thr Ser Ser
273
Thr Ile Glu Gln Gln Asn Ser Ala Arg Ile Arg Gln Asn Thr Arg Glu
289
His Pro Ser Thr Ala Asn Thr Val Asp Arg Thr Asn His Gln Pro Thr
305
Leu Ala Val Ser Val Ala Gln Ile Phe Thr Gly Tyr Pro Ser Pro Thr
321
His Val Glu Lys Pro Cys Lys Ser Cys Met Asp Arg Gly Met Arg Asn
337
Leu Leu Pro Asp Asp Gly Pro Arg Gln Glu Ser Gly Glu Gly Gln Leu
353
Gly Arg
369

Figure 32

MOR-1N

```
Met Met Glu Ala Phe Ser Lys Ser Ala Phe Gln Lys Leu Arg Gln Arg
1               5                   10                  15
Asp Gly Asn Gln Glu Gly Lys Ser Tyr Leu Arg Tyr Thr Lys Met Lys
            20                  25                  30
Thr Ala Thr Asn Ile Tyr Ile Phe Asn Leu Ala Leu Ala Asp Ala Leu
        35                  40                  45
Ala Thr Ser Thr Leu Pro Phe Gln Ser Val Asn Tyr Leu Met Gly Thr
    50                  55                  60
Trp Pro Phe Gly Asn Ile Leu Cys Lys Ile Val Ile Ser Ile Asp Tyr
65                  70                  75                  80
Tyr Asn Met Phe Thr Ser Ile Phe Thr Leu Cys Thr Met Ser Val Asp
                85                  90                  95
Arg Tyr Ile Ala Val Cys His Pro Val Lys Ala Leu Asp Phe Arg Thr
            100                 105                 110
Pro Arg Asn Ala Lys Ile Val Asn Val Cys Asn Trp Ile Leu Ser Ser
        115                 120                 125
Ala Ile Gly Leu Pro Val Met Phe Met Ala Thr Thr Lys Tyr Arg Gln
    130                 135                 140
Gly Ser Ile Asp Cys Thr Leu Thr Phe Ser His Pro Thr Trp Tyr Trp
145                 150                 155                 160
Glu Asn Leu Leu Lys Ile Cys Val Phe Ile Phe Ala Phe Ile Met Pro
                165                 170                 175
Val Leu Ile Ile Thr Val Cys Tyr Gly Leu Met Ile Leu Arg Leu Lys
            180                 185                 190
Ser Val Arg Met Leu Ser Gly Ser Lys Glu Lys Asp Arg Asn Leu Arg
        195                 200                 205
Arg Ile Thr Arg Met Val Leu Val Val Val Ala Val Phe Ile Val Cys
    210                 215                 220
Trp Thr Pro Ile His Ile Tyr Val Ile Ile Lys Ala Leu Ile Thr Ile
225                 230                 235                 240
Pro Glu Thr Thr Phe Gln Thr Val Ser Trp His Phe Cys Ile Ala Leu
                245                 250                 255
Gly Tyr Thr Asn Ser Cys Leu Asn Pro Val Leu Tyr Ala Phe Leu Asp
            260                 265                 270
Glu Asn Phe Lys Arg Cys Phe Arg Glu Phe Cys Ile Pro Thr Ser Ser
        275                 280                 285
Thr Ile Glu Gln Gln Asn Ser Ala Arg Ile Arg Gln Asn Thr Arg Glu
    290                 295                 300
His Pro Ser Thr Ala Asn Thr Val Asp Arg Thr Asn His Gln Arg Asn
305                 310                 315                 320
Glu Glu Pro Ser Ser
                325
```

Figure 33

MOR-1BV

```
Met Asp Ser Ser Ala Gly Pro Gly Asn Ile Ser Asp Cys Ser Asp Pro
1               5                   10                  15
Leu Ala Pro Ala Ser Cys Ser Pro Ala Pro Gly Ser Trp Leu Asn Leu
            20                  25                  30
Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60
Met Val Thr Ala Ile Thr Ile Met Ala Leu Tyr Ser Ile Val Cys Val
65                  70                  75                  80
```

```
Val Gly Leu Phe Gly Asn Phe Leu Val Met Tyr Val Ile Val Arg Tyr
                85                  90                  95
Thr Lys Met Lys Thr Ala Thr Asn Ile Tyr Ile Phe Asn Leu Ala Leu
            100                 105                 110
Ala Asp Ala Leu Ala Thr Ser Thr Leu Pro Phe Gln Ser Val Asn Tyr
        115                 120                 125
Leu Met Gly Thr Trp Pro Phe Gly Asn Ile Leu Cys Lys Ile Val Ile
    130                 135                 140
Ser Ile Asp Tyr Tyr Asn Met Phe Thr Ser Ile Phe Thr Leu Cys Thr
145                 150                 155                 160
Met Ser Val Asp Arg Tyr Ile Ala Val Cys His Pro Val Lys Ala Leu
                165                 170                 175
Asp Phe Arg Thr Pro Arg Asn Ala Lys Ile Val Asn Val Cys Asn Trp
            180                 185                 190
Ile Leu Ser Ser Ala Ile Gly Leu Pro Val Met Phe Met Ala Thr Thr
        195                 200                 205
Lys Tyr Arg Gln Gly Ser Ile Asp Cys Thr Leu Thr Phe Ser His Pro
    210                 215                 220
Thr Trp Tyr Trp Glu Asn Leu Leu Lys Ile Cys Val Phe Ile Phe Ala
225                 230                 235                 240
Phe Ile Met Pro Val Leu Ile Ile Thr Val Cys Tyr Gly Leu Met Ile
                245                 250                 255
Leu Arg Leu Lys Ser Val Arg Met Leu Ser Gly Ser Lys Glu Lys Asp
            260                 265                 270
Arg Asn Leu Arg Arg Ile Thr Arg Met Val Leu Val Val Val Ala Val
        275                 280                 285
Phe Ile Val Cys Trp Thr Pro Ile His Ile Tyr Val Ile Ile Lys Ala
    290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
            340                 345                 350
Pro Thr Ser Ser Thr Ile Glu Gln Gln Asn Ser Ala Arg Ile Arg Gln
        355                 360                 365
Asn Thr Arg Glu His Pro Ser Thr Ala Asn Thr Val Asp Arg Thr Asn
    370                 375                 380
His Gln Cys Val
385
```

Figure 34

MOR-1BIII

```
Met Asp Ser Ser Ala Gly Pro Gly Asn Ile Ser Asp Cys Ser Asp Pro
1               5                   10                  15
Leu Ala Pro Ala Ser Cys Ser Pro Ala Pro Gly Ser Trp Leu Asn Leu
            20                  25                  30
Ser His Val Asp Gly Asn Gln Ser Asp Pro Cys Gly Pro Asn Arg Thr
        35                  40                  45
Gly Leu Gly Gly Ser His Ser Leu Cys Pro Gln Thr Gly Ser Pro Ser
    50                  55                  60
Met Val Thr Ala Ile Thr Ile Met Ala Leu Tyr Ser Ile Val Cys Val
65                  70                  75                  80
Val Gly Leu Phe Gly Asn Phe Leu Val Met Tyr Val Ile Val Arg Tyr
                85                  90                  95
Thr Lys Met Lys Thr Ala Thr Asn Ile Tyr Ile Phe Asn Leu Ala Leu
            100                 105                 110
Ala Asp Ala Leu Ala Thr Ser Thr Leu Pro Phe Gln Ser Val Asn Tyr
        115                 120                 125
```

Leu Met Gly Thr Trp Pro Phe Gly Asn Ile Leu Cys Lys Ile Val Ile
130 135 140
Ser Ile Asp Tyr Tyr Asn Met Phe Thr Ser Ile Phe Thr Leu Cys Thr
145 150 155 160
Met Ser Val Asp Arg Tyr Ile Ala Val Cys His Pro Val Lys Ala Leu
165 170 175
Asp Phe Arg Thr Pro Arg Asn Ala Lys Ile Val Asn Val Cys Asn Trp
180 185 190
Ile Leu Ser Ser Ala Ile Gly Leu Pro Val Met Phe Met Ala Thr Thr
195 200 205
Lys Tyr Arg Gln Gly Ser Ile Asp Cys Thr Leu Thr Phe Ser His Pro
210 215 220
Thr Trp Tyr Trp Glu Asn Leu Leu Lys Ile Cys Val Phe Ile Phe Ala
225 230 235 240
Phe Ile Met Pro Val Leu Ile Ile Thr Val Cys Tyr Gly Leu Met Ile
245 250 255
Leu Arg Leu Lys Ser Val Arg Met Leu Ser Gly Ser Lys Glu Lys Asp
260 265 270
Arg Asn Leu Arg Arg Ile Thr Arg Met Val Leu Val Val Val Ala Val
275 280 285
Phe Ile Val Cys Trp Thr Pro Ile His Ile Tyr Val Ile Ile Lys Ala
290 295 300
Leu Ile Thr Ile Pro Glu Thr Thr Phe Gln Thr Val Ser Trp His Phe
305 310 315 320
Cys Ile Ala Leu Gly Tyr Thr Asn Ser Cys Leu Asn Pro Val Leu Tyr
325 330 335
Ala Phe Leu Asp Glu Asn Phe Lys Arg Cys Phe Arg Glu Phe Cys Ile
340 345 350
Pro Thr Ser Ser Thr Ile Glu Gln Gln Asn Ser Ala Arg Ile Arg Gln
355 360 365
Asn Thr Arg Glu His Pro Ser Thr Ala Asn Thr Val Asp Arg Thr Asn
370 375 380
His Gln Thr Ser Leu Thr Leu Gln
385 390

Figure 35

MOR-1BIV

Met Asp Ser Ser Ala Gly Pro Gly Asn Ile Ser Asp Cys Ser Asp Pro
1 5 10 15
Leu Ala Pro Ala Ser Cys Ser Pro Ala Pro Gly Ser Trp Leu Asn Leu
20 25 30
Ser His Val Asp Gly Asn Gln Ser Asp Pro Cys Gly Pro Asn Arg Thr
35 40 45
Gly Leu Gly Gly Ser His Ser Leu Cys Pro Gln Thr Gly Ser Pro Ser
50 55 60
Met Val Thr Ala Ile Thr Ile Met Ala Leu Tyr Ser Ile Val Cys Val
65 70 75 80
Val Gly Leu Phe Gly Asn Phe Leu Val Met Tyr Val Ile Val Arg Tyr
85 90 95
Thr Lys Met Lys Thr Ala Thr Asn Ile Tyr Ile Phe Asn Leu Ala Leu
100 105 110
Ala Asp Ala Leu Ala Thr Ser Thr Leu Pro Phe Gln Ser Val Asn Tyr
115 120 125
Leu Met Gly Thr Trp Pro Phe Gly Asn Ile Leu Cys Lys Ile Val Ile
130 135 140
Ser Ile Asp Tyr Tyr Asn Met Phe Thr Ser Ile Phe Thr Leu Cys Thr
145 150 155 160
Met Ser Val Asp Arg Tyr Ile Ala Val Cys His Pro Val Lys Ala Leu
165 170 175

```
Asp Phe Arg Thr Pro Arg Asn Ala Lys Ile Val Asn Val Cys Asn Trp
            180                 185                 190
Ile Leu Ser Ser Ala Ile Gly Leu Pro Val Met Phe Met Ala Thr Thr
        195                 200                 205
Lys Tyr Arg Gln Gly Ser Ile Asp Cys Thr Leu Thr Phe Ser His Pro
    210                 215                 220
Thr Trp Tyr Trp Glu Asn Leu Leu Lys Ile Cys Val Phe Ile Phe Ala
225                 230                 235                 240
Phe Ile Met Pro Val Leu Ile Ile Thr Val Cys Tyr Gly Leu Met Ile
                245                 250                 255
Leu Arg Leu Lys Ser Val Arg Met Leu Ser Gly Ser Lys Glu Lys Asp
            260                 265                 270
Arg Asn Leu Arg Arg Ile Thr Arg Met Val Leu Val Val Val Ala Val
        275                 280                 285
Phe Ile Val Cys Trp Thr Pro Ile His Ile Tyr Val Ile Ile Lys Ala
    290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
            340                 345                 350
Pro Thr Ser Ser Thr Ile Glu Gln Gln Asn Ser Ala Arg Ile Arg Gln
        355                 360                 365
Asn Thr Arg Glu His Pro Ser Thr Ala Asn Thr Val Asp Arg Thr Asn
    370                 375                 380
His Gln Ala His Gln Lys Pro Gln Glu Cys Leu Lys Cys Arg Cys Leu
385                 390                 395                 400
Ser Leu Thr Ile Leu Val Ile Cys Leu His Phe Gln His Gln Gln Phe
                405                 410                 415
Phe Ile Met Ile Lys Lys Asn Val Ser
            420                 425
```

Figure 36

MOR-10

```
Met Asp Ser Ser Ala Gly Pro Gly Asn Ile Ser Asp Cys Ser Asp Pro
1               5                   10                  15
Leu Ala Pro Ala Ser Cys Ser Pro Ala Pro Gly Ser Trp Leu Asn Leu
            20                  25                  30
Ser His Val Asp Gly Asn Gln Ser Asp Pro Cys Gly Pro Asn Arg Thr
        35                  40                  45
Gly Leu Gly Gly Ser His Ser Leu Cys Pro Gln Thr Gly Ser Pro Ser
    50                  55                  60
Met Val Thr Ala Ile Thr Ile Met Ala Leu Tyr Ser Ile Val Cys Val
65                  70                  75                  80
Val Gly Leu Phe Gly Asn Phe Leu Val Met Tyr Val Ile Val Arg Tyr
                85                  90                  95
Thr Lys Met Lys Thr Ala Thr Asn Ile Tyr Ile Phe Asn Leu Ala Leu
            100                 105                 110
Ala Asp Ala Leu Ala Thr Ser Thr Leu Pro Phe Gln Ser Val Asn Tyr
        115                 120                 125
Leu Met Gly Thr Trp Pro Phe Gly Asn Ile Leu Cys Lys Ile Val Ile
    130                 135                 140
Ser Ile Asp Tyr Tyr Asn Met Phe Thr Ser Ile Phe Thr Leu Cys Thr
145                 150                 155                 160
Met Ser Val Asp Arg Tyr Ile Ala Val Cys His Pro Val Lys Ala Leu
                165                 170                 175
Asp Phe Arg Thr Pro Arg Asn Ala Lys Ile Val Asn Val Cys Asn Trp
            180                 185                 190
```

```
Ile Leu Ser Ser Ala Ile Gly Leu Pro Val Met Phe Met Ala Thr Thr
        195                 200                 205
Lys Tyr Arg Gln Gly Ser Ile Asp Cys Thr Leu Thr Phe Ser His Pro
    210                 215                 220
Thr Trp Tyr Trp Glu Asn Leu Leu Lys Ile Cys Val Phe Ile Phe Ala
225                 230                 235                 240
Phe Ile Met Pro Val Leu Ile Ile Thr Val Cys Tyr Gly Leu Met Ile
                245                 250                 255
Leu Arg Leu Lys Ser Val Arg Met Leu Ser Gly Ser Lys Glu Lys Asp
            260                 265                 270
Arg Asn Leu Arg Arg Ile Thr Arg Met Val Leu Val Val Val Ala Val
        275                 280                 285
Phe Ile Val Cys Trp Thr Pro Ile His Ile Tyr Val Ile Ile Lys Ala
    290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
            340                 345                 350
Pro Thr Ser Ser Thr Ile Glu Gln Gln Asn Ser Ala Arg Ile Arg Gln
        355                 360                 365
Asn Thr Arg Glu His Pro Ser Thr Ala Asn Thr Val Asp Arg Thr Asn
    370                 375                 380
His Gln Ile Met Lys Phe Glu Ala Ile Tyr Pro Lys Leu Ser Phe Lys
385                 390                 395                 400
Ser Trp Ala Leu Lys Tyr Phe Thr Phe Ile Arg Glu Lys Lys Arg Asn
                405                 410                 415
Thr Lys Ala Gly Ala Leu Pro Pro Leu Pro Thr Cys His Ala Gly Ser
            420                 425                 430
Pro Ser Gln Ala His Arg Gly Val Ala Ala Trp Leu Leu Pro Leu Arg
        435                 440                 445
His Met Gly Pro Ser Tyr Pro Ser
    450                 455
```

Figure 37 hMOR-10

```
Met Asp Ser Ser Ala Ala Pro Thr Asn Ala Ser Asn Cys Thr Asp Ala
1               5                   10                  15
Leu Ala Tyr Ser Ser Cys Ser Pro Ala Pro Ser Pro Gly Ser Trp Val
            20                  25                  30
Asn Leu Ser His Leu Asp Gly Asn Leu Ser Asp Pro Cys Gly Pro Asn
        35                  40                  45
Arg Thr Asp Leu Gly Gly Arg Asp Ser Leu Cys Pro Pro Thr Gly Ser
    50                  55                  60
Pro Ser Met Ile Thr Ala Ile Thr Ile Met Ala Leu Tyr Ser Ile Val
65                  70                  75                  80
Cys Val Val Gly Leu Phe Gly Asn Phe Leu Val Met Tyr Val Ile Val
                85                  90                  95
Arg Tyr Thr Lys Met Lys Thr Ala Thr Asn Ile Tyr Ile Phe Asn Leu
            100                 105                 110
Ala Leu Ala Asp Ala Leu Ala Thr Ser Thr Leu Pro Phe Gln Ser Val
        115                 120                 125
Asn Tyr Leu Met Gly Thr Trp Pro Phe Gly Thr Ile Leu Cys Lys Ile
    130                 135                 140
Val Ile Ser Ile Asp Tyr Tyr Asn Met Phe Thr Ser Ile Phe Thr Leu
145                 150                 155                 160
Cys Thr Met Ser Val Asp Arg Tyr Ile Ala Val Cys His Pro Val Lys
                165                 170                 175
```

```
Ala Leu Asp Phe Arg Thr Pro Arg Asn Ala Lys Ile Ile Asn Val Cys
            180                 185                 190
Asn Trp Ile Leu Ser Ser Ala Ile Gly Leu Pro Val Met Phe Met Ala
        195                 200                 205
Thr Thr Lys Tyr Arg Gln Gly Ser Ile Asp Cys Thr Leu Thr Phe Ser
    210                 215                 220
His Pro Thr Trp Tyr Trp Glu Asn Leu Leu Lys Ile Cys Val Phe Ile
225                 230                 235                 240
Phe Ala Phe Ile Met Pro Val Leu Ile Ile Thr Val Cys Tyr Gly Leu
                245                 250                 255
Met Ile Leu Arg Leu Lys Ser Val Arg Met Leu Ser Gly Ser Lys Glu
            260                 265                 270
Lys Asp Arg Asn Leu Arg Arg Ile Thr Arg Met Val Leu Val Val Val
        275                 280                 285
Ala Val Phe Ile Val Cys Trp Thr Pro Ile His Ile Tyr Val Ile Ile
    290                 295                 300
Lys Ala Leu Val Thr Ile Pro Glu Thr Thr Phe Gln Thr Val Ser Trp
305                 310                 315                 320
His Phe Cys Ile Ala Leu Gly Tyr Thr Asn Ser Cys Leu Asn Pro Val
                325                 330                 335
Leu Tyr Ala Phe Leu Asp Glu Asn Phe Lys Arg Cys Phe Arg Glu Phe
            340                 345                 350
Cys Ile Pro Thr Ser Ser Asn Ile Glu Gln Gln Asn Ser Thr Arg Ile
        355                 360                 365
Arg Gln Asn Thr Arg Asp His Pro Ser Thr Ala Asn Thr Val Asp Arg
    370                 375                 380
Thr Asn His Gln Cys Leu Pro Ile Pro Ser Leu Ser Cys Trp Ala Leu
385                 390                 395                 400
Glu His Gly Cys Leu Val Val Tyr Pro Gly Pro Leu Gln Gly Pro Leu
                405                 410                 415
Val Arg Tyr Asp Leu Pro Ala Ile Leu His Ser Ser Cys Leu Arg Gly
            420                 425                 430
Asn Thr Ala Pro Ser Pro Ser Gly Gly Ala Phe Leu Leu Ser
        435                 440                 445
```

Figure 38 hMOR-1P

```
Met Asp Ser Ser Ala Ala Pro Thr Asn Ala Ser Asn Cys Thr Asp Ala
1               5                   10                  15
Leu Ala Tyr Ser Ser Cys Ser Pro Ala Pro Ser Pro Gly Ser Trp Val
            20                  25                  30
Asn Leu Ser His Leu Asp Gly Asn Leu Ser Asp Pro Cys Gly Pro Asn
        35                  40                  45
Arg Thr Asp Leu Gly Gly Arg Asp Ser Leu Cys Pro Pro Thr Gly Ser
    50                  55                  60
Pro Ser Met Ile Thr Ala Ile Thr Ile Met Ala Leu Tyr Ser Ile Val
65                  70                  75                  80
Cys Val Val Gly Leu Phe Gly Asn Phe Leu Val Met Tyr Val Ile Val
                85                  90                  95
Arg Tyr Thr Lys Met Lys Thr Ala Thr Asn Ile Tyr Ile Phe Asn Leu
            100                 105                 110
Ala Leu Ala Asp Ala Leu Ala Thr Ser Thr Leu Pro Phe Gln Ser Val
        115                 120                 125
Asn Tyr Leu Met Gly Thr Trp Pro Phe Gly Thr Ile Leu Cys Lys Ile
    130                 135                 140
Val Ile Ser Ile Asp Tyr Tyr Asn Met Phe Thr Ser Ile Phe Thr Leu
145                 150                 155                 160
Cys Thr Met Ser Val Asp Arg Tyr Ile Ala Val Cys His Pro Val Lys
                165                 170                 175
```

```
Ala Leu Asp Phe Arg Thr Pro Arg Asn Ala Lys Ile Ile Asn Val Cys
            180                 185                 190
Asn Trp Ile Leu Ser Ser Ala Ile Gly Leu Pro Val Met Phe Met Ala
        195                 200                 205
Thr Thr Lys Tyr Arg Gln Gly Ser Ile Asp Cys Thr Leu Thr Phe Ser
    210                 215                 220
His Pro Thr Trp Tyr Trp Glu Asn Leu Leu Lys Ile Cys Val Phe Ile
225                 230                 235                 240
Phe Ala Phe Ile Met Pro Val Leu Ile Ile Thr Val Cys Tyr Gly Leu
                245                 250                 255
Met Ile Leu Arg Leu Lys Ser Val Arg Met Leu Ser Gly Ser Lys Glu
            260                 265                 270
Lys Asp Arg Asn Leu Arg Arg Ile Thr Arg Met Val Leu Val Val Val
        275                 280                 285
Ala Val Phe Ile Val Cys Trp Thr Pro Ile His Ile Tyr Val Ile Ile
    290                 295                 300
Lys Ala Leu Val Thr Ile Pro Glu Thr Thr Phe Gln Thr Val Ser Trp
305                 310                 315                 320
His Phe Cys Ile Ala Leu Gly Tyr Thr Asn Ser Cys Leu Asn Pro Val
                325                 330                 335
Leu Tyr Ala Phe Leu Asp Glu Asn Phe Lys Arg Cys Phe Arg Glu Phe
            340                 345                 350
Cys Ile Pro Thr Ser Ser Asn Ile Glu Gln Gln Asn Ser Thr Arg Ile
        355                 360                 365
Arg Gln Asn Thr Arg Asp His Pro Ser Thr Ala Asn Thr Val Asp Arg
    370                 375                 380
Thr Asn His Gln Pro Pro Leu Ala Val Ser Met Ala Gln Ile Phe Thr
385                 390                 395                 400
Arg Tyr Pro Pro Pro Thr His Arg Glu Lys Thr Cys Asn Asp Tyr Met
                405                 410                 415
Lys Arg
```

Figure 39

MOR-1p

```
ggaacccgaa cactcttgag tgctctcagt tacagcctac cgagtccgca gcaagcattc
60
agaaccatgg acagcagcgc cggcccaggg aacatcagcg actgctctga ccccttagct
120
cctgcaagtt gctccccagc acctggctcc tggctcaact tgtcccacgt tgatggcaac
180
cagtccgacc catgcggtcc taaccgcacg ggcttggcg ggagccacag cctgtgccct
240
cagaccggca gcccttccat ggtcacagcc atcaccatca tggccctcta ttctatcgtg
300
tgtgtagtgg gcctctttgg aaacttcctg gtcatgtatg tgattgtaag atataccaaa
360
atgaagactg ccaccaacat ctacattttc aaccttgctc tggcagatgc cttagccact
420
agcacgctgc cctttcagag tgttaactac ctgatgggaa cgtggccctt tggaaacatc
480
ctctgcaaga tcgtgatctc aatagactac tacaacatgt tcaccagtat cttcaccctc
540
tgcaccatga gtgtagaccg ctacattgcc gtctgccacc cggtcaaggc cctggatttc
600
cgtacccccc gaaatgccaa aattgtcaat gtctgcaact ggatcctctc ttctgccatt
660
ggtctgcccg taatgttcat ggcaaccaca aaatacaggc aggggtccat agattgcacc
720
```

ctcacgttct ctcatcccac atggtactgg gagaacctgc tcaaaatctg tgtcttcatc
780
ttcgccttca tcatgccggt cctcatcatc actgtgtgtt atggactgat gatcttacga
840
ctcaagagtg tccgcatgct gtcgggctcc aaagaaaagg acaggaacct gcgcaggatc
900
acccggatgg tgctggtggt cgtggctgta tttattgtct gctggacccc catccacatc
960
tatgtcatca tcaaagcact gatcacgatt ccagaaacca ctttccagac tgtttcctgg
1020
cacttctgca ttgccttggg ttacacaaac agctgcctga acccagttct ttatgcgttc
1080
ctggatgaaa acttcaaacg atgttttaga gagttctgca tcccaacttc ctccacaatc
1140
gaacagcaaa actctgctcg aatccgtcaa aacactaggg aacacccctc cacggctaat
1200
acagtggatc gaactaacca ccagccaacc ctggcagtca gcgtggccca gatctttaca
1260
ggatatcctt ctccgactca tgttgaaaaa ccctgcaaga gttgcatgga caggtgagtg
1320
tgacccggac tcaggtgaca aaataaaagg caagttttag ctttttgcac ggc
1373

Figure 40
MOR-1P
Met Asp Ser Ser Ala Gly Pro Gly Asn Ile Ser Asp Cys Ser Asp Pro
1 5 10 15
Leu Ala Pro Ala Ser Cys Ser Pro Ala Pro Gly Ser Trp Leu Asn Leu
20 25 30
Ser His Val Asp Gly Asn Gln Ser Asp Pro Cys Gly Pro Asn Arg Thr
35 40 45
Gly Leu Gly Gly Ser His Ser Leu Cys Pro Gln Thr Gly Ser Pro Ser
50 55 60
Met Val Thr Ala Ile Thr Ile Met Ala Leu Tyr Ser Ile Val Cys Val
65 70 75 80
Val Gly Leu Phe Gly Asn Phe Leu Val Met Tyr Val Ile Val Arg Tyr
85 90 95
Thr Lys Met Lys Thr Ala Thr Asn Ile Tyr Ile Phe Asn Leu Ala Leu
100 105 110
Ala Asp Ala Leu Ala Thr Ser Thr Leu Pro Phe Gln Ser Val Asn Tyr
115 120 125
Leu Met Gly Thr Trp Pro Phe Gly Asn Ile Leu Cys Lys Ile Val Ile
130 135 140
Ser Ile Asp Tyr Tyr Asn Met Phe Thr Ser Ile Phe Thr Leu Cys Thr
145 150 155 160
Met Ser Val Asp Arg Tyr Ile Ala Val Cys His Pro Val Lys Ala Leu
165 170 175
Asp Phe Arg Thr Pro Arg Asn Ala Lys Ile Val Asn Val Cys Asn Trp
180 185 190
Ile Leu Ser Ser Ala Ile Gly Leu Pro Val Met Phe Met Ala Thr Thr
195 200 205
Lys Tyr Arg Gln Gly Ser Ile Asp Cys Thr Leu Thr Phe Ser His Pro
210 215 220
Thr Trp Tyr Trp Glu Asn Leu Leu Lys Ile Cys Val Phe Ile Phe Ala
225 230 235 240
Phe Ile Met Pro Val Leu Ile Ile Thr Val Cys Tyr Gly Leu Met Ile
245 250 255
Leu Arg Leu Lys Ser Val Arg Met Leu Ser Gly Ser Lys Glu Lys Asp
260 265 270

```
Arg Asn Leu Arg Arg Ile Thr Arg Met Val Leu Val Val Val Ala Val
        275                 280                 285
Phe Ile Val Cys Trp Thr Pro Ile His Ile Tyr Val Ile Ile Lys Ala
    290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
            340                 345                 350
Pro Thr Ser Ser Thr Ile Glu Gln Gln Asn Ser Ala Arg Ile Arg Gln
        355                 360                 365
Asn Thr Arg Glu His Pro Ser Thr Ala Asn Thr Val Asp Arg Thr Asn
    370                 375                 380
His Gln Pro Thr Leu Ala Val Ser Val Ala Gln Ile Phe Thr Gly Tyr
385                 390                 395                 400
Pro Ser Pro Thr His Val Glu Lys Pro Cys Lys Ser Cys Met Asp Arg
                405                 410                 415
```

MU-OPIOD RECEPTOR SPLICE VARIANT POLYPEPTIDES

RELATED APPLICATIONS/PATENTS & INCORPORATION BY REFERENCE

This application claims priority to U.S. Provisional Application No. 60/302,072, filed Jun. 29, 2001, the contents of which are expressly incorporated herein by reference.

STATEMENT OF RIGHTS TO INVENTION MADE UNDER FEDERALLY SPONSORED RESEARCH

This work was supported by the government, in part, by grants from the National Institute on Drug Abuse (DA02615 and DA07241); a Senior Scientist Award (DA00220) to Gavril W. Pasternak; a Mentored Scientist Award (DA00296) to Ying-Xian Pan; a grant from the National Genetics Foundation; and a core grant to Memorial Sloan-Kettering Cancer Center, New York, N.Y. (CA08748) from the National Cancer Institute. The government may have certain rights to this invention.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein cited references"), as well as each document or reference cited in each of the herein-cited references (including any manufacturer's specifications, instructions, etc.), is hereby expressly incorporated herein by reference.

TECHNICAL FIELD

The present invention relates to mu-opioid receptor-1 (MOR-1) splice variant polypeptides, to DNA sequences encoding the splice variants, to DNA sequences encompassing non-coding region splice variants, to methods of screening compositions for agonists and antagonists of the splice variant receptor activities and to methods of measuring splice variant binding activities.

BACKGROUND ART

Opiates are drugs derived from opium and include morphine, codeine and a wide variety of semisynthetic opioid congeners derived from them and from thebaine, another component of opium. Opioids include the opiates and all agonists and antagonists with morphine-like activity and naturally occurring endogenous and synthetic opioid peptides. Morphine and other morphine-like opioid agonists are commonly used pharmaceutically to produce analgesia.

There are now many compounds with pharmacological properties similar to those produced by morphine, but none has proven to be clinically superior in relieving pain. References to morphine herein will be understood to include morphine-like agonists as well. The effects of morphine on human beings are relatively diverse and include analgesia, drowsiness, changes in mood, respiratory depression, decreased gastrointestinal motility, nausea, vomiting, and alterations of the endocrine and autonomic nervous systems. Pasternak (1993) Clin. Neuropharmacol. 16:1. Doses of morphine need to be tailored based on individual sensitivity to the drug and the pain-sparing needs of the individual. For instance, the typical initial dose of morphine (10 mg/70 kg) relieves post-operative pain satisfactorily in only two-thirds of patients. Likewise, responses of an individual patient may vary dramatically with different morphine-like drugs and patients may have side effects with one such drug and not another. For example, it is known that some patients who are unable to tolerate morphine may have no problems with an equianalgesic dose of methadone. The mechanisms underlying variations in individual responses to morphine and morphine-like agonists have not been defined.

The analgesic effects of morphine are transduced through opioid receptors in the central nervous system (CNS), located at both spinal and multiple supraspinal sites. Morphine and other agonists induce profound analgesia when administered intrathecally or instilled locally into the dorsal horn of the spinal cord. Several mechanisms of action are believed to mediate the inhibition of nociceptive reflexes from reaching higher centers of the brain, including the inhibition of neurotransmitter release by opioid receptors on the termini of primary afferent nerves and post synaptic inhibitory actions on interneurons and on the out-put neurons of the spinothalamic tract.

Profound analgesia can also be produced by the instillation of morphine into the third ventricle or within various sites in the midbrain and medulla, most notably the periaqueductal gray matter, the nucleus raphe magnus, and the locus ceruleus. Although the neuronal circuitry responsible has not been defined, these actions produce enhanced activity in the descending aminergic bulbospinal pathways that exert inhibitory effects on the processing of nociceptive information in the spinal cord. Simultaneous administration of morphine at both spinal and supraspinal sites results in a synergized analgesic response, with a ten-fold reduction in the total dose of morphine necessary to produce equivalent analgesia at either site alone.

Morphine also exerts effects on the neuroendocrine system. Morphine acts in the hypothalamus to inhibit the release of gonadotropin releasing hormone (GnRH) and corticotropin-releasing factor (CRF), thus decreasing circulating concentrations of luteinizing hormone (LH), follicle stimulating hormone (FSH), and adrenocorticotropin (ACTH), and β-endorphin. As a result of the decreased concentrations of pituitary trophic hormones, the concentrations of testosterone and cortisol in the plasma decline. The administration of opiates increases the concentration of prolactin (PRL) in plasma, most likely by reducing the dopaminergic inhibition of PRL secretion. With chronic administration, tolerance eventually develops to the effects of morphine on hypothalamic releasing factors.

Opiates can interfere with normal gastrointestinal functioning. Morphine decreases both gastric motility and the secretion of hydrochloric acid in the stomach. Morphine may delay passage of gastric contents through the duodenum for as long as 12 hours. Morphine also decreases biliary, pancreatic and intestinal secretions and delays the digestion of food in the small intestine. Propulsive peristaltic waves in the colon are diminished or abolished after administration of morphine and commonly, constipation occurs. For a detailed review of the physiological effects of morphine, see Reisine and Pasternak (1996) Goodman & Gilman's The pharmacological basis of therapeutics, Ninth Edition (Hardman et al. eds.) McGraw-Hill pp. 521–555.

Morphine also exerts effects on the immune system. The most firmly established effect of morphine is its ability to inhibit the formation of rosettes by human lymphocytes. The administration of morphine to animals causes suppression of the cytotoxic activity of natural killer cells and enhances the growth of implanted tumors. These effects appear to be mediated by actions within the CNS. By contrast, β-endorphin enhances the cytotoxic activity of human monocytes in vitro and increases the recruitment of precursor cells into the killer cell population; this peptide also can exert a potent chemotactic effect on these cells. A novel type of receptor (designated ∈) may be involved. These effects, combined with the synthesis of Proopiomelanocortin (POMC) and preproenkephalin by various cells of the immune system, have stimulated studies of the potential role of opioids in the regulation of immune function. Sibinga and Goldstein (1988) Annu. Rev. Immunol. 6:219.

Side effects resulting from the use of morphine range from mild to life threatening. Morphine causes constriction of the pupil by an excitatory action on the parasympathetic nerve innervating the pupil. Morphine depresses the cough reflex through inhibitory effects on the cough centers in the medulla. Nausea and vomiting occur in some individuals through direct stimulation of the chemoreceptor trigger zone for emesis, in the postrema of the medulla. Therapeutic doses of morphine also result in peripheral vasodilatation, reduced peripheral resistance and an inhibition of baroreceptor reflexes in the cardiovascular system. Additionally, morphine provokes the release of histamines, which can cause hypotension. Morphine depresses respiration, at least in part by direct effects on the brainstem regulatory systems. In humans, death from morphine poisoning is nearly always due to respiratory arrest. Opioid antagonists can produce a dramatic reversal of severe respiratory depression and naloxone is currently the treatment of choice. High doses of morphine and related opioids can produce convulsions that are not always relieved by naloxone.

The development of tolerance and physical dependence with repeated use is a characteristic feature of all opiates. Dependence seems to be closely related to tolerance, since treatments that block tolerance to morphine also block dependence. In vivo studies in animal models demonstrate the importance of neurotransmitters and their interactions with opioid pathways in the development of tolerance to morphine. Blockade of glutamate actions by noncompetitive and competitive NMDA (N-methyl-D-aspartate) antagonists blocks morphine tolerance. Trujillo and Akil (1991) Science 251:85; and Elliott et al. (1994) Pain 56:69. Blockade of the glycine regulatory site on NMDA receptors has similar effects to block tolerance. Kolesnikov et al. (1994) Life Sci. 55:1393. Administering inhibitors of nitric oxide synthase in morphine-tolerant animals reverses tolerance, despite continued opioid administration. Kolesnikov et al. (1993) Proc. Natl. Acad. Sci. U.S.A. 90:5162. These studies indicate several important aspects of tolerance and dependence. First, the selective actions of drugs on tolerance and dependence demonstrate that analgesia can be dissociated from these two unwanted actions. Second, the reversal of preexisting tolerance by NMDA antagonists and nitric oxide synthase inhibitors indicates that tolerance is a balance between activation of processes and reversal of those processes. These observations suggest that, by use of selective agonists and/or antagonists, tolerance and dependence in the clinical management of pain can be minimized or disassociated from the therapeutic effects.

In addition to morphine, there are a variety of opioids suitable for clinical use. These include, but are not limited to, Levorphanol, Meperidine, Fentanyl, Methadone, Codeine, Propoxyphene and various opioid peptides. Certain opioids are mixed agonists/antagonists and partial agonists. These include pentazocine, nalbuphine, butorphanol, and buprenorphine. The pharmacological effects of levorphanol closely parallel those of morphine although clinical reports suggest that levorphanol produces less nausea.

Meperidine exerts its chief pharmacological effects on the central nervous system and the neural elements in the bowel. Meperidine produces a pattern of effects similar but not identical to those described for morphine. In equianalgesic doses, meperidine produces as much sedation, respiratory depression, and euphoria as morphine. The pattern of unwanted side effects that follow the use of meperidine are similar to those observed after equianalgesic doses of morphine, except that constipation and urinary retention are less common.

Fentanyl is a synthetic opioid estimated to be 80 times as potent as morphine as an analgesic. High doses of fentanyl can result in severe toxicity and produce side effects including muscular rigidity and respiratory depression.

Methadone is an opioid with pharmacological properties similar to morphine. The properties of methadone include effective analgesic activity, efficacy by the oral route and persistent effects with repeated administration. Side effects include detection of miotic and respiratory-depressant effects for more than 24 hours after a single dose, and marked sedation is seen in some patients. Effects on cough, bowel motility, biliary tone and the secretion of pituitary hormones are qualitatively similar to those of morphine. In contrast to morphine, codeine is approximately 60% as effective orally as parenterally, both as an analgesic and as a respiratory depressant.

Codeine has an exceptionally low affinity for opioid receptors, and the analgesic effect of codeine is due to its conversion to morphine. However, codeine's antitussive actions probably involve distinct receptors that bind codeine specifically.

Propoxyphene produces analgesia and other CNS effects that are similar to those seen with morphine. It is likely that at equianalgesic doses the incidence of side effects such as nausea, anorexia, constipation, abdominal pain, and drowsiness would be similar to those of codeine.

Opioid antagonists have therapeutic utility in the treatment of overdosage with opioids. As understanding of the role of endogenous opioid systems in pathophysiological states increases, additional therapeutic indications for these antagonists will emerge. If endogenous opioid systems have not been activated, the pharmacological actions of opioid antagonists depend on whether or not an opioid agonist has been administered previously, the pharmacological profile of that opioid and the degree to which physical dependence on an opioid has developed. The antagonist naloxone produces no discernible subjective effects aside from slight drowsiness. Naltrexone functions similarly, but with higher oral efficacy and a longer duration of action. Currently, naloxone and naltrexone are used clinically to treat opioid overdoses. Their potential utility in the treatment of shock, stroke, spinal cord and brain trauma, and other disorders that may involve mobilization of endogenous opioids remains to be established.

The complex interactions of morphine and drugs with mixed agonist/antagonist properties are mediated by multiple classes of opioid receptors. Opioid receptors comprise a family of cell surface proteins, which control a range of biological responses, including pain perception, modulation of affective behavior and motor control, autonomic nervous system regulation and neuroendocrinological function. There are three major classes of opioid receptors in the CNS, designated mu, kappa and delta, which differ in their affinity for various opioid ligands and in their cellular distribution. The different classes of opioid receptors are believed to serve different physiologic functions. Olson et al. (1989) Peptides 10:1253; Lutz and Pfister (1992) J. Receptor Res. 12:267; and Simon (1991) Medicinal Res. Rev. 11:357. Morphine produces analgesia primarily through the mu-opioid receptor. However, among the opioid receptors, there is substantial overlap of function as well as of cellular distribution.

The mu-opioid receptor mediates the actions of morphine and morphine-like opioids, including most clinical analgesics. In addition to morphine, several highly selective agonists have been developed for mu-opioid receptors, including [D-Ala$^2$,MePhe$^4$,Gly(ol)$^5$]enkephalin (DAMGO), levorphanol and methadone. Differential sensitivity to antagonists, such as naloxonazine, indicates the pharmacological distinctions between the mu-opioid receptor subtypes, $mu_1$ and $mu_2$. Several of the opioid peptides will also interact with mu-opioid receptors.

There are three distinct families of endogenous opioid peptides, the enkephalins, endorphins and dynorphins, where each peptide is derived from a distinct precursor polypeptide. Mu-opioid receptors have a high affinity for the enkephalins as well as β-endorphin and dynorphin A. For review, see Reisine and Pasternak (1996).

Members of each known class of opioid receptor have been cloned from human cDNA and their predicted amino acid sequences have been determined. Yasuda et al. (1993) Proc. Natl. Acad. Sci. U.S.A. 90:6736; and Chen et al. (1993) Mol. Pharmacol. 44:8. The opioid receptors belong to a class of transmembrane spanning receptors known as G-protein coupled receptors. G-proteins consist of three tightly associated subunits, alpha, beta and gamma (1:1:1) in order of decreasing mass. Following agonist binding to the receptor, a conformational change is transmitted to the G-protein, which causes the G-alpha subunit to exchange a bound GDP for GTP and to dissociate from the beta and gamma subunits. The GTP-bound form of the alpha subunit is typically the effector-modulating moiety. Signal amplification results from the ability of a single receptor to activate many G-protein molecules, and from the stimulation by G-alpha-GTP of many catalytic cycles of the effector.

Most opioid receptor-mediated functions appear to be mediated through G-protein interactions. Standifer and Pasternak (1997) Cell Signal. 9:237. Antisense oligodeoxynucleotides directed against various G-protein alpha subunits were shown to differentially block the analgesic actions of the mu-, delta-, and kappa-opioid agonists in mice. Standifer et al. (1996) Mol. Pharmacol. 50:293.

The amino acid sequences of the opioid receptors are approximately 65% identical, and they have little sequence similarity to other G-protein-coupled receptors except for somatostatin. Reisine and Bell (1993) Trends Neurosci. 16:506. The regions of highest similarity in sequence are the sequences predicted to lie in the seven transmembrane-spanning regions and the intracellular loops. Regions of amino acid sequence divergence are the amino and carboxy termini and the second and third extracellular loops.

Each receptor subtype has a characteristic pattern of expression. Mu-opioid receptor mRNA is present in the periaqueductal gray, spinal trigeminal nucleus, cuneate and gracile nuclei, and thalamus regions of the brain involved in pain perception and associated with morphine analgesia. Defts et al. (1994) J. Comp. Neurol. 345:46. It is also present in nuclei involved in control of respiration, consistent with the ability of morphine to depress respiration, and in neurons of the area postrema, where morphine has been shown to cause nausea and induce vomiting. Other consequences of mu-opioid receptor activation include miosis, reduced gastrointestinal motility, and feelings of well-being or euphoria. Pasternak (1993). The pattern of mu-opioid receptor mRNA expression correlates with the brain centers involved in mediating the biological actions of morphine and mu-selective agonists. Delta-opioid receptor mRNA is found in the dorsal horn of the spinal cord. $Kappa_1$-opioid receptor mRNA is expressed in the hypothalamic regions, which may account for many of the neuroendocrine effects of the kappa selective agonists.

Soon after the mu-opioid receptor MOR-1 was cloned (Chen et al. (1993); and Wang et al. (1993) Proc. Natl. Acad. Sci. U.S.A. 90:10230), antisense experiments confirmed its involvement with morphine analgesia. Rossi et al. (1994) Life Sci. 54:375; and Rossi et al. (1995) FEBS Lett. 369: 192. Antisense oligonucleotides directed against MOR-1 mRNA blocked the analgesic actions of morphine in rats, demonstrating that proper translation of the MOR-1 mRNA was essential for modulating morphine analgesia. Antisense approaches have also demonstrated a relationship between MOR-1 activity and ingestive responses. Administration of antisense oligonucleotides directed against MOR-1 mRNA significantly reduced food and water intake and subsequently, body weight in rats.

In recent years, a number of mu-opioid receptor subtypes have been proposed. The first suggestion of $mu_1$ and $mu_2$ receptor subtypes came from a combination of binding and pharmacological studies based on the antagonists naloxonazine and naloxazone. Wolozin and Pasternak (1981) Proc. Natl. Acad. Sci. U.S.A. 78:6181; Reisine and Pasternak (1996); and Pasternak (1993). A gene encoding a mu receptor, MOR-1, has been identified. Min et al. (1994) Proc. Natl. Acad. Sci. U.S.A. 91:9081; Giros et al. (1995) Life Sci. 56:PL369; and Liang et al. (1995) Brain Res. 679:82. The MOR-1 cDNA consists of exons 1–4, which total 1610 bp in length and encode 398 amino acids. More recently, pharmacological and molecular differences between morphine and morphine-6β-glucuronide (M6G) have suggested yet another mu-opioid receptor subtype. Pasternak and Standifer (1995) Trends Pharmacol. Sci. 16:344; Rossi et al. (1995); and Rossi et al. (1996) Neurosci. Lett. 216:1.

Antisense oligonucleotides directed against selected exons within the MOR-1 mRNA revealed interesting therapeutic patterns of morphine and M6G analgesia, with some MOR-1 exons implicated in the analgesic actions of one drug, but not the other. Rossi et al. (1997) J. Pharmacol. Exp. Ther. 281:109; and Rossi et al. (1995). Although the two analgesics were known to act through different receptors, the sensitivity of the effect of both analgesics to at least six different MOR-1 antisense probes implied that both receptors were closely associated with MOR-1, raising the possibility of pharmacologically relevant MOR-1 splice variants. Pasternak and Standifer (1995); and Rossi et al. (1995). Alternative splicing has been observed with a number of G-protein-coupled receptors, including somatostatin 2 (Vanetti et al. (1998) FEBS Lett. 311:290), dopamine D2 (Guiramand et al. (1995) J. Biol. Chem. 270:7354), prostaglandin EP3 (Namba et al. (1993) Trends Pharmacol. Sci. 16:246), serotonin receptor subtypes 5-$HT_4$ and 5-$HT_7$ (Lucas and Hen. (1995) Trends Pharmacol. Sci. 16:246) and MOR-1 (Bare et al. (1994) FEBS Lett. 354:213; and Zimprich et al. (1995) FEBS Lett. 359:142).

Several opioid receptor splice variants have been identified and characterized. At least two MOR-1 splice variants are known, the human MOR-1A and the rat MOR-1B. Bare et al. (1994); and Zimprich et al. (1995). The hMOR-1A splice variant consists of exons 1, 2, 3 and a new exon 3a, and was determined to possess ligand binding characteristics similar to the full-length MOR-1. Bare et al. (1994). The rMOR-1B splice variant consists of exons 1, 2, 3 and a new exon 5, and like hMOR-1A, differs from MOR-1 only in length and amino acid composition at the carboxy-terminal tail. Zimprich et al. (1995). MOR-1B has affinity to opioid compounds similar to that of MOR-1, but is much more resistant to agonist-induced desensitization than MOR-1. The C-terminal differences between MOR-1 and MOR-1A or MOR-1B could have effects on receptor coupling or receptor transport and localization. Twelve splice variants, comprised of nine exons, of the mouse MOR-1 gene were recently identified and characterized. (PCT/US99/15974, published as WO 00/04046). The MOR-1 splice variants are potential targets for the modulation of physiological effects resulting from mu-opioid receptor activity. In addition, seven splice variants of the kappa opioid receptor have been identified and characterized, suggesting an analogous system of modulation to that of the mu class of receptors. (PCT/US99/15977, published as WO 00/04151).

Availability of polynucleotide sequences of opioid receptor splice variants, and, in the case of splice variants in coding regions, the corresponding polypeptide sequences, will significantly increase the capability to design pharmaceutical compositions, such as analgesics, with enhanced specificity of function. In general, the availability of these polynucleotide and polypeptide sequences will enable efficient screening of candidate compositions. The principle in operation through the screening process is straightforward: natural agonists and antagonists bind to cell-surface receptors and channels to produce physiological effects; certain other molecules can produce physiological effects and act as therapeutic pharmaceutical agents. Thus, the ability of candidate drugs to bind to opioid receptor splice variants can function as an extremely effective screening criterion for the selection of pharmaceutical compositions with desired functional efficacy and specificity.

DISCLOSURE OF THE INVENTION

The invention encompasses MOR-1 splice variant polypeptides or polypeptide fragments or homologs thereof retaining MOR-1 activity.

The invention further encompasses a MOR-1 splice variant polynucleotide, encoding MOR-1 splice variant polypeptides or polypeptide fragments or homologs thereof retaining MOR-1 activity, and noncoding mRNA splice variants and complementary strands thereto.

The invention further encompasses a polynucleotide, or a complementary strand thereto that hybridizes under stringent conditions, comprising at least 15 consecutive nucleotides of an MOR-1 splice variant polynucleotide where the polynucleotide contains promoter elements.

The invention further encompasses methods of screening compositions for an opioid activity by obtaining a control cell that does not express a recombinant or endogenous opioid receptor, obtaining a test cell that expresses a recombinant MOR-1 splice variant polypeptide, contacting the control cell and test cell with an amount of an opioid sufficient to exert a physiologic effect, separately measuring the physiologic effect of the composition on the control cell and test cell and comparing the physiologic effect of the composition to the physiologic effect of the opioid, where determination of a physiologic effect of the composition is expressed relative to that of the opioid.

The invention further encompasses methods of screening compositions for an opioid activity by obtaining a control polypeptide that is not a recombinant opioid receptor, obtaining a test polypeptide that is a recombinant MOR-1 splice variant polypeptide, contacting a composition with the control polypeptide and the test polypeptide, contacting the test polypeptide with an amount of an opioid sufficient to measurably bind the test polypeptide, measuring the binding of the composition and the opioid, and comparing the test polypeptide binding of the composition to that of the opioid, where determination of binding of the composition is expressed relative to that of the opioid.

The invention further encompasses methods of screening compositions for differential or selective opioid activity comprising obtaining a first and second test polypeptide that are MOR-1 splice variant polypeptide fragments and contacting each with a composition, measuring the binding affinity of the composition to the first and second test polypeptides and comparing the binding of the composition and the first test polypeptide to that of the second test polypeptide where differential activity is expressed as a ratio of the two binding affinities.

The invention further encompasses a method for regulating morphine analgesia in a subject by altering of MOR-1 splice variant polypeptide activity. Activity can be regulated by administering antigen binding fragments, agonists, antagonists, small molecule ligands or antisense nucleic acids to a subject in an amount and for a duration sufficient to regulate morphine analgesia. The antigen binding fragment, agonist, antagonist, small molecule ligand or anti sense nucleic acid is directed to an MOR-1 splice variant polypeptide fragment or a homolog thereof or an MOR-1 splice variant mRNA.

The invention further encompasses regulating opioid activity by administering a DNA plasmid vector containing an MOR-1 splice variant polynucleotide. The DNA plasmid vector thereby expresses an mRNA splice variant that may encode an MOR-1 polypeptide in a subject in an amount of and duration sufficient to regulate morphine analgesia. Activity can also be regulated by administering an antisense nucleic acid complementary to an MOR-1 splice variant polynucleotide, thereby blocking gene expression in a subject in an amount and duration sufficient to regulate morphine analgesia.

The invention further encompasses antigen-binding fragments specific for the MOR-1 splice variant polypeptides described herein.

BRIEF DESCRIPTION OF THE DRAWINGS

FIG. 3 depicts the predicted amino acid sequences of several variants, SEQ ID NOS: 53, 28–32, 55 and 56, respectively in order of appearance. The amino acid sequences were determined from the variant cDNAs by using the exon 11 AUG as a translation codon. The partial amino acid sequences deduced from the exons 2 and 3 in MOR-1G (SEQ ID NO: 53), MOR-1M (SEQ ID NO:55) and MOR-1N (SEQ ID NO: 56), which are the same as that of MOR-1, are omitted in dashed lines. Glycine residues corresponding to potential N-myristoylation site (V), potential phosphorylation sites for cAMP and cGMP-dependent protein kinase (*), and Casein kinase (•) and sites and Casein kinase II (o) are indicated.

FIG. 4 depicts the partial genomic nucleotide sequences of exons 11 (SEQ ID NO: 42), 12 (SEQ ID NO: 43), 1 (SEQ ID NO:44), 13 (SEQ ID NO: 45), and 14 (SEQ ID NO: 46). Exon and partial intron sequences are shown in uppercase and lowercase, respectively. Putative translation start codon of exons 11 and 1 are underlined and bold. The 5' splice sites in exons 1a and 1b are indicated by vertical arrows.

FIG. 5A depicts the MOR-1 variants, as indicated at the top of the figure, which were transcribed in vitro, as described in Example 4, run on an SDS-PAGE gel and exposed to film.

FIG. 6 depicts the summary of the structures of the protein products of several MOR-1 splice variants.

FIGS. 10A–C depict the downregulation of exon 11-containing mRNA and exon 11 imunoreactivity by antisense. FIG. 10A depicts RT-PCR, performed as described in Example 7, of total RNA extracted from brains of mice that had received either antisense E11a, a mismatch E11a or saline. Parallel PCR with β2-microglobulin primers is shown as a loading control. FIG. 10B depicts immunostaining with an antibody to MOR-1 in the striatum. The regions used to determine the labeling density in the striatum and lateral septum are shown with boxes. FIG. 10C depicts the quantification of immunolabeling in the striatum, determined after subtracting out the background labeling, defined by that in the lateral septum, with a computer-assisted imaging system (Scion Image PC).

FIG. 12 depicts the summary of antisense mapping of the MOR-1 gene against opioid analgesia.

FIG. 13 depicts MOR-1ha (SEQ ID NO: 15)
FIG. 14 depicts MOR-1ia (SEQ ID NO: 16)
FIG. 15 depicts MOR-1ja (SEQ ID NO: 17)
FIG. 16 depicts MOR-1k (SEQ ID NO: 18)
FIG. 17 depicts MOR-1l (SEQ ID NO: 19)
FIG. 18 depicts MOR-1n (SEQ ID NO: 20)
FIG. 19 depicts MOR-1bV (SEQ ID NO: 21)
FIG. 20 depicts MOR-1bIII (SEQ ID NO: 22)
FIG. 21 depicts MOR-1bIV (SEQ ID NO: 23)
FIG. 22 depicts MOR-1o (SEQ ID NO: 24)
FIG. 23 depicts hMOR-1o (SEQ ID NO: 25)
FIG. 24 depicts hMOR-1p (SEQ ID NO: 26)
FIG. 25 depicts MOR-1m (SEQ ID NO: 27)
FIG. 26 depicts MOR-1Ha (SEQ ID NO: 28)
FIG. 27 depicts MOR-1Ia (SEQ ID NO: 29)
FIG. 28 depicts MOR-1Ja (SEQ ID NO: 30)
FIG. 29 depicts MOR-1L (SEQ ID NO: 31)
FIG. 30 depicts MOR-1K (SEQ ID NO: 32)
FIG. 31 depicts MOR-1M (SEQ ID NO: 33)
FIG. 32 depicts MOR-1N (SEQ ID NO: 34)
FIG. 33 depicts MOR-1BV (SEQ ID NO: 35)
FIG. 34 depicts MOR-1BIII (SEQ ID NO: 36)
FIG. 35 depicts MOR-1BIV (SEQ ID NO: 37)
FIG. 36 depicts MOR-1O (SEQ ID NO: 38)
FIG. 37 depicts hMOR-1O (SEQ ID NO: 39)
FIG. 38 depicts hMOR-1P (SEQ ID NO: 40)
FIG. 39 depicts MOR-1p (SEQ ID NO: 51)
FIG. 40 depicts MOR-1P (SEQ ID NO: 52)

BEST MODE FOR CARRYING OUT THE INVENTION

Figure 1:
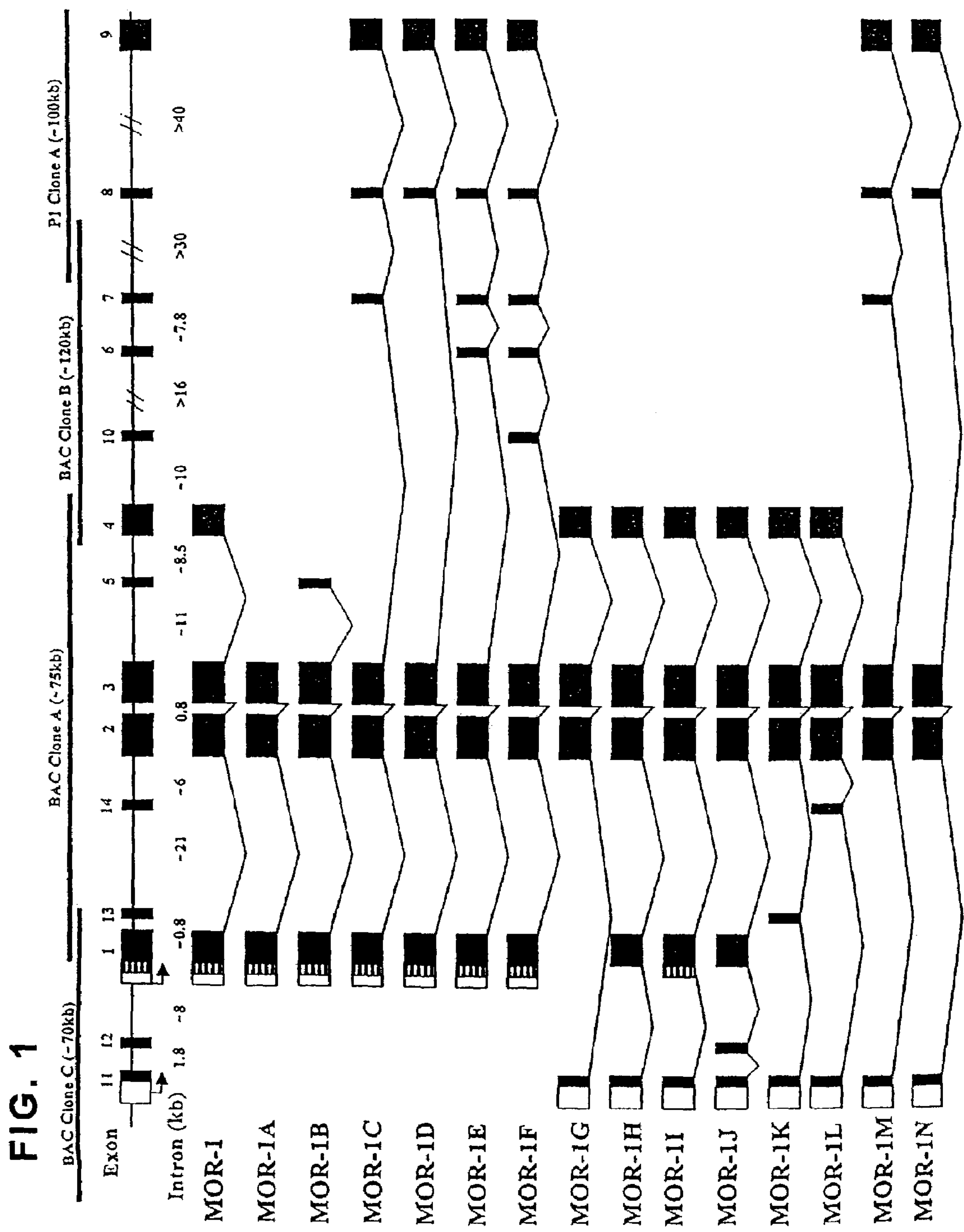
FIG. 1 depicts a schematic diagram of MOR-1 gene structure and alternative splicing. Coding exons are indicated by black boxes and 5' flanking regions by blank boxes. Introns and BAC clones are shown by light and heavy horizontal lines, respectively. The exons were numbered in the order in which they were discovered. Exon 1a (black) and exon 1b (striped) are portions of exon 1.

In view of the strong pharmacological evidence for distinct mu-opioid receptors, alternative splicing of the MOR-1 gene has been explored further. It has now been determined that the MOR-1 gene is subject to alternative splicing that produces novel splice variant forms of the mRNA and/or receptor. Fourteen new exons for the MOR-1 gene have been identified, which combine to yield at least fifteen novel MOR-1 splice variant polynucleotides. These splice variant polynucleotides and the polypeptides encoded thereby are potential targets for modulating morphine analgesia and opioid mediated ingestive responses.

The invention further encompasses isolated MOR-1 splice variant polynucleotides having the sequences of SEQ ID Nos: 15, 16, 17, 18, 19, 20, 21, 22, 23, 24, 25, 26 or 51. In addition to SEQ ID NOs 15, 16, 17, 18, 19, 20, 21, 22, 23, 24, 25, 26 or 51, the polynucleotide sequences can be any sequence of the appropriate genetic code to encode any of the MOR-1 splice variant polypeptides having the sequence of SEQ ID Nos: 28, 29, 30, 31, 32, 33, 34, 35, 36, 37, 38, 39, 40 or 52. Preferably, the polynucleotide is at least 15 consecutive nucleotides.

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially free of the materials with which it is associated in its native environment. By substantially free, is meant at least 50%, preferably at least 70%, more preferably at least 80%, and even more preferably at least 90% free of these materials.

The invention further comprises a complementary strand to the MOR-1 splice variant polynucleotide.

The complementary strand can be polymeric and of any length, and can contain deoxyribonucleotides, ribonucleotides, and analogs in any combination.

Hybridization reactions can be performed under conditions of different "stringency." Conditions that increase stringency of a hybridization reaction are well known. See for examples, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the MOR-1 splice variant polypeptides and functionally equivalent fragments thereof which may enhance, decrease or not significantly affect properties of the polypeptides encoded thereby. These functionally equivalent variants, derivatives, and fragments display the ability to retain MOR-1 activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

The invention further encompasses the MOR-1 splice variant polynucleotides contained in a vector molecule or an expression vector and operably linked to a promoter element if necessary.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors for translation of a polynucleotide encoding sequence. Also included are viral vectors.

The term "recombinant" means a polynucleotide of genomic cDNA, semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

Once introduced, the exogenous polynucleotide can be maintained within the cell as a non-integrated vector (such as a plasmid) or integrated into the host cell genome. Amplified DNA can be isolated from the host cell by standard methods. See, e.g., Sambrook et al. (1989). RNA can also be obtained from transformed host cell, or it can be obtained directly from the DNA by using a DNA-dependent RNA polymerase.

Expression vectors generally are replicable polynucleotide constructs that contain a polynucleotide encoding the polypeptide of interest. Herein, this means any of the MOR-1 splice variant polypeptides. For expression, one or more translational controlling elements are also usually required, such as ribosome binding sites, translation initiation sites and stop codons. These controlling elements (transcriptional and translational) can be derived from the MOR-1 gene, or heterologous (i.e., derived from other genes or other organisms). A number of expression vectors suitable for expression in eukaryotic cells including yeast, avian, and mammalian cells are well known in the art. One example of an expression vector is pcDNA3 (Invitrogen, San Diego, Calif.), in which transcription is driven by the cytomegalovirus (CMV) early promoter/enhancer. This vector also contains recognition sites for multiple restriction enzymes for insertion of an MOR-1 splice variant polypeptide of interest. Another example of an expression vector system is the baculovirus/insect system.

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. Typical selection genes either: (a) confer resistance to antibiotics or other toxins, e.g., ampicillin, neomycin, methotrexate; (b) complement auxotrophic deficiencies; or (c) supply critical nutrients not available for complex media. The choice of the proper marker gene will depend on the host cell, and appropriate genes for different hosts are known in the art. Vectors also typically contain a replication system recognized by the host.

Suitable cloning vectors can be constructed according to standard techniques, or selected from a large number of cloning vectors available in the art. While the cloning vector selected may vary according to the host cell intended to be used, useful cloning vectors will generally have the ability to self-replicate, may possess a single target for a particular restriction endonuclease, or may carry marker genes. Suitable examples include plasmids and bacterial viruses, e.g., pUC18, mp18, mp19, pBR322, pMB9, ColE1, pCR1, RP4, phage DNAs, and shuttle vectors such as pSA3 and pAT28. These and other cloning vectors are available from commercial vendors such as BioRad, Stratagene, and Invitrogen.

Figure 2:
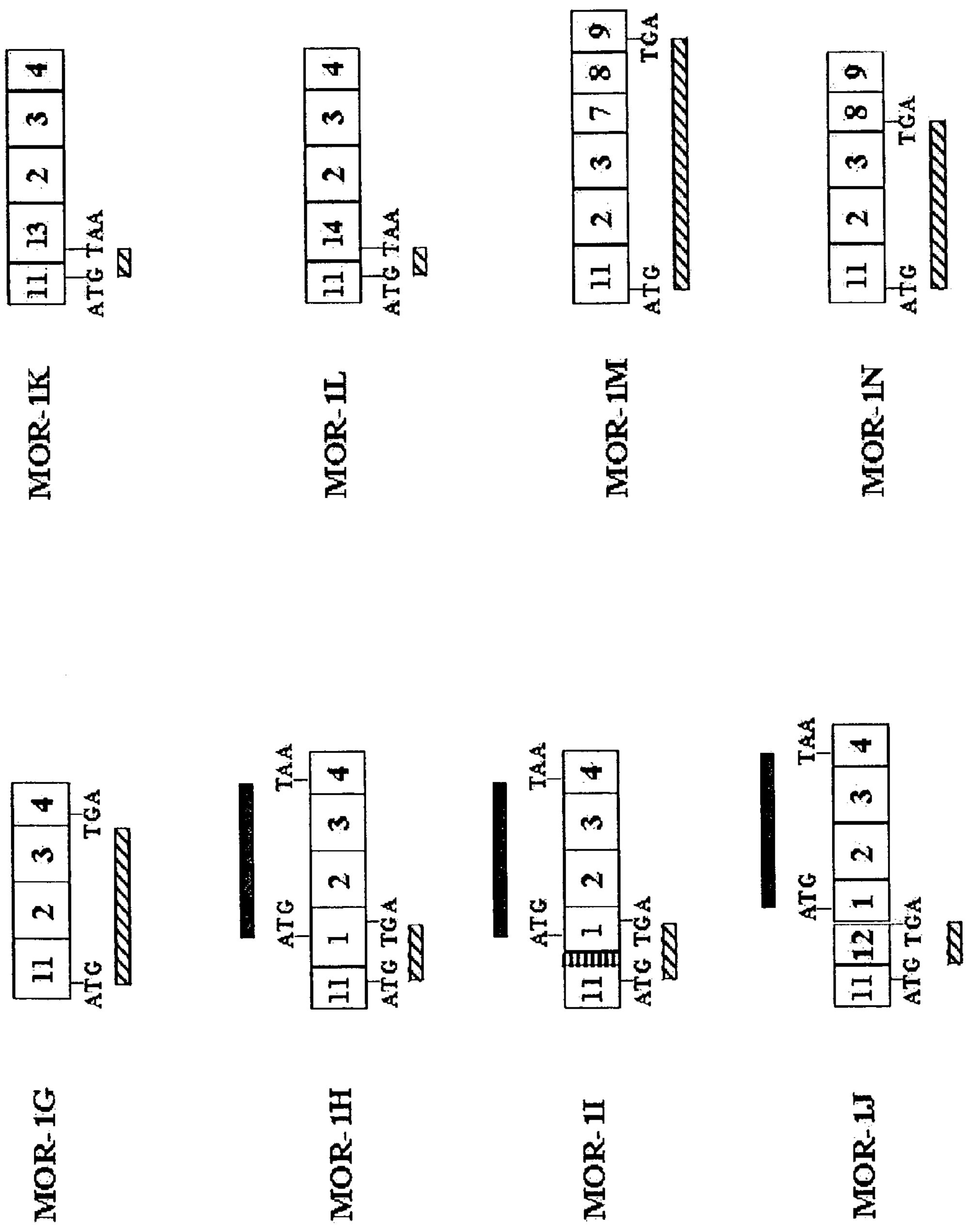
FIG. 2 depicts a schematic diagram of MOR-1 variant start and stop points in the exons indicated in the boxes. The translational start codon, ATG, and stop codons, TAA or TGA, are indicated on the top of the boxes for clones yielding the MOR-1 protein and under the boxes for other variants. Exon 1b (striped) is a portion of exon 1 (see MOR-1I variant).

The invention further encompasses an isolated polynucleotide, or a complementary strand thereto that hybridizes under stringent conditions, comprising at least 15 consecutive nucleotides of the MOR-1 splice variant polynucleotides depicted in FIG. 2 where the polynucleotide contains promoter elements.

The MOR-1 splice variant promoter elements are contained in exons 1a, 1b, and 1c or in any combination thereof. Promoter elements can control the level, tissue specificity, inducibility and, in gene clusters, the sequence of transcriptional activation and repression. Promoter elements include but are not limited to, enhancer sequences and repressor sequences.

The invention encompasses splice variant polypeptides. The exemplary MOR-1 splice variant polypeptides are composed of the amino acids indicated in FIG. 3. Polypeptide fragments comprising 5 amino acids, more preferably 7 amino acids, more preferably 15 amino acids, more preferably 25 amino acids, more preferably 50 amino acids and more preferably 75 amino acids, which are not the same as the known MOR-1 or MOR-1 variants are claimed herein and encompassed in the term "MOR-1 splice variant polypeptides".

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The MOR-1 splice variant polypeptides retain MOR-1 activity. To "retain MOR-1 activity" is to have a similar level of functional activity as the MOR-1 polypeptide. FIG. 3. This activity includes, but is not limited to, immunologic and pharmacologic activity.

The "immunologic activity" is binding to anti-opioid receptor antigen binding fragments. The antigen binding fragments can be any functional antibody, fragment or derivative thereof, including, but not limited to, whole native antibodies, bispecific antibodies, chimeric antibodies, Fab, F(ab')2, single chain V region fragments (scFv), and fusion polypeptides comprising an antigen binding fragment fused to a chemically functional moiety.

The "pharmacologic activity" is activation or deactivation of the MOR-1 splice variant polypeptides upon binding of agonists or antagonists.

The invention further encompasses MOR-1 splice variant polypeptide homologs. A "homolog" is a polypeptide similar in amino acid sequence to other polypeptides among a single species or, a "homolog" in evolution is a polypeptide similar in amino acid sequence to other polypeptides in different species because they have been inherited from a common ancestor. Preferably, homologs of the present invention are human homologs.

Isolation of MOR-1 splice variant human homolog cDNAs can be carried out by any method known in the art. For instance, methods analogous to the isolation of the mouse MOR-1 splice variants described herein (see Example 2). Using primers corresponding to the human MOR-1 gene and a Marathon-Ready human cDNA Library to carry out reactions according to the Marathon cDNA Amplification Kit (Clontech), human MOR-1 splice variants can be obtained. Alternatively, screening of human cDNA libraries with probes corresponding to mouse MOR-1 splice variant sequences can be carried out at reduced stringency to identify human MOR-1 splice variant cDNAs.

The invention further encompasses the MOR-1 splice variant polypeptides in a heterodimeric or homodimeric form. A "heterodimer" is a protein made up of more than one kind of polypeptide. A "homodimer" is a protein made up of more than one kind of polypeptide.

Pharmaceutical compositions and treatment modalities can be detected by the methods of this invention. The MOR-1 splice variant polypeptide fragments and MOR-1 splice variant nucleic acid sequences can be used in screening for compositions that alter variant activity. Compositions that selectively regulate the MOR-1 splice variant polypeptide fragments or selectively modulate physiological processes can be identified.

The invention further encompasses methods of screening compositions for opioid activity by obtaining a control cell that does not express a recombinant opioid receptor and obtaining a test cell that is the same as the control cell except that it expresses a recombinant MOR-1 splice variant polypeptide, contacting the control cell and test cell with an amount of an opioid sufficient to exert a physiologic effect, separately measuring the physiologic effect of the composition on the control cell and test cell and comparing the physiologic effect of the composition to the physiologic effect of the opioid, where determination of a physiologic effect of the composition is expressed relative to that of the opioid.

The invention further comprises a method of screening compositions for opioid activity by obtaining a control polypeptide that is not a recombinant opioid receptor and obtaining a test polypeptide that is a recombinant MOR-1 splice variant polypeptide, contacting a composition with the control polypeptide and the test polypeptide, contacting the test polypeptide with an amount of an opioid sufficient to measurably bind the test polypeptide, measuring the binding of the composition and the opioid and comparing the test polypeptide binding of the composition to that of the opioid, where determination of binding of the composition is expressed relative to that of the opioid.

The invention further encompasses a method of screening compositions for differential opioid activity by obtaining a first test polypeptide that is an MOR-1 splice variant polypeptide and contacting it with a composition and obtaining a second test polypeptide that is an MOR-1 splice variant polypeptide, measuring the binding of the composition to the first and second test polypeptides, and comparing the binding of the composition and the first test polypeptide to that of the second test polypeptide where differential activity is expressed as a ratio of the two binding affinities.

The compositions screened include, but are not limited to, chemical, synthetic combinatorial libraries of small molecule ligands, eukaryotic whole cell lysates or extracts, media conditioned by cultured eukaryotic cells, natural products and extracts thereof.

The opioid can be, but is not limited to, morphine, methadone, etorphine, levorphanol, fentanyl, sufentanil, [D-Ala$^2$, MePhe$^4$, Gly(ol)$^5$]enkephalin (DAMGO), pentazocine, ethylketocyclazocine, bremazocine, spiradoline, [D-Ser$^2$, Leu$^5$]enkephalin-Thr$^6$ (DSLET), Met-enkephalin, Leu-enkephalin, β-endorphin, dynorphin A, dynorphin B, α-neoendorphin analogs and combinatorial chemistry products thereof.

The physiological effect can be measured by any method known in the art such as changes in the levels of neuroendocrine hormones, including, but not limited to prolactin, growth hormone, gonadotropin-releasing hormone, adrenocorticotropin, corticotropin-releasing factor, luteinizing hormone, follicle stimulating hormone, testosterone or cortisol. The physiological effect can also be measured by changes in the levels of neurotransmitters, including but not limited to, acetylcholine or dopamine.

Activation of an MOR-1 receptor, and likely, the MOR-1 splice variant polypeptides, stimulates a variety of physiological responses, including analgesia, depression of gastrointestinal motility and respiration, and alterations of the immune, endocrine and autonomic nervous system. Compositions that regulate the activity of the MOR-1 receptor and/or the MOR-1 splice variant polypeptides can elicit responses that have therapeutic effects. The invention is useful in diagnosis, treatment, design and screening of novel reagents. Screening of compounds can result in obtaining those with differential or selective activity. That is, for instance, certain compositions can retain analgesic effects but do not affect peristaltic activity and thus do not cause constipation. Conversely, compositions that lack analgesic effects but affect peristaltic activity would be useful in treating chemotherapy and HIV patients. Other applications relating to the side effects of opiates can be readily envisaged by one of skill in the art.

The invention further encompasses a method for regulating morphine analgesia in a subject by altering the amount of MOR-1 splice variant polypeptide activity in the subject. Activity can be regulated by administering antigen binding fragments, agonists, antagonists or small molecule ligands to a subject in an amount and duration sufficient to regulate morphine analgesia. The antigen binding fragment, agonist, antagonist or small molecule ligand is directed to an MOR-1 splice variant.

Activity can also be regulated by administering a DNA plasmid vector containing an MOR-1 splice variant polynucleotide. The DNA plasmid vector thereby expresses an MOR-1 splice variant polynucleotide in a subject in an amount and a duration sufficient to regulate morphine analgesia. Activity can also be regulated by administering an antisense nucleic acid complementary to an MOR-1 splice variant polynucleotide, thereby blocking gene expression in a subject in an amount and a duration sufficient to regulate morphine analgesia.

Agonists and antagonists of MOR-1 splice variant polypeptide activity can include but are not limited to, morphine, methadone, etorphine, levorphanol, fentanyl, sufentanil, [D-Ala$^2$, MePhe$^4$, Gly(ol)5]enkephalin (DAMGO), butorphanol, naloxone, naltrexone, D-Phe-Cys-Tyr-D-Trp-Orn-Thr-Pen-Thr-$NH_2$ (CTOP), diprenorphine, β-funaltrexamine, naloxonazine, nalorphine, pentazocine, nalbuphine, benzoylhydrazone, bremazocine, ethylketocyclazocine, trans-(−)-3,4-dichloro-N-methyl-N-[2-(1-pyrrolidinyl)cyclohexyl]benzeneacetamide (also known as U50488), (5-alpha,7-alpha,8-beta)-(+)-N-methyl-N-[7-(1-pyrrolidinyl)-1-oxaspiro(4,5)dec-8-yl]-benzeneacetamide (also known as U69593), spiradoline, naltrindole, [D-Pen$^2$, D-Pen-$^5$]enkephalin (DPDPE), [D-Ala$^2$,Glu$^4$]deltorphin, [D-Ser$^2$,Leu$^5$]enkephalin-Thr$^{\neq}$(DSLET), Met-enkephalin, Leu-enkephalin, β-endorphin, dynorphin A, dynorphin B, α-neoendorphin and derivatives such as those produced by combinatorial chemistry and their mixtures and physiologically acceptable salts thereof.

A "subject" is a vertebrate, preferably a mammal, and more preferably a human. Mammals include but are not limited to humans, farm animals, sport animals, and pets.

The invention further encompasses antigen binding fragments specific for an MOR-1 splice variant polypeptide. According to the invention, an MOR-1 splice variant polypeptide can be used as an immunogen to generate antigen-binding fragments which immunospecifically bind the immunogen.

Production of antigen binding fragments such as polyclonal antibodies can be carried out by any method known in the art. Various host animals can be immunized by injection with the immunogen, including but not limited to rabbits, mice and rats. Various adjuvants can be used to increase the immunological response, depending on the host species, and including but not limited to Freund's (complete or incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

For preparation of antigen binding fragments such as monoclonal antibodies, any technique that provides for the production of antibody molecules by continuous cell lines in culture can be used. Examples of such techniques include the original hybridoma technique (Kohler and Milstein (1975) Nature 256:495) as well as the trioma technique, the human B-cell hybridoma technique (Kozbor et al. (1983) Immunol. Today 4:72), and the EBV hybridoma technique to produce human monoclonal antibodies. Cole et al. (1985) in Monoclonal Antibodies and Cancer Therapy, Alan R. Liss, Inc., pp. 77–96. Monoclonal antibodies can also be produced in germ-free animals utilizing known technology. PCT/US90/02545. Human antibodies can be obtained using human hybridomas (Cote et al. (1983) Proc. Natl. Acad. Sci. U.S.A. 80:2026), or by transforming human B cells with EBV virus in vitro. Cole et al. (1985). Techniques developed for the production of "chimeric antibodies" by splicing the genes from a mouse antibody molecule specific for MOR-1 splice variants together with genes from a human antibody of appropriate biological activity can be used. Morrison et al. (1984) Proc. Natl. Acad. Sci. U.S.A. 81:6851; Neuberger et al. (1984) Nature 312:604; and Takeda et al. (1985) Nature 314:452.

Techniques described for the production of single chain antibodies (U.S. Pat. No. 4,946,778) can be adapted to produce MOR-1 splice variant polypeptide-specific single chain antibodies. Techniques described for the production of Fab expression libraries (Huse et al. (1989) Science 246: 1275) can be utilized, allowing rapid and easy identification of monoclonal Fab fragments specific for an MOR-1 splice variant polypeptide.

Antibody fragments that contain the idiotype of the molecule can be generated by known techniques. For example, such fragments include but are not limited to: the F(abl), fragment which can be produced by pepsin digestion of the antibody molecule; the Fab' fragments which can be generated by reducing the disulfide bridges of the F(abl) fragment, the Fab fragments which can be generated by treating the antibody molecule with papain and a reducing agent, and Fv fragments.

Single chain V region fragments ("scFv") can also be produced. Single chain V region fragments are made by linking L (light) and/or H (heavy) chain V (variable) regions by using a short linking peptide. Bird et al. (1988) Science 242:423. any peptide having sufficient flexibility and length can be used as a linker in a scFv. Usually the linker is selected to have little to no immunogenicity. An example of a linking peptide is $(GGGGS)_3$ SEQ ID NO: 54), which bridges approximately 3.5 nm between the carboxy terminus of one V region and the amino terminus of another V region. Other linker sequences can also be used, and can provide additional functions, such as for attaching a drug or solid support.

All or any portion of the H or L chain can be used in any combination. Typically, the entire V regions are included in the scFv. For instance, the L chain V region can be linked to the H chain V region. Alternatively, a portion of the L chain V region can be linked to the H chain V region or a portion thereof. Also contemplated are scFvs in which the H chain V region is from H11, and the L chain V region is from another inmunoglobulin. It is also possible to construct a biphasic, scFv in which one component is an MOR-1 splice variant polypeptide and another component is a different polypeptide, such as a T cell epitope.

The scFvs can be assembled in any order, for example, $V_H$-linker-$V_L$ or $V_L$-(linker)-$V_H$. There may be a difference in the level of expression of these two configurations in particular expression systems, in which case one of these forms may be preferred. Tandem scFvs can also be made, such as (X)-(linker)-(X)-(linker)-(X), in which X are MOR-1 splice variant polypeptides, or combinations of MOR-1 splice variant polypeptides with other polypeptides. In another embodiment, single chain antibody polypeptides have no linker polypeptide, or just a short, inflexible linker. Exemplary configurations include $V_L$-$V_H$ and $V_H$-$V_L$. The linkage is too short to permit interaction between $V_L$ and $V_H$ within the chain, and the chains form homodimers with a $V_L/V_H$ antigen-binding site at each end. Such molecules are referred to in the art as "diabodies".

ScFvs can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect or mammalian cells, or prokaryotic, such as *Escherichia coli*, and the protein expressed by the polynucleotide can be isolated using standard protein purification techniques.

A particularly useful system for the production of scFvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.), described above.

The following examples are provided to illustrate but not limit the claimed invention. The examples demonstrate isolation and characterization of MOR-1 splice variants, and are representative of the methods employed for all claimed MOR-1 splice variants.

EXAMPLE 1

Identification and Cloning of Exon 11

Using a modified 5'-Rapid Amplification of cDNA Ends (RACE) strategy, a novel exon (exon 11) sequence (SEQ ID NO: 42) that was directly spliced to exon 2 was isolated. Total RNA's extracted from CXBK and C57 Black/6 mouse brains were reverse-transcribed with random hexamers and oligo dT. The first strand cDNAs then were hybridized with a 5' biotinylated sense primer designed from exon 3, having the sequence 5'CATGGTACTGGGAGAACCTGCTCA3' (SEQ ID NO: 1). The hybridized cDNA was captured and purified with magnetic beads covalently coupled to streptavidin (Dynabeads M280 Streptavidin). The purified cDNA was then ligated using a T4 RNA ligase with an adapt primer having the sequence 5'CCCTTCTGTCGTCTTCTCGCAGCCGTA3' (SEQ ID NO: 2) that had been modified by adding a phosphate group at the 5' end and an amine group at the 3' end to obtain an efficient unidirectional ligation. A nested polymerase chain reaction (PCR) was performed with the ligated cDNAs as template. The first round PCR with a sense primer, having the sequence 5'TACGGCTGCGAGAAGACGACAGAAGGG3' (SEQ ID NO: 3), derived from the adapt primer, and an antisense primer having the sequence 5'CCGGCATGATGAAGGCGAAGATGA3' (SEQ ID NO: 4) from exon 3 produced no visible bands. The first round PCR products were used as templates for a second round PCR with the same sense primer and a nested antisense primer having the sequence 5'CGGAAATCCAGGGCCTTGACCGG3' (SEQ ID NO: 5) from exon 2. Several bands were obtained and cloned into pCRII-TOPO vector (Invitrogen). Sequence analysis of one of the clones, 431117, indicated that a new 184 bp sequence was linked to the 5' end of exon 2. The new sequence, assigned as exon 11 (SEQ ID NO: 42), predicted a novel peptide of 27 amino acids in-frame with the exon 2 sequence present in MOR-1.

EXAMPLE 2

Identification and Cloning of MOR-1g, MOR-1ha, MOR-1ia MOR-1ja, MOR-1k, MOR-1l, MOR-1m and MOR-1n cDNA Sequences To determine whether additional variants also contained exon 11, reverse transcription polymerase chain reaction (RT-PCR) with two sense primers designed from exon 11, sense primer E11A, 5'CCTCCAGGCTCATTTCAGAGA G3' (SEQ ID NO: 6) and sense primer E11B, 5'GGCGCGG-GATCTGGGCCGATGATGGAAGCTTTCTCTAAGTCT GCATTC3' (SEQ ID NO: 7), two antisense primers from exon 4, antisense primer E4A, 5'CCAGGAAACCAGAGC-CTCCCACAA3' (SEQ ID NO: 8) and antisense primer E4B, 5'GGCGTGGGACCCAGTTAGGGCA3' (SEQ ID NO: 9) and two antisense primers from exon 9, antisense primer E9A, 5'GAAAGGCATCTTCCCTCTCGCTGT3' (SEQ ID NO: 10) and antisense primer E9B, 5'CCACACT-GCTCACCAGCTCATCCC3' (SEQ ID NO: 11) was used. Exon 4 is contained within MOR-1 while exon 9 is contained within MOR-1c, MOR-1d, MOR-1e and MOR-1f. No known variants contain both exon 4 and 9. The primers were used in nested-PCRs with the first-strand cDNA reverse-transcribed from mouse brain total RNA as templates. The PCR fragments were subcloned into pCRII-TOPO and sequenced in both directions with appropriate primers. Eight full length cDNAs containing exon 11 were identified (FIG. 1) and named MOR-1g, MOR-1ha (SEQ ID NO 15), MOR-1ia (SEQ ID NO 16), MOR-1ja (SEQ ID NO 17), MOR-1k (SEQ ID NO 18), MOR-1l (SEQ ID NO 19), MOR-1m and MOR-1n (SEQ ID NO 20).

Several of these variants were particularly interesting since they also contained portions of exon 1 (FIGS. 1 and 2). These portions included the translation start point, but not the promoter regions described for the original MOR-1. Ko et al. (1997); Min et al. (1994); and Liang et al. (1995). MOR-1ha contained a 415 bp fragment of exon 1 (exon 1a) inserted between exons 11 and 2. In addition to the 415 bp insertion, MOR-1ia contained an additional 174-bp insertion (exon 1b) located immediately upstream of the 415-bp. MOR-1ja had a novel 129 bp insertion (exon 12) between exon 11 and the 415 bp of exon 1. Neither the 415 bp nor the 174 bp sequence from exon 1 contained promoter regions from the originally described MOR-1 (Min et al. (1994); Ko et al. (1997); Liang et al. (1995); Liang and Carr (1996); Mayer et al. (1996); Choe et al. (1998); Andria and Simon (1999); Kraus et al. (1995)), and their 5' splice acceptor sites were located at 131-bp and 305-bp upstream, respectively, of the ATG translation start codon of MOR-1 (FIG. 2). There was a 149-bp (exon 13) and a 108-bp (exon 14) insertion between exons 11 and 2 in MOR-1k and MOR-1l, respectively. Both MOR-1m and MOR-1n had similar exon compositions as MOR-1c and MOR-1d (Pan et al. (1999)), respectively, except that exon 1 was replaced by exon 11.

There were two methionine residues in a row predicted from exon 11. The first methionine was arbitrarily chosen as a potential translation start codon. Based upon this assumption, sequence analysis of exon 11 predicted 27 amino acids. In MOR-1g, the start codon in exon 11 was in the same reading-frame as exons 2, 3 and 4 as used in MOR-1 (FIG. 2), resulting in a new variant in which the 96 amino acids encoded by exon 1 in MOR-1 were replaced by the 27 amino acids of exon 11 (SEQ ID NO 53; FIG. 3). A similar relationship existed between MOR-1M (SEQ ID NO 33; exons 11/2/3/7/8/9) and MOR-1C and between MOR-1N (SEQ ID NO 34; 11/2/3/8/9) and MOR-1D. Exon 1 has a predicted transmembrane region encoded by the last 25 amino acids of the exon. However, analysis of the 27 amino acids encoded by the exon 11 did not predict a transmembrane region, implying that MOR-1G, MOR-1M and MOR-1N may contain only the six transmembrane regions encoded by exons 2 and 3.

In MOR-1Ha (SEQ ID NO 28), MOR-1Ia (SEQ ID NO 29) and MOR-1Ja (SEQ ID NO 30), predicted translations became complicated since there were two potential start codons, one in exon 11 and one in exon 1. FIGS. 2 and 3. The start codon from exon 1 would yield a protein identical to MOR-1, although it would be under the control of a different promoter. The start codon in exon 11 predicted short peptides with 84 amino acids for MOR-1Ha, with 48 amino acids for MOR-1Ia or with 35 amino acids for MOR-1Ja due to early termination of translation within exons 1a, 1b and 12, respectively. FIGS. 2 and 3. Similarly, the exon 11 start codon would yield truncated peptides of 39 amino acids for MOR-1L (SEQ ID NO 31) and 41 amino acids for MOR-1K (SEQ ID NO 32) for the other two variants containing exon 11. FIGS. 2 and 3. Sequence analysis from the cDNA indicated that none of these truncated peptides contained a transmembrane domain.

EXAMPLE 3

Mapping, Isolation and Analysis of Genomic Clones

Since exon 11 was not present in the genomic clones containing exons 1 through 10 previously isolated (Pan et al. (2000); Pan et al. (1999)), an additional clone of approximately 70 kb was identified by PCR from a mouse genomic BAC library with exon 1 primers (GenomeSystems, Inc.). Analyses of the new clone, BAC clone C, by Southern blotting, long PCR and sequencing with appropriate probes and primers indicated overlap between BAC clone C and BAC clone A. BAC clone C contained exons 11, 12, 13 and 1, but not exons 2 through 10 that are further downstream. In BAC clone C, exon 11 mapped approximately 10 kb upstream of exon 1. FIG. 1.

To establish the gene structure of MOR-1 with the novel exon sequences, a mouse BAC genomic library clone was screened using exon 1 primers and isolated BAC clone C, which was approximately 70 kb. BAC clone C contained exons 11 (SEQ ID NO 42), 12 (SEQ ID NO 43), 1 (SEQ ID NO 44) and 13 (SEQ ID NO 45) and overlapped with the BAC clone A in the region containing exons 1 and 13. Exons 11 and 12 were approximately 10 kb and 8 kb upstream, respectively, of exon 1. Exons 13 (SEQ ID NO 45) and 14 (SEQ ID NO 46) were located approximately 1 kb and 22 kb downstream of exon 1, respectively. Partial sequences of BAC clones C and A indicated that gene sequences of the exons were identical to those identified in the original cDNAs and that all the exons had flanking sequences consistent with consensus splice junctions (FIG. 4). The splice sites of exon 1 were also in agreement with the GT/AG rule. The MOR-1 gene now contains at least 14 exons spanning more than 250 kb and their combination by alternative splicing yields 15 variants.

EXAMPLE 4

In Vitro Translation and Identification of the Variants

Figure 5:
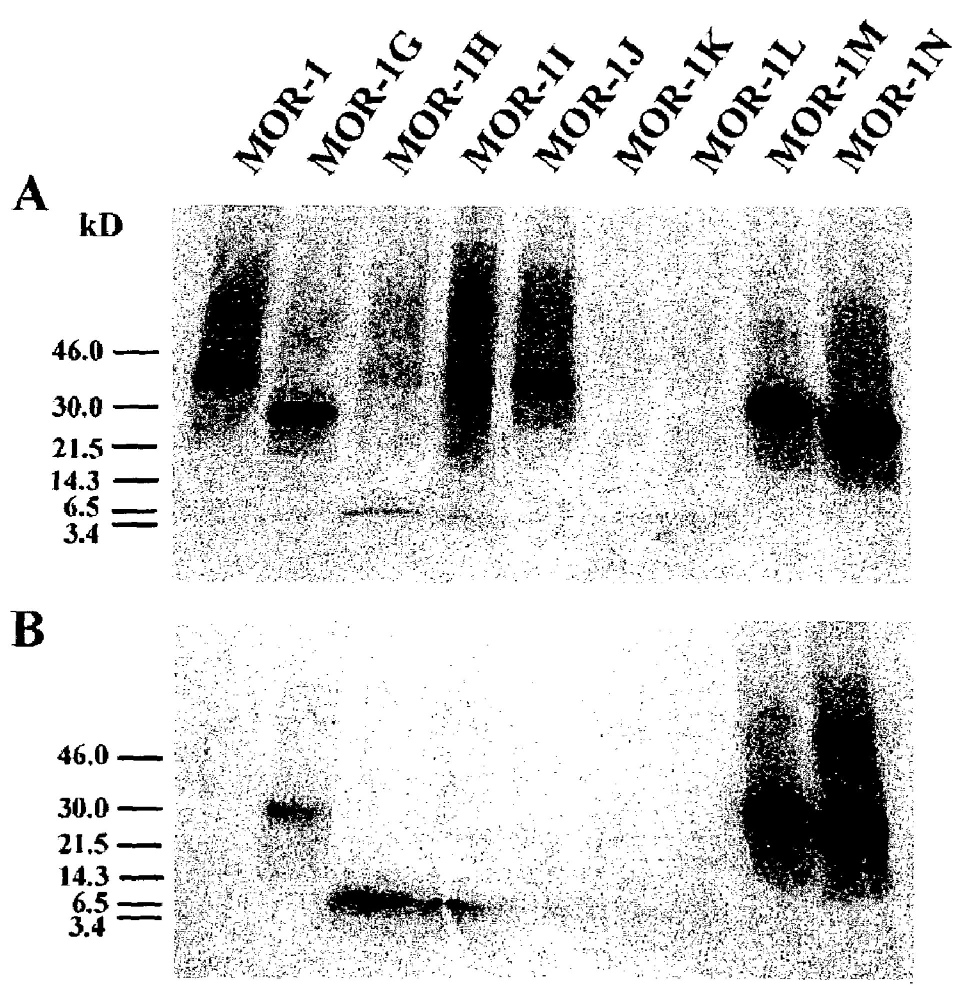
FIGS. 5A and B depict the results of the in vitro translation (A) and immunoprecipitation (B) experiments.
FIG. 5B depicts SDS-PAGE analysis followed by exposure to film, of the MOR-1 variants following in vitro translation and immunopurification by an antiserum generated from the predicted coding sequence of exon 11, as described in Example 4.

In vitro translation and immunoprecipitation studies confirmed the ability of the two start codons in exons 11 and 1 to generate proteins. FIGS. 5 and 6. The full length cDNA clones in the pCRII-TOPO or pcDNA3.1 vectors were in vitro transcribed with either T7 polymerase or SP6 polymerase and translated in the presence of 0.04 mCi of [$^{35}$S]methionine (1000 Ci/mmol, New England Nuclear Corp.) with a TNT coupled transcription/translation kit (Promega). A rabbit polyclonal antiserum (27-906) against a 22-residue peptide, H-MEAFSKSAFQKLRQRDGN-QEGC-NH2 (SEQ ID NO 41), from the predicted amino acid sequence of exon 11 was generated by Multiple Peptide Systems. The peptide conjugation, immunization protocol, and immunoaffinity antibody purification were described previously. Abbadie et al. (2000c). The extra cysteine residue was added to the terminal of the peptide for the purpose of conjugation with Keyhole Limpet Hemocyanin (KLH). The translation products were incubated with the purified antibody (1:50 dilution) in a dilution buffer (10 mM Tris/HCl, 150 mM NaCl, 1 mM EDTA and 0.1% Triton X-100) for overnight at 4° C. The protein G-Sepharose (Pharmacia) was then added and the incubation extended for another 4 hr at 4° C. The Sepharose was pelleted by centrifugation, washed twice with the dilution buffer and resuspended in SDS gel sample buffer (62.5 mM Tris/HCl, pH 6.8, 2.3% SDS, 5% β-mercaptoethanol, 10% glycerol). The translation products and their immunoprecipitated products were separated by 4–20% gradient SDS-PAGE, the gel then was treated with Amplify (Amersham), dried and exposed to Kodak BioMax MF film.

MOR-1g, MOR-1m and MOR-1n all have exon 11 joined directly to exon 2. In vitro translation of these variant cDNAs produced single bands in SDS-PAGE of approximately 30 kDa for MOR-1G and MOR-1N and 33 kDa for MOR-1M. MOR-1K and MOR-1L, which contain either exon 13 or 14, respectively, between exon 11 and exon 2 yielded bands of 4 kDa. FIGS. 2 and 5A. MOR-1Ha, MOR-1Ia and MOR-1Ja contain both the exon 11 and exon 1 start codons. In vitro translation of these three variants gave major bands of approximately 40 kDa. However, small bands under 10 kDa for MOR-1Ha, MOR-1Ia and MOR-1Ja were also observed. The MOR-1Ha band was most prominent, followed by MOR-1a. The band from MOR-1Ja was quite faint, although reproducible with several replications. The relative quantities of the products generated from the two start codons in the in vitro translation system varied among the clones. In MOR-1Ha, the small band predominated over the large one corresponding to MOR-1, while in MOR-1Ia, both bands appeared equal. However, the large MOR-1 band was predominant in MOR-1Ja. The different translation efficiencies of the variants implied preferential usage of the two translation start codons in the different cDNAs in the in vitro translation system.

Although all the new variants contained exon 11, it presumably was not translated in all proteins. To determine which translated bands contained the exon 11 amino acid sequence, the in vitro transcribed products were immunoprecipitated using an antiserum generated from the predicted sequence of the translated portion of exon 11. FIG. 5B. The product of the MOR-1 clone was not immunoprecipitated, providing an important control. All of the other variants had one band precipitated, although the intensities of some of the smaller molecular weight bands were faint. In vitro translation of MOR-1ha, MOR-1ia and MOR-1ja generated two bands each, with the larger one presumably identical to the product of the MOR-1 clone. The antiserum immunoprecipitated the smaller molecular weight bands, as predicted, but not the larger ones that corresponded to the same protein generated by the MOR-1 clone.

EXAMPLE 5

Expression Patterns of the MOR-1 Variants

To determine the lengths of the mRNA transcripts encoding the MOR-1 variants, Northern blot analysis was performed as described previously. Pan et al. (2000); and Pan et al. (1999). Total RNA was isolated from mouse brain using the guanidinium thiocyanate phenol-chloroform extraction method. Samples of total brain RNA (50 μg/lane) were separated on a 0.8% formaldehyde agarose gel, and transferred to a Gene Plus membrane. The membrane was hybridized with $^{32}$P-labeled fragments amplified by PCR with appropriate primers.

Figure 7:
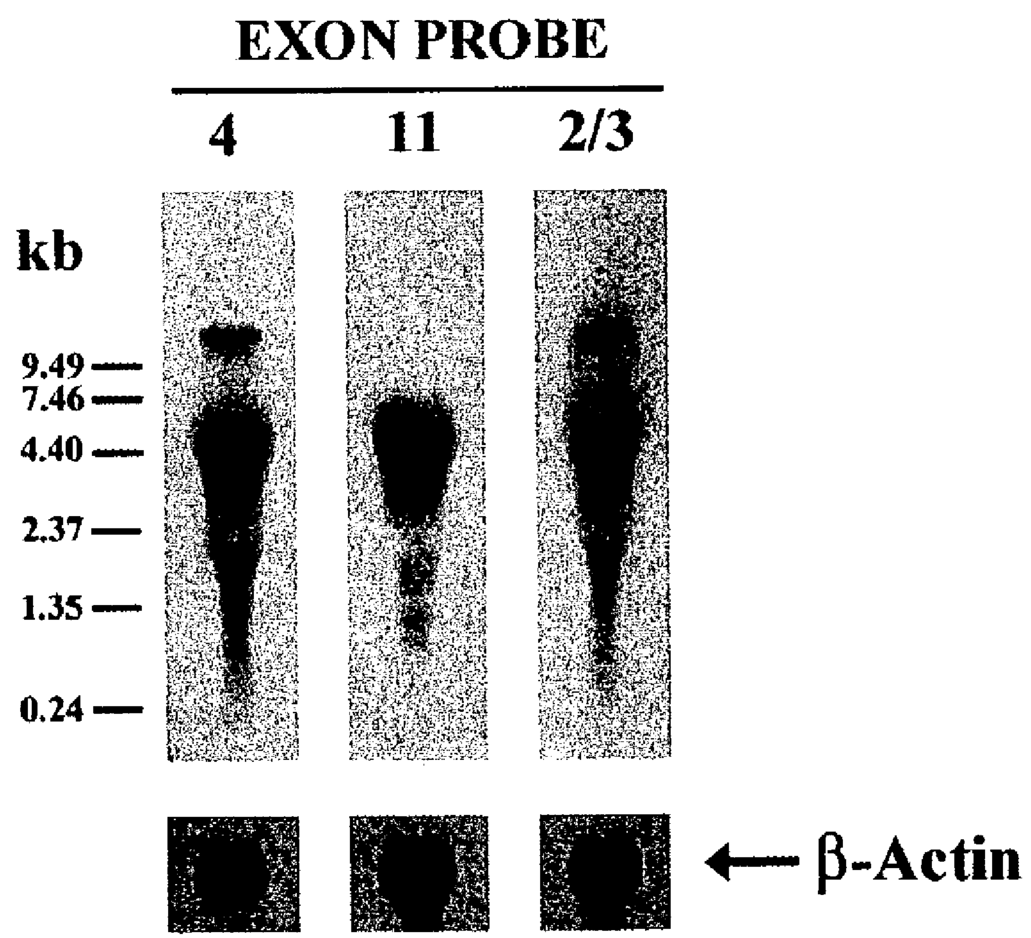
FIG. 7 depicts a Northern blot performed with total RNA from mouse brain using a 121-bp exon 4 probe and a 141-bp exon 11 probe, as described in Example 5. β-Actin was included as a loading control.

Northern blot analysis established the relative size and abundance of the new mRNAs in mouse brain. An exon 11 probe detected a diffuse band, ranging in size from ~4 to 7 kb, that was clearly different from the single transcript of ~12 kb revealed by an exon 4 probe (FIG. 7) and from the band of approximately 6–9 kb seen with a probe from exons 7/8/9. Pan et al. (1999). The abundance of the exon 11-containing mRNA was clearly far lower than the exon 4-containing species. Similar differences have been observed when comparing Northern blots with exon 11 and exon 1 probes. No significant signals were detected using exon 12, or 13 or 14 probes in the same assay, which may simply reflect their low abundance and their short length.

Figure 8:
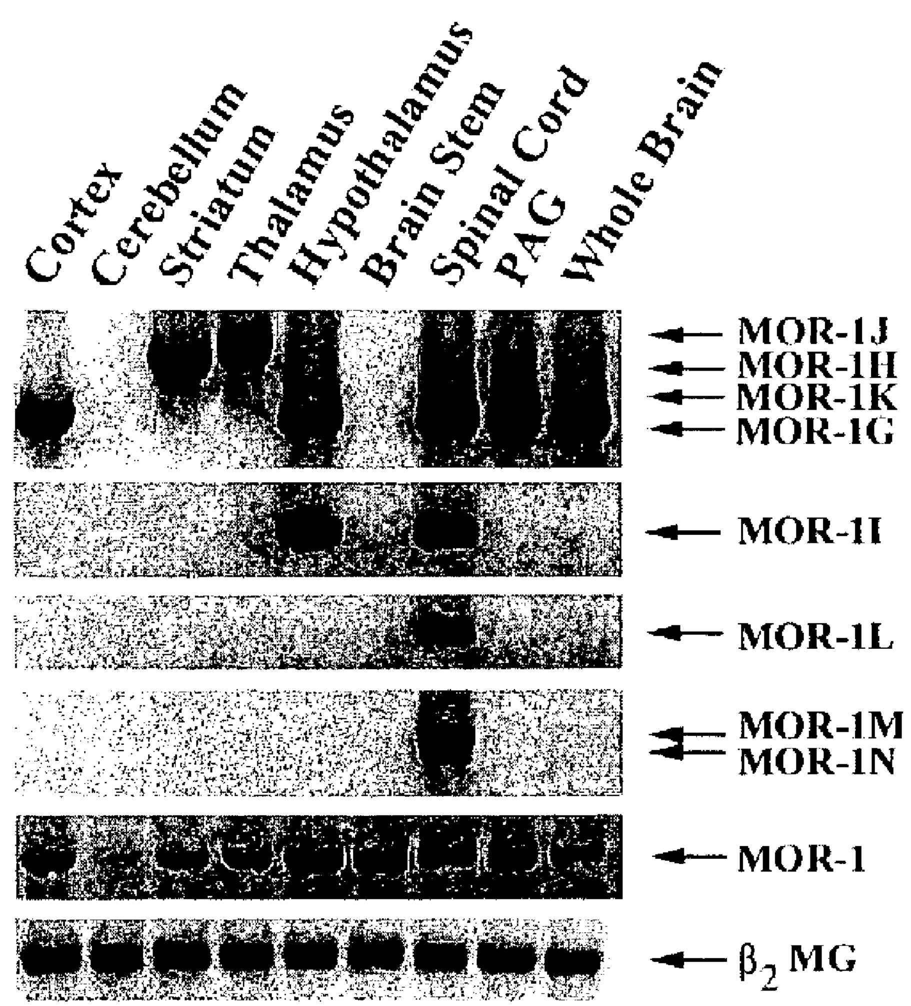
FIG. 8 depicts the regional distributions of the indicated MOR-1 variants examined by RT-PCR on the indicated brain regions, as described in Example 5. Parallel PCR with β2-microglobulin primers is shown as a loading control.

The regional distribution of mRNA expression was examined next using RT-PCR. FIG. 8. Total RNA was isolated from different mouse brain regions as described, and reverse-transcribed by a SuperScript II Reverse Transcriptase (GIBCO) with either antisense E4A (SEQ ID NO 8) or antisense E9A (SEQ ID NO 10). The first-strand cDNAs were then used as templates in the first-round PCRs with the sense primer E11A (SEQ ID NO 6) and the antisense primer E4A (SEQ ID NO 8) or E9A (SEQ ID NO 10). Since no visible bands on agarose gel were observed, second-round PCRs were performed using the first-round PCRs as templates with the sense primer E11B (SEQ ID NO 7) and antisense primer E4B (SEQ ID NO 9) for MOR-1g, MOR-1ha, MOR-1ja and MOR-1k, or E9B (SEQ ID NO 11) for MOR-1m and MOR-1n. The sense primer E11B (SEQ ID NO 7) was paired with an antisense E1A, 5'GTGGAACCAGAGAAGAGCGGCAGG3' (SEQ ID NO 12), or an antisense E14A, 5'CTTTGTGGTGGTCGACCAGTTGCC3' (SEQ ID NO 13), in the second-round PCRs to amplify MOR-1ia and MOR-1l, respectively. A sense primer E1A (SEQ ID NO 12), designed from the exon 1b, 5'GGACGCTCAGACGTTCCATTCTGC3' (SEQ ID NO 14), and antisense E4A (SEQ ID NO 8) were used to amplify MOR-1 with the same templates. The agarose gel was stained with ethidium bromide and photographed with Kodak DC 120 Digital Camera/Imaging System. The predicted sizes of the PCR products for MOR-1g, MOR-1ha, MOR-1ia, MOR-1ja, MOR-1k, MOR-1l, MOR-1m and MOR-1n are 1,025 bp, 1,440 bp, 269 bp, 1,569 bp, 1,174 bp, 206 bp, 1,171 bp and 1,082 bp, respectively. Each band was extracted from agarose gel, subcloned into pCRII-TOPOII vector and confirmed by sequencing. RNA loading was estimated by a parallel PCR with a pair of β-microglobulin ($β_2$MG) primers (ClonTech).

The MOR-1 transcript driven by the original exon 1 promoter was observed after the first-round PCR and was expressed in all regions with relatively equal abundance, except for lower levels in the cerebellum. FIG. 8. The expression of all the other variants derived from the exon 11 promoter were detected only in the second-round of PCR, consistent with the lower levels of these mRNAs seen with Northern blots. However, the distribution of the variant mRNAs was interesting. MOR-1g was highly expressed in the cortex, hypothalamus, PAG and spinal cord, but it was not detected in the cerebellum, striatum, thalamus and brain stem. FIG. 8. In contrast, MOR-1ha was heavily expressed in the striatum and thalamus, with low levels in the PAG, spinal cord and hypothalamus and no detectable amounts in cortex, cerebellum and brain stem. FIG. 8. MOR-1ja was only seen in the thalamus, while MOR-1ia was expressed only in the hypothalamus and spinal cord. Low levels of MOR-1k were seen in hypothalamus, PAG and spinal cord. FIG. 8. Of particular interest, MOR-1l, MOR-1m and MOR-1n were exclusively expressed in the spinal cord with no detectable level in any brain regions. FIG. 8.

EXAMPLE 6

Expression of Exon 11-Containing Proteins in Mouse Brain

To ensure that exon 11-containing products were expressed, Western blots were generated from mouse whole brain as previously reported. Pan et al. (1995). In brief, whole mouse brains were homogenized in Tris buffer with a cocktail of protease inhibitors (2 μM Aprotinin, 2 μM Leupeptin, 2 μM Pepstatin; 2 μM Bestatin, and 0.5 mM PMSF). The homogenate was solubilized with loading buffer and 20 μg of the total brain protein was loaded and run on a 4–20% gradient SDS-polyacrylamide gel, and transferred to a PVDF membrane. The membrane was blocked for 1 hr in TTBS buffer (10 mM Tris/HCl, pH 7.4, 150 mM NaCl, 0.05% Tween 20) containing 5% nonfat dried milk, and incubated at room temperature for 1 hr with the E11 antibody (1:2600 dilution) which had been adsorbed with an acetone extract of CHO cell membranes. The same antibody also was pre-incubated with 10 μg of E11 peptide at room temperature for 10 min as a control (Preabsorbed). After washing with TTBS buffer, the membrane was incubated with peroxidase-conjugated goat anti-rabbit antibody (1:15,000 dilution, Vector Laboratories) in TTBS buffer at room temperature for 1 hr. After washing with TTBS buffer, the signals were detected using Renaissance chemiluminescence reagents (NEN).

Figure 9:
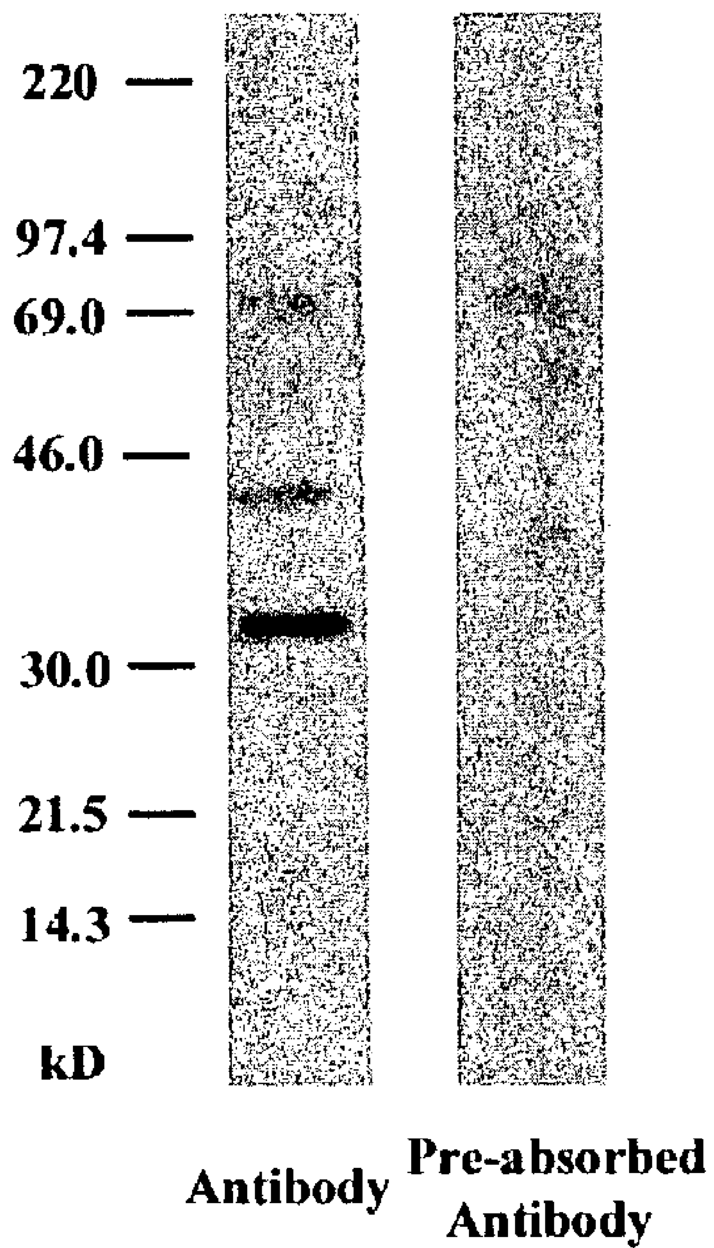
FIG. 9 depicts a Western blot of whole brain with an exon 11-specific antiserum, performed as described in Example 6. The antiserum was used as a probe in the left lane; antiserum that had been preadsorbed with the peptide used to generate the antibody was used as a probe in the right lane and represents a control.

Three bands (FIG. 9, left lane) were observed, with the lower two being specific. Preincubation of the antiserum with the peptide used to generate the antiserum eliminated labeling of the two major bands, but not the highest one. FIG. 9, right lane. Furthermore, the two lower bands were not seen when preimmune serum was used for labeling. The lower band was most intense and corresponded to MOR-1G (38 kDa) and/or MOR-1N (37.5 kDa). In some blots, the lower band appeared to be comprised of more than one band, implying the presence of both MOR-1G and MOR-1N. The middle band was less intense and corresponded to MOR-1M (42.3 kDa). The lower molecular weight products (<10 kDa) seen with in vitro translation were not observed.

Expression of exon 11-like immunoreactivity (E11-LI) also could be demonstrated immunohistochemically (FIG. 10B), with similar distributions from two different antisera. Immunostaining was performed with the affinity-purified antiserum described above, according to the avidin-biotin peroxidase method described by Hsu et al. (1981). Sections were incubated with a solution of 0.1 M PBS with a 3% normal goat serum and 0.3% Triton-X. The blocking solution was removed from the tissue and the sections were incubated overnight at room temperature in the primary antiserum. The sections were washed and then incubated in biotinylated goat anti-rabbit IgG (1:200) and avidin-biotin-peroxidase complex (1:100) (Vector Labs). To localize the HRP immunoreaction product, a nickel-intensified diaminobenzidine protocol with glucose oxidase adapted from Llewellyn-Smith and Minson (1992) was used. Finally, the sections were washed in PB, mounted on gelatin-coated slides, dried, and coverslipped with DPX (Aldrich, Milwaukee, Wis.).

Figure 10A:
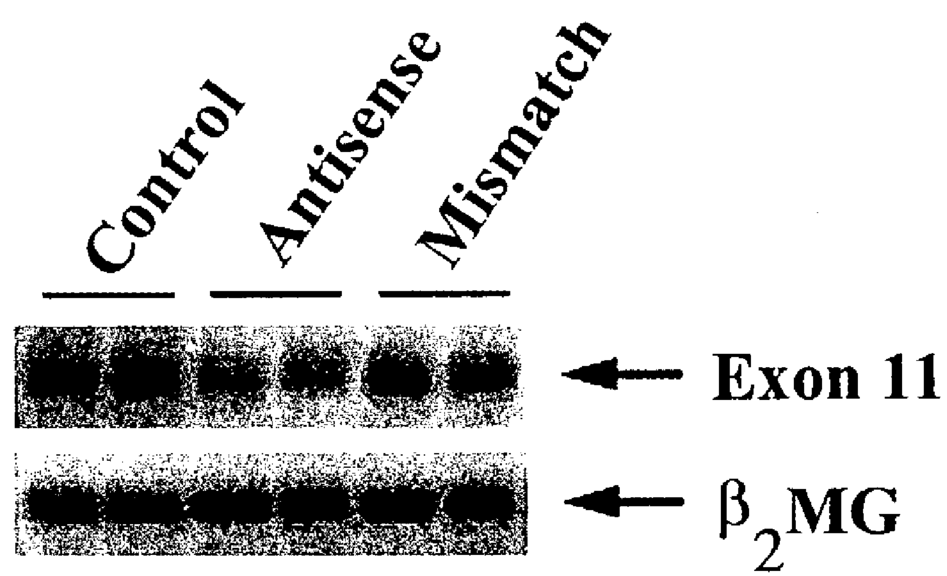
Figure 10B:
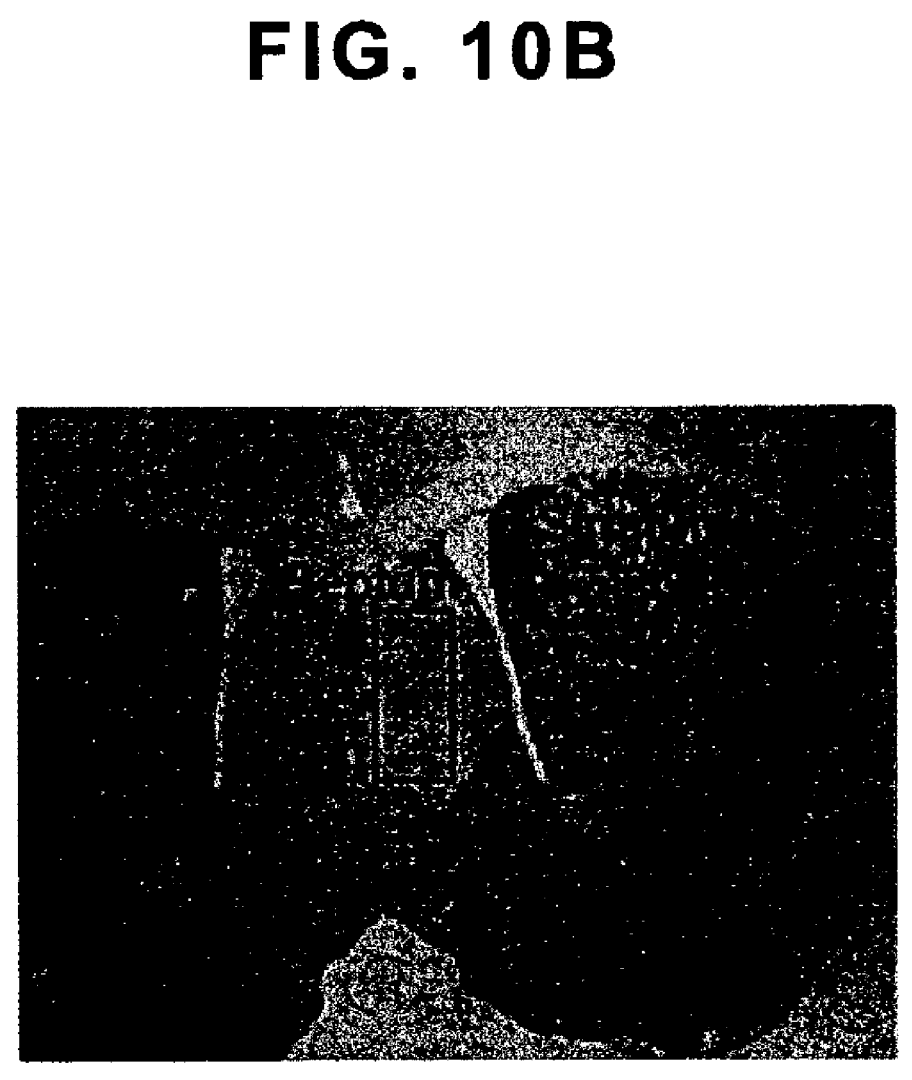
Figure 10C:
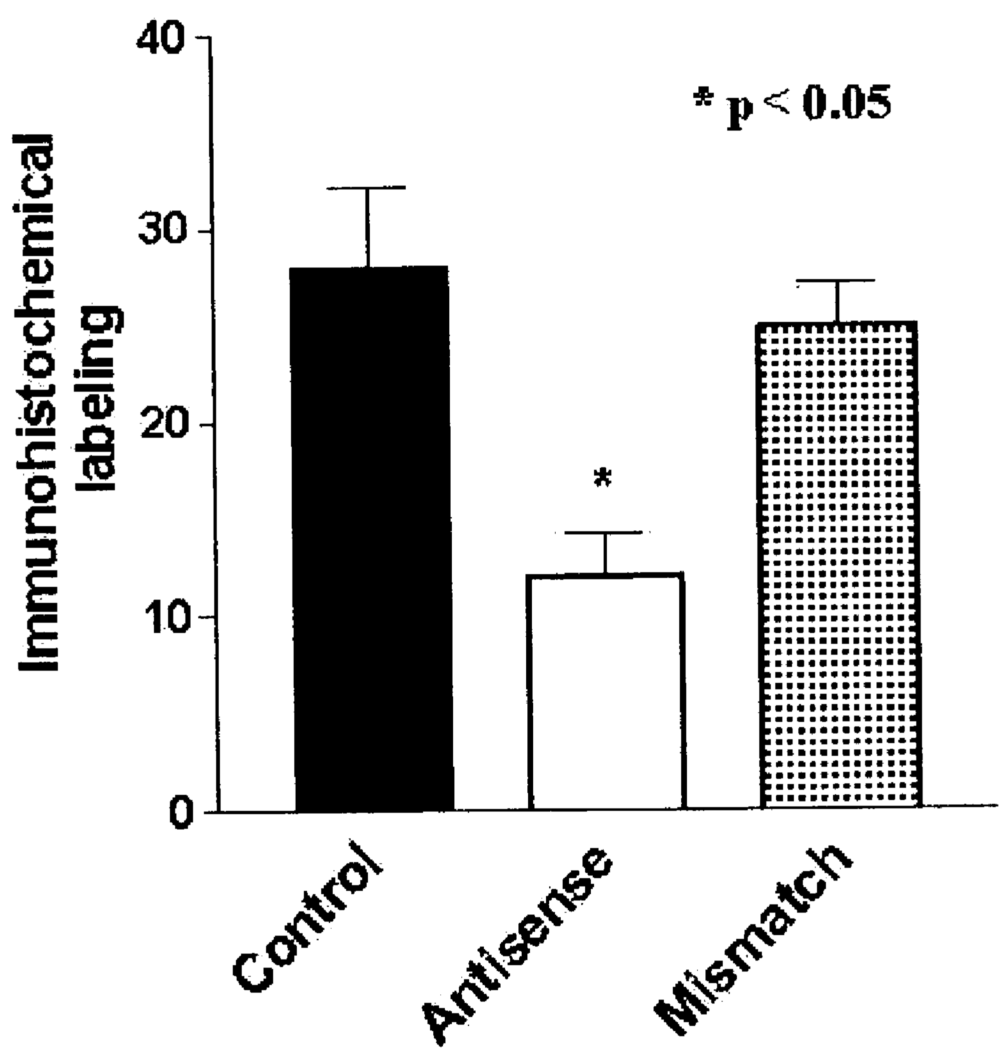

The labeling was prominent in the striatum, where it was diffuse, lacking the clusters previously seen autoradiographically (Atweh and Kuhar (1977); and Goodman and Pasternak (1985)) or immunohistochemically with antisera targeting exon 4 (E4), which corresponds to MOR-1 itself. Arvidsson et al. (1995); and Mansour et al. (1995). To ensure that the labeling reflected expression of an exon 11-containing variant(s), the effects of antisense treatments on both mRNA levels and immunohistochemical labeling were then examined. Antisense treatment lowered the levels of exon 11 expression by approximately 40%, as determined by RT-PCR. FIG. 10A. The mismatch treatment was inactive. The antisense treatment also downregulated the immunohistochemical labeling in the striatum by well over 50%, compared to the control group (p<0.05). FIGS. 10B,C. Again, the mismatch treatment was without effect.

EXAMPLE 7

In Vivo Antisense Mapping

Figure 11A:
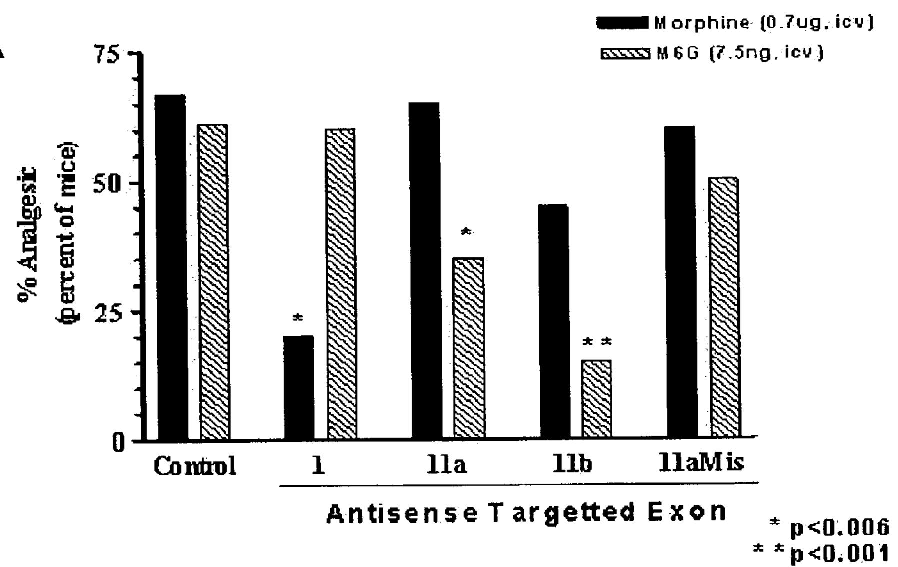
FIGS. 11A and B depict the results of in vivo antisense experiments with probes for exon 11 or exon 1 or exon 11a mismatch. Morphine or M6G analgesia was administered either supraspinally (A) or spinally (B) and the radiant heat tailflick test was used to assess analgesia.
Figure 11B:
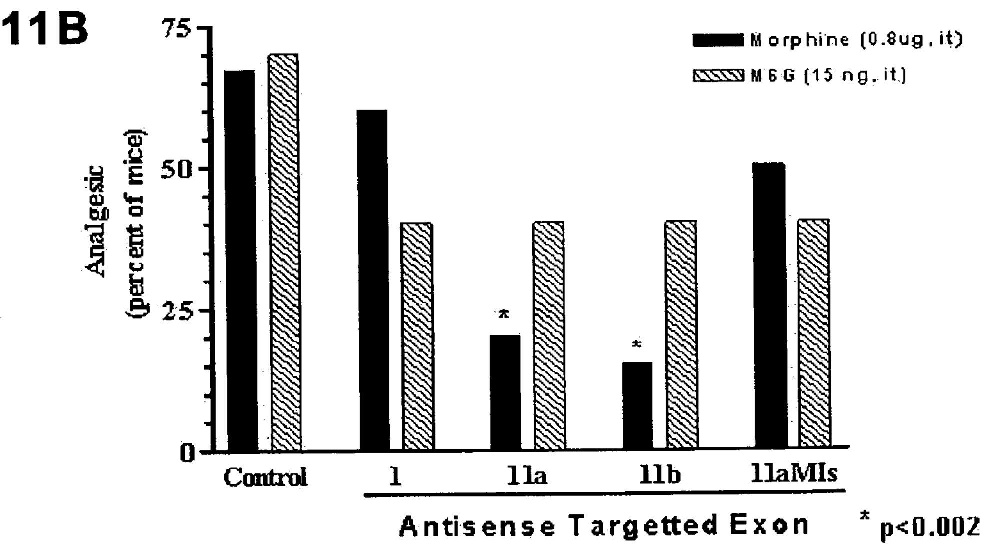

To explore the functional importance of variants containing exon 11, groups of mice (n=5) received either antisense E11A (10 μg, i.c.v.), mismatch E11A (10 μg, i.c.v.) or saline supraspinally under halothane anesthesia every day for 4 days. On the fifth day, three mice from each group were perfused for immunohistochemistry and two mice from each group were sacrificed and RNA extracted for RT-PCR (n=2/group). Groups of mice (n>20) were treated with two different antisense probes targeting exon 11, as well as an antisense probe targeting exon 1 on Days 1, 3 and 5, and tested for sensitivity towards morphine and M6G analgesia either spinally (i.t.) or supraspinally (i.c.v.), as described previously. FIGS. 11 and 12; Rossi et al. (1997a); Rossi et al. (1995a); Rossi et al. (1994); Rossi et al. (1995b). The following sequences were used: exon 1: 5'CGCCCCAGCCTCTTCCTCT3' (SEQ ID NO 47); exon 11a: 5'GACAGTCACTGGTGCCTATGCAAT3' (SEQ ID NO 48); and exon 11b: 5'CTCTTCCCCTCTTGATTTCCATCT3' (SEQ ID NO 49). The mismatch probe was based upon the 11a antisense probe, 5'GACGATCACGTGTGCTCATGACAT3' (SEQ ID NO 50). To ensure the specificity of the technique, mice were administered exon 11a (10 μg, i.c.v.) daily for four days and were sacrificed on the fifth day. The levels of exon 11-containing mRNA were determined by RT-PCR, as described above.

Immunoreactivity was digitized and specific immunolabeling in the striatum was determined after subtracting out the background labeling, defined by that in the lateral septum, with a computer-assisted imaging system (Scion Image PC). Specific labeling was defined as the difference in labeling intensity in the striatum compared to the lateral septum. FIG. 10B. The investigator responsible for measuring the density of the labeling was blind to the treatment of the animal being examined. Three sections per mouse for each of the three mice in each group were examined. Analysis of variance revealed significant differences between the three groups (p<0.05). Tukey's Multiple comparison revealed that the antisense, but not the mismatch, was significantly different from control (p<0.05).

Similar approaches were used for the functional antisense studies. In brief, animals were injected with 5 μg of purified oligodeoxynucleotide on days 1, 3 and 5 and examined for analgesic responses to the indicated opioid on day 6. Analgesia was determined using the radiant heat tailflick assay and was defined quantally as a doubling or greater of the baseline latency for the individual animal. Pan et al. (1995); and Rossi et al. (1995a). Statistical comparisons were carried out using the Fisher exact test. Each treatment group contained at least 20 mice.

The exon 1 probe reduced morphine analgesia supraspinally, but not spinally, and was inactive against M6G, confirming earlier observations by the applicants; the exon 11 antisense results differed. FIGS. 11 and 12. Supraspinally, both exon 11 antisense probes significantly lowered M6G analgesia without influencing the morphine response. In contrast to their supraspinal actions, at the spinal level the exon 11 antisense probes blocked spinal morphine analgesia without affecting M6G actions. The inactivity of a mismatch antisense probe for one of the exon 11 antisense probes supported the specificity of these observations.

Since eight different variants contain exon 11, it is not possible to identify the specific variant responsible for the actions blocked by the exon 11 antisense. However, the variants that contain exon 1, including MOR-1ha, MOR-1ia and MOR-1ja, can be eliminated from consideration. If they were responsible, the exon 1 antisense active against supraspinal morphine should also have blocked supraspinal M6G analgesia. Thus, these antisense mapping studies imply that at least one of the remaining variants are involved supraspinally in M6G analgesia and spinally in morphine analgesia, despite the fact that none of these variants appear to encode a traditional seven transmembrane, G-protein-coupled receptor.

All references cited herein, are hereby incorporated herein. Although the foregoing invention has been described in some detail, by way of illustration and example for the purposes of clarity and understanding, it will be apparent to those skilled in the art that certain changes and modifications can be practiced. Therefore, the description and examples should not be construed as limiting the scope of the invention, which is delineated by the appended claims.

What is claimed is:

1. An isolated human MOR-1P splice variant polypeptide that consists essentially of the amino acid residues having the sequence of SEQ ID NO 40.

2. An isolated human MOR-1O splice variant polypeptide that consists essentially of the amino acid residues having the sequence of SEQ ID NO 39.

3. A method of screening compositions for opioid activity comprising the steps of: a) obtaining a control cell that does not express an MOR-1 splice variant polypeptide; b) obtaining a test cell that is the same as the control cell except that it expresses an MOR-1 splice variant polypeptide of claim 1 or 2; c) contacting the control cell and test cell with an amount of an opioid sufficient to exert a physiologic effect; d) separately measuring the physiologic effect of the composition on the control cell and test cell; and e) comparing the physiologic effect wherein the physiologic effect is a change in the level of neuroendocrine hormones of the composition to the physiologic effect of the opioid, where determination of a physiologic effect of the composition is expressed relative to that of the opioid.

4. The method according to claim 3, where the composition is selected from the group consisting of synthetic combinatorial libraries of small molecule ligands, eukaryotic whole cell lysates or extracts, or media conditioned by cultured eukaryotic cells.

5. The method according to claim 3, where the opioid is selected from the group consisting of morphine, methadone, etorphine, levorphanol, fentanyl, sufentanil, [D-Ala2,MePhe4,Gly(ol)5]enkephalin, pentazocine, ethylketocyclazocine, bremazocine, spiradoline, [D-Ser2,Leu5]enkephalin-Thr6, Met-enkephalin, Leu-enkephalin, (3-endorphin, dynorphin A, dynorphin B, or a-neoendorphin.

6. The method according to claim 3, where the hormone is selected from the group consisting of prolactin, growth hormone, gonadotropin-releasing hormone, adrenocorticotropin, corticotropin-releasing factor, luteinizing hormone, follicle stimulating hormone, testosterone or cortisol.

7. A method of screening compositions for opioid binding activity comprising the steps of: a) obtaining a control polypeptide that is not an MOR-1 splice variant polypeptide; b) obtaining a test polypeptide that is an MOR-1 splice variant polypeptide of claim 1 or 2; c) contacting a composition with the control polypeptide and the test polypeptide; d) contacting the test polypeptide with an amount of an opioid sufficient to measurably bind the test polypeptide; e) measuring the binding of the composition and the opioid; and f) comparing test polypeptide binding of the composition to that of the opioid, where determination of binding of the composition is expressed relative to that of the opioid.

8. The method according to claim 7 where the composition is selected from the group consisting of synthetic combinatorial libraries of small molecule ligands, eukaryotic whole cell lysates or extracts, or media conditioned by cultured eukaryotic cells.

* * * * *

UNITED STATES PATENT AND TRADEMARK OFFICE

CERTIFICATE OF CORRECTION

PATENT NO. : 7,087,714 B2
APPLICATION NO. : 10/185083
DATED : August 8, 2006
INVENTOR(S) : Gavril W. Pasternak et al.

It is certified that error appears in the above-identified patent and that said Letters Patent is hereby corrected as shown below:

Column 1, lines 20-22; “and a core grant to Memorial Sloan-Kettering Cancer Center, New York, N.Y. (CA 08748) from the National Cancer Institute” should be deleted.

Column 1, line 22; “may have” should be changed to --has--.

Signed and Sealed this

Eleventh Day of March, 2008

JON W. DUDAS
*Director of the United States Patent and Trademark Office*

SEQUENCE LISTING

```
<160> NUMBER OF SEQ ID NOS: 56

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

catggtactg ggagaacctg ctca                                          24


<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

cccttctgtc gtcttctcgc agccgta                                       27


<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

tacggctgcg agaagacgac agaaggg                                       27


<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```

-continued ccggcatgat gaaggcgaag atga 24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
cggaaatcca gggccttgac cgg 23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
cctccaggct catttcagag ag 22

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ggcgcgggat ctgggccgat gatggaagct ttctctaagt ctgcattc 48

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ccaggaaacc agagcctccc acaa 24

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ggcgtgggac ccagttaggg ca 22

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gaaaggcatc ttccctctcg ctgt 24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
ccacactgct caccagctca tccc 24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gtggaaccag agaagagcgg cagg 24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ctttgtggtg gtcgaccagt tgcc 24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ggacgctcag acgttccatt ctgc 24

<210> SEQ ID NO 15
<211> LENGTH: 1440
<212> TYPE: DNA
<213> ORGANISM: Mus Sp.

<400> SEQUENCE: 15
ggcgcgggat ctgggccgat gatggaagct ttctctaagt ctgcattcca aaagctcaga 60
cagagagatg gaaatcaaga ggggaagagt tacctcaggg cttgtccttg taagaaactg 120
acggagccta gggcagctgt gagaggaaga ggctggggcg cctggaaccc gaacactctt 180
gagtgctctc agttacagcc taccgagtcc gcagcaagca ttcagaacca tggacagcag 240
cgccggccca gggaacatca gcgactgctc tgacccctta gctcctgcaa gttgctcccc 300
agcacctggc tcctggctca acttgtccca cgttgatggc aaccagtccg acccatgcgg 360
tcctaaccgc acggggcttg gcgggagcca cagcctgtgc cctcagaccg gcagcccttc 420
catggtcaca gccatcacca tcatggccct ctattctatc gtgtgtgtag tgggcctctt 480
tggaaacttc ctggtcatgt atgtgattgt aagatatacc aaaatgaaga ctgccaccaa 540

-continued

```
catctacatt ttcaaccttg ctctggcaga tgccttagcc actagcacgc tgccctttca    600

gagtgttaac tacctgatgg gaacgtggcc ctttggaaac atcctctgca agatcgtgat    660

ctcaatagac tactacaaca tgttcaccag tatcttcacc ctctgcacca tgagtgtaga    720

ccgctacatt gccgtctgcc acccggtcaa ggccctggat ttccgtaccc cccgaaatgc    780

caaaattgtc aatgtctgca actggatcct ctcttctgcc attggtctgc ccgtaatgtt    840

catggcaacc acaaaataca ggcaggggtc catagattgc accctcacgt tctctcatcc    900

cacatggtac tgggagaacc tgctcaaaat ctgtgtcttc atcttcgcct tcatcatgcc    960

ggtcctcatc atcactgtgt gttatggact gatgatctta cgactcaaga gtgtccgcat   1020

gctgtcgggc tccaaagaaa aggacaggaa cctgcgcagg atcacccgga tggtgctggt   1080

ggtcgtggct gtatttattg tctgctggac ccccatccac atctatgtca tcatcaaagc   1140

actgatcacg attccagaaa ccactttcca gactgtttcc tggcacttct gcattgcctt   1200

gggttacaca aacagctgcc tgaacccagt tctttatgcg ttcctggatg aaaacttcaa   1260

acgatgtttt agagagttct gcatcccaac ttcctccaca atcgaacagc aaaactctgc   1320

tcgaatccgt caaaacacta gggaacaccc ctccacggct aatacagtgg atcgaactaa   1380

ccaccagcta gaaaatctgg aagcagaaac tgctccattg ccctaactgg gtcccacgcc   1440
```

```
<210> SEQ ID NO 16
<211> LENGTH: 1614
<212> TYPE: DNA
<213> ORGANISM: Mus Sp.

<400> SEQUENCE: 16

ggcgcgggat ctgggccgat gatggaagct ttctctaagt ctgcattcca aaagctcaga     60

cagagagatg gaaatcaaga ggggaagagt tacctcagcc tctggatccc tcacagccca    120

tgctccctcc cttccactca gagagtggcg ctttggggat gctaaggatg cgcctccgtg    180

tacttctaag gtgggagggg gatacaagca gaggagaata tcggacgctc agacgttcca    240

ttctgcctgc cgctcttctc tggttccact agggcttgtc cttgtaagaa actgacggag    300

cctagggcag ctgtgagagg aagaggctgg ggcgcctgga acccgaacac tcttgagtgc    360

tctcagttac agcctaccga gtccgcagca agcattcaga accatggaca gcagcgccgg    420

cccagggaac atcagcgact gctctgaccc cttagctcct gcaagttgct ccccagcacc    480

tggctcctgg ctcaacttgt cccacgttga tggcaaccag tccgacccat gcggtcctaa    540

ccgcacgggg cttggcggga gccacagcct gtgccctcag accggcagcc cttccatggt    600

cacagccatc accatcatgg ccctctattc tatcgtgtgt gtagtgggcc tctttggaaa    660

cttcctggtc atgtatgtga ttgtaagata taccaaaatg aagactgcca ccaacatcta    720

cattttcaac cttgctctgg cagatgcctt agccactagc acgctgccct ttcagagtgt    780

taactacctg atgggaacgt ggccctttgg aaacatcctc tgcaagatcg tgatctcaat    840

agactactac aacatgttca ccagtatctt caccctctgc accatgagtg tagaccgcta    900

cattgccgtc tgccacccgg tcaaggccct ggatttccgt acccccgaa atgccaaaat    960

tgtcaatgtc tgcaactgga tcctctcttc tgccattggt ctgcccgtaa tgttcatggc   1020

aaccacaaaa tacaggcagg ggtccataga ttgcaccctc acgttctctc atcccacatg   1080

gtactgggag aacctgctca aaatctgtgt cttcatcttc gccttcatca tgccggtcct   1140

catcatcact gtgtgttatg gactgatgat cttacgactc aagagtgtcc gcatgctgtc   1200

gggctccaaa gaaaaggaca ggaacctgcg caggatcacc cggatggtgc tggtggtcgt   1260
```

```
ggctgtattt attgtctgct ggacccccat ccacatctat gtcatcatca aagcactgat   1320

cacgattcca gaaaccactt tccagactgt ttcctggcac ttctgcattg ccttgggtta   1380

cacaaacagc tgcctgaacc cagttcttta tgcgttcctg gatgaaaact tcaaacgatg   1440

ttttagagag ttctgcatcc caacttcctc cacaatcgaa cagcaaaact ctgctcgaat   1500

ccgtcaaaac actagggaac acccctccac ggctaataca gtggatcgaa ctaaccacca   1560

gctagaaaat ctggaagcag aaactgctcc attgccctaa ctgggtccca cgcc         1614
```

```
<210> SEQ ID NO 17
<211> LENGTH: 1569
<212> TYPE: DNA
<213> ORGANISM: Mus Sp.

<400> SEQUENCE: 17

ggcgcgggat ctgggccgat gatggaagct ttctctaagt ctgcattcca aaagctcaga     60

cagagagatg gaaatcaaga ggggaagagt tacctcaggt cttgtgcagg tgcactgctg    120

ctgtgaattc atgaagacaa caccctcccc tttagaagac agtgcttcac aacactccca    180

actagcctct ggctctgatg ttcactttgt cccctcttct gaagcagggc ttgtccttgt    240

aagaaactga cggagcctag ggcagctgtg agaggaagag gctggggcgc ctggaacccg    300

aacactcttg agtgctctca gttacagcct accgagtccg cagcaagcat tcagaaccat    360

ggacagcagc gccggcccag ggaacatcag cgactgctct gaccccttag ctcctgcaag    420

ttgctcccca gcacctggct cctggctcaa cttgtcccac gttgatggca accagtccga    480

cccatgcggt cctaaccgca cggggcttgg cgggagccac agcctgtgcc ctcagaccgg    540

cagcccttcc atggtcacag ccatcaccat catggccctc tattctatcg tgtgtgtagt    600

gggcctcttt ggaaacttcc tggtcatgta tgtgattgta agatatacca aaatgaagac    660

tgccaccaac atctacattt tcaaccttgc tctggcagat gccttagcca ctagcacgct    720

gccctttcag agtgttaact acctgatggg aacgtggccc tttggaaaca tcctctgcaa    780

gatcgtgatc tcaatagact actacaacat gttcaccagt atcttcaccc tctgcaccat    840

gagtgtagac cgctacattg ccgtctgcca cccggtcaag gccctggatt tccgtacccc    900

ccgaaatgcc aaaattgtca atgtctgcaa ctggatcctc tcttctgcca ttggtctgcc    960

cgtaatgttc atggcaacca caaaatacag gcaggggtcc atagattgca ccctcacgtt   1020

ctctcatccc acatggtact gggagaacct gctcaaaatc tgtgtcttca tcttcgcctt   1080

catcatgccg gtcctcatca tcactgtgtg ttatggactg atgatcttac gactcaagag   1140

tgtccgcatg ctgtcgggct ccaaagaaaa ggacaggaac ctgcgcagga tcacccggat   1200

ggtgctggtg gtcgtggctg tatttattgt ctgctggacc cccatccaca tctatgtcat   1260

catcaaagca ctgatcacga ttccagaaac cactttccag actgtttcct ggcacttctg   1320

cattgccttg ggttacacaa acagctgcct gaacccagtt ctttatgcgt tcctggatga   1380

aaacttcaaa cgatgtttta gagagttctg catcccaact tcctccacaa tcgaacagca   1440

aaactctgct cgaatccgtc aaaacactag ggaacacccc tccacggcta atacagtgga   1500

tcgaactaac caccagctag aaaatctgga agcagaaact gctccattgc cctaactggg   1560

tcccacgcc                                                           1569
```

```
<210> SEQ ID NO 18
<211> LENGTH: 1133
<212> TYPE: DNA
```

<213> ORGANISM: Mus Sp.

<400> SEQUENCE: 18

```
ggcgcgggat ctgggccgat gatggaagct ttctctaagt ctgcattcca aaagctcaga     60
cagagagatg gaaatcaaga ggggaagagt tacctcaggc tccctctgtc cattcttttc    120
ctgaacaaag agtcatgaca actcaaagaa tcaactgaaa atcaaaatag aaaatgggct    180
aaggcaactg gtcgaccacc acaaagatat accaaaatga agactgccac caacatctac    240
attttcaacc ttgctctggc agatgcctta gccactagca cgctgccctt tcagagtgtt    300
aactacctga tgggaacgtg gccctttgga aacatcctct gcaagatcgt gatctcaata    360
gactactaca acatgttcac cagtatcttc accctctgca ccatgagtgt agaccgctac    420
attgccgtct gccacccggt caaggccctg gatttccgta ccccccgaaa tgccaaaatt    480
gtcaatgtct gcaactggat cctctcttct gccattggtc tgcccgtaat gttcatggca    540
accacaaaat acaggcaggg gtccatagat tgcaccctca cgttctctca tcccacatgg    600
tactgggaga acctgctcaa aatctgtgtc ttcatcttcg ccttcatcat gccggtcctc    660
atcatcactg tgtgttatgg actgatgatc ttacgactca agagtgtccg catgctgtcg    720
ggctccaaag aaaaggacag gaacctgcgc aggatcaccc ggatggtgct ggtggtcgtg    780
gctgtattta ttgtctgctg gaccccccatc cacatctatg tcatcatcaa agcactgatc    840
acgattccag aaaccacttt ccagactgtt tcctggcact tctgcattgc cttgggttac    900
acaaacagct gcctgaaccc agttctttat gcgttcctgg atgaaaactt caaacgatgt    960
tttagagagt tctgcatccc aacttcctcc acaatcgaac agcaaaactc tgctcgaatc   1020
cgtcaaaaca ctagggaaca cccctccacg gctaatacag tggatcgaac taaccaccag   1080
ctagaaaatc tggaagcaga aactgctcca ttgccctaac tgggtcccac gcc          1133
```

<210> SEQ ID NO 19
<211> LENGTH: 1174
<212> TYPE: DNA
<213> ORGANISM: Mus Sp.

<400> SEQUENCE: 19

```
ggcgcgggat ctgggccgat gatggaagct ttctctaagt ctgcattcca aaagctcaga     60
cagagagatg gaaatcaaga ggggaagagt tacctcagac acctcattcc aaggaaggaa    120
attatctttt taaaactgaa ataactaggc attccaagca cctggcggtg agctgataaa    180
gactgagagt gtaatgagtc agaaaattgt gttgggttcc cctcttgagt gtgactaatg    240
tcaaaagata taccaaaatg aagactgcca ccaacatcta cattttcaac cttgctctgg    300
cagatgcctt agccactagc acgctgccct ttcagagtgt taactacctg atgggaacgt    360
ggccctttgg aaacatcctc tgcaagatcg tgatctcaat agactactac aacatgttca    420
ccagtatctt caccctctgc accatgagtg tagaccgcta cattgccgtc tgccacccgg    480
tcaaggccct ggatttccgt accccccgaa atgccaaaat tgtcaatgtc tgcaactgga    540
tcctctcttc tgccattggt ctgcccgtaa tgttcatggc aaccacaaaa tacaggcagg    600
ggtccataga ttgcaccctc acgttctctc atcccacatg gtactgggag aacctgctca    660
aaatctgtgt cttcatcttc gccttcatca tgccggtcct catcatcact gtgtgttatg    720
gactgatgat cttacgactc aagagtgtcc gcatgctgtc gggctccaaa gaaaaggaca    780
ggaacctgcg caggatcacc cggatggtgc tggtggtcgt ggctgtattt attgtctgct    840
ggaccccccat ccacatctat gtcatcatca aagcactgat cacgattcca gaaaccactt    900
```

```
tccagactgt ttcctggcac ttctgcattg ccttgggtta cacaaacagc tgcctgaacc    960

cagttcttta tgcgttcctg gatgaaaact tcaaacgatg ttttagagag ttctgcatcc   1020

caacttcctc cacaatcgaa cagcaaaact ctgctcgaat ccgtcaaaac actagggaac   1080

acccctccac ggctaataca gtggatcgaa ctaaccacca gctagaaaat ctggaagcag   1140

aaactgctcc attgccctaa ctgggtccca cgcc                               1174


<210> SEQ ID NO 20
<211> LENGTH: 1082
<212> TYPE: DNA
<213> ORGANISM: Mus Sp.

<400> SEQUENCE: 20

ggcgcgggat ctgggccgat gatggaagct ttctctaagt ctgcattcca aaagctcaga     60

cagagagatg gaaatcaaga ggggaagagt tacctcagat ataccaaaat gaagactgcc    120

accaacatct acattttcaa ccttgctctg gcagatgcct tagccactag cacgctgccc    180

tttcagagtg ttaactacct gatgggaacg tggccctttg gaaacatcct ctgcaagatc    240

gtgatctcaa tagactacta caacatgttc accagtatct tcaccctctg caccatgagt    300

gtagaccgct acattgccgt ctgccacccg gtcaaggccc tggatttccg taccccccga    360

aatgccaaaa ttgtcaatgt ctgcaactgg atcctctctt ctgccattgg tctgcccgta    420

atgttcatgg caaccacaaa atacaggcag gggtccatag attgcaccct cacgttctct    480

catcccacat ggtactggga gaacctgctc aaaatctgtg tcttcatctt cgccttcatc    540

atgccggtcc tcatcatcac tgtgtgttat ggactgatga tcttacgact caagagtgtc    600

cgcatgctgt cgggctccaa agaaaaggac aggaacctgc gcaggatcac ccggatggtg    660

ctggtggtcg tggctgtatt tattgtctgc tggacccccca tccacatcta tgtcatcatc    720

aaagcactga tcacgattcc agaaaccact ttccagactg tttcctggca cttctgcatt    780

gccttgggtt acacaaacag ctgcctgaac ccagttcttt atgcgttcct ggatgaaaac    840

ttcaaacgat gttttagaga gttctgcatc ccaacttcct ccacaatcga acagcaaaac    900

tctgctcgaa tccgtcaaaa cactagggaa cacccctcca cggctaatac agtggatcga    960

actaaccacc agaggaatga ggaaccttct tcctgatgat ggcccaagac aggaatccgg   1020

ggaaggccag cttggcaggt gaatgtcatc cgaacacagg gatgagctgg tgagcagtgt   1080

gg                                                                  1082


<210> SEQ ID NO 21
<211> LENGTH: 2951
<212> TYPE: DNA
<213> ORGANISM: Mus Sp.

<400> SEQUENCE: 21

ggaacccgaa cactcttgag tgctctcagt tacagcctac cgagtccgca gcaagcattc     60

agaaccatgg acagcagcgc cggcccaggg aacatcagcg actgctctga ccccttagct    120

cctgcaagtt gctccccagc acctggctcc tggctcaact tgtcccacgt tgatggcaac    180

cagtccgacc catgcggtcc taaccgcacg gggcttggcg ggagccacag cctgtgccct    240

cagaccggca gcccttccat ggtcacagcc atcaccatca tggccctcta ttctatcgtg    300

tgtgtagtgg gcctctttgg aaacttcctg gtcatgtatg tgattgtaag atataccaaa    360

atgaagactg ccaccaacat ctacattttc aaccttgctc tggcagatgc cttagccact    420
```

-continued

```
agcacgctgc cctttcagag tgttaactac ctgatgggaa cgtggccctt tggaaacatc    480
ctctgcaaga tcgtgatctc aatagactac tacaacatgt tcaccagtat cttcaccctc    540
tgcaccatga gtgtagaccg ctacattgcc gtctgccacc cggtcaaggc cctggatttc    600
cgtacccccc gaaatgccaa aattgtcaat gtctgcaact ggatcctctc ttctgccatt    660
ggtctgcccg taatgttcat ggcaaccaca aaatacaggc aggggtccat agattgcacc    720
ctcacgttct ctcatcccac atggtactgg gagaacctgc tcaaaatctg tgtcttcatc    780
ttcgccttca tcatgccggt cctcatcatc actgtgtgtt atggactgat gatcttacga    840
ctcaagagtg tccgcatgct gtcgggctcc aaagaaaagg acaggaacct gcgcaggatc    900
acccggatgg tgctggtggt cgtggctgta tttattgtct gctggacccc catccacatc    960
tatgtcatca tcaaagcact gatcacgatt ccagaaacca ctttccagac tgtttcctgg   1020
cacttctgca ttgccttggg ttacacaaac agctgcctga acccagttct ttatgcgttc   1080
ctggatgaaa acttcaaacg atgttttaga gagttctgca tcccaacttc ctccacaatc   1140
gaacagcaaa actctgctcg aatccgtcaa aacactaggg aacacccctc cacggctaat   1200
acagtggatc gaactaacca ccagtgtgta tgagtgctat gcccacaggg accagaagat   1260
ggtatcagac cttctagaac tgaagtagtg agcagtcccc acccccaccc ccccgcaatg   1320
tgagtagctt ataaaatgat tttatgtact tgttagctct ccatggagca caagataaaa   1380
gtgacatcac agtttgaaat aatagctctt tgatcctaga atgaaagcat ggaaaaaata   1440
agttgggtca tttgtctata ggaaggaagg ggacaaggtg gggacagaga ggactgagaa   1500
gacgtagaca attaaggtag gaagaaggct aatctagata gcacatttac gttccaaatc   1560
cactacttct tcttgtgtgt ctttcaggca caccaaaaac ctcaagaatg cctgaaatgc   1620
agatgtctat cccttaccat cctggttata tgcctacatt tccaacatca gcaattcttc   1680
ataatgatca aaaaaaatgt ttcataacta aaggaaaaac catctgcttc ttttgattta   1740
atgaaactta aatatctctg ggtgtggggg acattaggat gttaaagttt cttcaaagga   1800
aagagataac ttctcatagt gctgaaatgg gtaccctcaa gataggggac aggcaaacag   1860
agtttatgga agatgatatt aagaaagaaa aacatatcaa tcaagaaaaa tagtgttacg   1920
tattttgaca acaaagccta attgataact tacagaaatt aatatatgta gaatgggata   1980
agacttctgt gcattgatga taaatctgct gcttagcccc tgttacaatg tacagctaag   2040
tacgtctttc ttgtctttct ttctgtgctt tcttcacttt gatttaggct aaaatgtcag   2100
ttattcaaag gcccctaata ttgccaaatc cagtctcatt ccagatcctg tagaattaat   2160
attagtttga gttgctcttt cagagaaaat gacatgcagc ccgaatcatt attcacaaag   2220
aaaaagggcc aatccaaggt gaagtgttgc taacactgga aaggtctgaa caaggcctac   2280
tttcctaaca ataacaacgc ctcaagagat cttcaggatg aaatacaact cgaaaaatat   2340
aaattataaa gccctggacg taaatcacaa ggagtaagag gagtctctga catattgggt   2400
aagatagagc cccaagatta atgggaaaga ttctagcaaa cgaacaacca caaactatca   2460
agctgtgtaa acttgtccca gaacctgggt cacagtgaga ggagcaggtg gctctgagaa   2520
gcaagactgc atctggcaaa attgcaaaga aagaaattag ctactagatg gcacaattgg   2580
atgaactcga gaacccagtg gtttatgtag atttgaaaac ctctatcaat ctctgtaacc   2640
atacactgtg tttagttctg atctaaattt aatgatgcta tgacttagct ttataaaatt   2700
ttatctcatt gtattcttag gagcctcagt cagcagagac atgatgtgaa tgaacggact   2760
gattagacaa ggtttcctga acactgaaat acaaaacaaa tagagagctt actagagaaa   2820
```

```
attcgtagcc cgaaaattca attatagaaa caaatgagtg ttagagtaga tatggtaagg   2880

cctcagagag gttttatttc atgactaaca acatgaccca aggcacctaa tccatggtga   2940

ttagattaca a                                                         2951
```

<210> SEQ ID NO 22
<211> LENGTH: 1332
<212> TYPE: DNA
<213> ORGANISM: Mus Sp.

<400> SEQUENCE: 22

```
ggaacccgaa cactcttgag tgctctcagt tacagcctac cgagtccgca gcaagcattc     60

agaaccatgg acagcagcgc cggcccaggg aacatcagcg actgctctga ccccttagct    120

cctgcaagtt gctccccagc acctggctcc tggctcaact tgtcccacgt tgatggcaac    180

cagtccgacc catgcggtcc taaccgcacg gggcttggcg ggagccacag cctgtgccct    240

cagaccggca gcccttccat ggtcacagcc atcaccatca tggccctcta ttctatcgtg    300

tgtgtagtgg gcctctttgg aaacttcctg gtcatgtatg tgattgtaag atataccaaa    360

atgaagactg ccaccaacat ctacattttc aaccttgctc tggcagatgc cttagccact    420

agcacgctgc cctttcagag tgttaactac ctgatgggaa cgtggccctt tggaaacatc    480

ctctgcaaga tcgtgatctc aatagactac tacaacatgt tcaccagtat cttcaccctc    540

tgcaccatga gtgtagaccg ctacattgcc gtctgccacc cggtcaaggc cctggatttc    600

cgtacccccc gaaatgccaa aattgtcaat gtctgcaact ggatcctctc ttctgccatt    660

ggtctgcccg taatgttcat ggcaaccaca aaatacaggc aggggtccat agattgcacc    720

ctcacgttct ctcatcccac atggtactgg gagaacctgc tcaaaatctg tgtcttcatc    780

ttcgccttca tcatgccggt cctcatcatc actgtgtgtt atggactgat gatcttacga    840

ctcaagagtg tccgcatgct gtcgggctcc aaagaaaagg acaggaacct gcgcaggatc    900

acccggatgg tgctggtggt cgtggctgta tttattgtct gctggacccc catccacatc    960

tatgtcatca tcaaagcact gatcacgatt ccagaaacca ctttccagac tgtttcctgg   1020

cacttctgca ttgccttggg ttacacaaac agctgcctga acccagttct ttatgcgttc   1080

ctggatgaaa acttcaaacg atgttttaga gagttctgca tcccaacttc ctccacaatc   1140

gaacagcaaa actctgctcg aatccgtcaa aacactaggg aacacccctc cacggctaat   1200

acagtggatc gaactaacca ccagacaagc ctcacacttc agtaatggaa tgagtagatt   1260

aaatcggcga gcaagatggt gggaggagtc aaaatatttt catgccttcc tgtggaactc   1320

caaaggaaga cc                                                        1332
```

<210> SEQ ID NO 23
<211> LENGTH: 2588
<212> TYPE: DNA
<213> ORGANISM: Mus Sp.

<400> SEQUENCE: 23

```
ggaacccgaa cactcttgag tgctctcagt tacagcctac cgagtccgca gcaagcattc     60

agaaccatgg acagcagcgc cggcccaggg aacatcagcg actgctctga ccccttagct    120

cctgcaagtt gctccccagc acctggctcc tggctcaact tgtcccacgt tgatggcaac    180

cagtccgacc catgcggtcc taaccgcacg gggcttggcg ggagccacag cctgtgccct    240

cagaccggca gcccttccat ggtcacagcc atcaccatca tggccctcta ttctatcgtg    300
```

-continued

```
tgtgtagtgg gcctctttgg aaacttcctg gtcatgtatg tgattgtaag atataccaaa    360
atgaagactg ccaccaacat ctacattttc aaccttgctc tggcagatgc cttagccact    420
agcacgctgc cctttcagag tgttaactac ctgatgggaa cgtggccctt tggaaacatc    480
ctctgcaaga tcgtgatctc aatagactac tacaacatgt tcaccagtat cttcaccctc    540
tgcaccatga gtgtagaccg ctacattgcc gtctgccacc cggtcaaggc cctggatttc    600
cgtacccccc gaaatgccaa aattgtcaat gtctgcaact ggatcctctc ttctgccatt    660
ggtctgcccg taatgttcat ggcaaccaca aaatacaggc aggggtccat agattgcacc    720
ctcacgttct ctcatcccac atggtactgg gagaacctgc tcaaaatctg tgtcttcatc    780
ttcgccttca tcatgccggt cctcatcatc actgtgtgtt atggactgat gatcttacga    840
ctcaagagtg tccgcatgct gtcgggctcc aaagaaaagg acaggaacct gcgcaggatc    900
acccggatgg tgctggtggt cgtggctgta tttattgtct gctggacccc catccacatc    960
tatgtcatca tcaaagcact gatcacgatt ccagaaacca ctttccagac tgtttcctgg   1020
cacttctgca ttgccttggg ttacacaaac agctgcctga acccagttct ttatgcgttc   1080
ctggatgaaa acttcaaacg atgttttaga gagttctgca tcccaacttc ctccacaatc   1140
gaacagcaaa actctgctcg aatccgtcaa aacactaggg aacacccctc cacggctaat   1200
acagtggatc gaactaacca ccaggcacac caaaaacctc aagaatgcct gaaatgcaga   1260
tgtctatccc ttaccatcct ggttatatgc ctacatttcc aacatcagca attcttcata   1320
atgatcaaaa aaaatgtttc ataactaaag gaaaaaccat ctgcttcttt tgatttaatg   1380
aaacttaaat atctctgggt gtgggggaca ttaggatgtt aaagtttctt caaaggaaag   1440
agataacttc tcatagtgct gaaatgggta ccctcaagat aggggacagg caaacagagt   1500
ttatggaaga tgatattaag aaagaaaaac atatcaatca agaaaaatag tgttacgtat   1560
tttgacaaca aagcctaatt gataacttac agaaattaat atatgtagaa tgggataaga   1620
cttctgtgca ttgatgataa atctgctgct tagcccctgt tacaatgtac agctaagtac   1680
gtctttcttg tctttctttc tgtgctttct tcactttgat ttaggctaaa atgtcagtta   1740
ttcaaaggcc cctaatattg ccaaatccag tctcattcca gatcctgtag aattaatatt   1800
agtttgagtt gctctttcag agaaaatgac atgcagcccg aatcattatt cacaaagaaa   1860
aagggccaat ccaaggtgaa gtgttgctaa cactggaaag gtctgaacaa ggcctacttt   1920
cctaacaata acaacgcctc aagagatctt caggatgaaa tacaactcga aaaatataaa   1980
ttataaagcc ctggacgtaa atcacaagga gtaagaggag tctctgacat attgggtaag   2040
atagagcccc aagattaatg ggaaagattc tagcaaacga acaaccacaa actatcaagc   2100
tgtgtaaact tgtcccagaa cctgggtcac agtgagagga gcaggtggct ctgagaagca   2160
agactgcatc tggcaaaatt gcaaagaaag aaattagcta ctagatggca caattggatg   2220
aactcgagaa cccagtggtt tatgtagatt tgaaaacctc tatcaatctc tgtaaccata   2280
cactgtgttt agttctgatc taaatttaat gatgctatga cttagcttta taaaatttta   2340
tctcattgta ttcttaggag cctcagtcag cagagacatg atgtgaatga acggactgat   2400
tagacaaggt ttcctgaaca ctgaaataca aaacaaatag agagcttact agagaaaatt   2460
cgtagcccga aaattcaatt atagaaacaa atgagtgtta gagtagatat ggtaaggcct   2520
cagagaggtt ttatttcatg actaacaaca tgacccaagg cacctaatcc atggtgatta   2580
gattacaa                                                             2588
```

<210> SEQ ID NO 24
<211> LENGTH: 1695
<212> TYPE: DNA
<213> ORGANISM: Mus Sp.

<400> SEQUENCE: 24

```
ggaacccgaa cactcttgag tgctctcagt tacagcctac cgagtccgca gcaagcattc     60
agaaccatgg acagcagcgc cggcccaggg aacatcagcg actgctctga cccccttagct   120
cctgcaagtt gctccccagc acctggctcc tggctcaact tgtcccacgt tgatggcaac    180
cagtccgacc catgcggtcc taaccgcacg gggcttggcg ggagccacag cctgtgccct    240
cagaccggca gcccttccat ggtcacagcc atcaccatca tggccctcta ttctatcgtg    300
tgtgtagtgg gcctctttgg aaacttcctg gtcatgtatg tgattgtaag atataccaaa    360
atgaagactg ccaccaacat ctacattttc aaccttgctc tggcagatgc cttagccact    420
agcacgctgc cctttcagag tgttaactac ctgatgggaa cgtggccctt tggaaacatc    480
ctctgcaaga tcgtgatctc aatagactac tacaacatgt tcaccagtat cttcaccctc    540
tgcaccatga gtgtagaccg ctacattgcc gtctgccacc cggtcaaggc cctggatttc    600
cgtacccccc gaaatgccaa aattgtcaat gtctgcaact ggatcctctc ttctgccatt    660
ggtctgcccg taatgttcat ggcaaccaca aaatacaggc aggggtccat agattgcacc    720
ctcacgttct ctcatcccac atggtactgg gagaacctgc tcaaaatctg tgtcttcatc    780
ttcgccttca tcatgccggt cctcatcatc actgtgtgtt atggactgat gatcttacga    840
ctcaagagtg tccgcatgct gtcgggctcc aaagaaaagg acaggaacct gcgcaggatc    900
acccggatgg tgctggtggt cgtggctgta tttattgtct gctggacccc catccacatc    960
tatgtcatca tcaaagcact gatcacgatt ccagaaacca ctttccagac tgtttcctgg   1020
cacttctgca ttgccttggg ttacacaaac agctgcctga acccagttct ttatgcgttc   1080
ctggatgaaa acttcaaacg atgttttaga gagttctgca tcccaacttc ctccacaatc   1140
gaacagcaaa actctgctcg aatccgtcaa aacactaggg aacacccctc cacggctaat   1200
acagtggatc gaactaacca ccagataatg aaatttgaag ctatctaccc taaactgagc   1260
ttcaaatctt gggcattgaa atattttact ttcattagag aaaagaaaag gaacacaaaa   1320
gctggggctc ttcctcccct ccctacgtgt catgctggat ctccctccca ggctcacagg   1380
ggcgtggctg cttggttgct tcctctaaga cacatggggc cttcttatcc ttcctgaccc   1440
acctgacctt cctctaatgg aagcagagcc ccaagctctc tattccagca catccctgtt   1500
ttaaacatag ctgcccttca gattctctaa cgctgccttc gactcccttc cacacccagt   1560
gtttgcatgt cagtgtggat cttgcacagc cagagagtag aagggaagat aattggagaa   1620
gctctgtcct aagtaactaa aaggtttgct ttaaaaatac atccaattag cacttatcat   1680
tatcactgcc tctgc                                                      1695
```

<210> SEQ ID NO 25
<211> LENGTH: 1464
<212> TYPE: DNA
<213> ORGANISM: Homo Sapiens

<400> SEQUENCE: 25

```
cggtgctcct ggctacctcg cacagcgtgc ccgcccggcc gtcagtacca tggacagcag     60
cgctgccccc acgaacgcca gcaattgcac tgatgccttg gcgtactcaa gttgctcccc    120
agcacccagc cccggttcct gggtcaactt gtcccactta gatggcaacc tgtccgaccc    180
```

-continued

```
atgcggtccg aaccgcaccg acctgggcgg gagagacagc ctgtgccctc cgaccggcag    240

tccctccatg atcacggcca tcacgatcat ggccctctac tccatcgtgt gcgtggtggg    300

gctcttcgga aacttcctgg tcatgtatgt gattgtcaga tacaccaaga tgaagactgc    360

caccaacatc tacattttca accttgctct ggcagatgcc ttagccacca gtaccctgcc    420

cttccagagt gtgaattacc taatgggaac atggccattt ggaaccatcc tttgcaagat    480

agtgatctcc atagattact ataacatgtt caccagcata ttcaccctct gcaccatgag    540

tgttgatcga tacattgcag tctgccaccc tgtcaaggcc ttagatttcc gtactccccg    600

aaatgccaaa attatcaatg tctgcaactg gatcctctct tcagccattg gtcttcctgt    660

aatgttcatg gctacaacaa aatacaggca aggttccata gattgtacac taacattctc    720

tcatccaacc tggtactggg aaaacctgct gaagatctgt gttttcatct tcgccttcat    780

tatgccagtg ctcatcatta ccgtgtgcta tggactgatg atcttgcgcc tcaagagtgt    840

ccgcatgctc tctggctcca aagaaaagga caggaatctt cgaaggatca ccaggatggt    900

gctggtggtg gtggctgtgt tcatcgtctg ctggactccc attcacattt acgtcatcat    960

taaagccttg gttacaatcc cagaaactac gttccagact gtttcttggc acttctgcat   1020

tgctctaggt tacacaaaca gctgcctcaa cccagtcctt tatgcatttc tggatgaaaa   1080

cttcaaacga tgcttcagag agttctgtat cccaacctct tccaacattg agcaacaaaa   1140

ctccactcga attcgtcaga acactagaga ccacccctcc acggccaata cagtggatag   1200

aactaatcat cagtgcctac ctataccttc cctgtcttgc tgggctctag agcatggctg   1260

cttggttgtg taccctggac cactgcaagg acctcttgtc agatatgacc tcccagctat   1320

ccttcactcg tcctgccttc gtggaaatac tgctcccagc ccgtctggtg ggcatttct    1380

cttgagttaa gcatgattat tcttcagttg cccgacactg cccttgactc ccttccaaat   1440

tcggcatttt cacatcagta tggc                                          1464
```

<210> SEQ ID NO 26
<211> LENGTH: 1388
<212> TYPE: DNA
<213> ORGANISM: Homo Sapiens

<400> SEQUENCE: 26

```
cggtgctcct ggctacctcg cacagcgtgc ccgcccggcc gtcagtacca tggacagcag     60

cgctgccccc acgaacgcca gcaattgcac tgatgccttg gcgtactcaa gttgctcccc    120

agcacccagc cccggttcct gggtcaactt gtcccactta gatggcaacc tgtccgaccc    180

atgcggtccg aaccgcaccg acctgggcgg gagagacagc ctgtgccctc cgaccggcag    240

tccctccatg atcacggcca tcacgatcat ggccctctac tccatcgtgt gcgtggtggg    300

gctcttcgga aacttcctgg tcatgtatgt gattgtcaga tacaccaaga tgaagactgc    360

caccaacatc tacattttca accttgctct ggcagatgcc ttagccacca gtaccctgcc    420

cttccagagt gtgaattacc taatgggaac atggccattt ggaaccatcc tttgcaagat    480

agtgatctcc atagattact ataacatgtt caccagcata ttcaccctct gcaccatgag    540

tgttgatcga tacattgcag tctgccaccc tgtcaaggcc ttagatttcc gtactccccg    600

aaatgccaaa attatcaatg tctgcaactg gatcctctct tcagccattg gtcttcctgt    660

aatgttcatg gctacaacaa aatacaggca aggttccata gattgtacac taacattctc    720

tcatccaacc tggtactggg aaaacctgct gaagatctgt gttttcatct tcgccttcat    780

tatgccagtg ctcatcatta ccgtgtgcta tggactgatg atcttgcgcc tcaagagtgt    840
```

```
ccgcatgctc tctggctcca aagaaaagga caggaatctt cgaaggatca ccaggatggt    900

gctggtggtg gtggctgtgt tcatcgtctg ctggactccc attcacattt acgtcatcat    960

taaagccttg gttacaatcc cagaaactac gttccagact gtttcttggc acttctgcat   1020

tgctctaggt tacacaaaca gctgcctcaa cccagtcctt tatgcatttc tggatgaaaa   1080

cttcaaacga tgcttcagag agttctgtat cccaacctct tccaacattg agcaacaaaa   1140

ctccactcga attcgtcaga acactagaga ccacccctcc acggccaata cagtggatag   1200

aactaatcat cagccaccct tggcagtcag catggcccag atctttacac gatatcctcc   1260

tccgactcat cgtgagaaaa cctgcaatga ttacatgaag aggtagataa tgtattaccc   1320

tgatttggta ggtaaagtat tatcctgatt tatgtgacag agtgaaaggc aacttttaat   1380

tgttaacc                                                            1388
```

<210> SEQ ID NO 27
<211> LENGTH: 1258
<212> TYPE: DNA
<213> ORGANISM: Mus Sp.

<400> SEQUENCE: 27

```
ttttactgtc cttgagaatg gagaggatca gcaaagctgg gaagccctcc aggctcattt     60

cagagagaat attccacaga gcttgaaggc gcgggatctg ggccgatgat ggaagctttc    120

tctaagtctg cattccaaaa gctcagacag agagatggaa atcaagaggg gaagagttac    180

ctcagatata ccaaaatgaa gactgccacc aacatctaca ttttcaacct tgctctggca    240

gatgccttag ccactagcac gctgcccttt cagagtgtta actacctgat gggaacgtgg    300

ccctttggaa acatcctctg caagatcgtg atctcaatag actactacaa catgttcacc    360

agtatcttca ccctctgcac catgagtgta gaccgctaca ttgccgtctg ccacccggtc    420

aaggccctgg atttccgtac cccccgaaat gccaaaattg tcaatgtctg caactggatc    480

ctctcttctg ccattggtct gcccgtaatg ttcatggcaa ccacaaaata caggcagggg    540

tccatagatt gcaccctcac gttctctcat cccacatggt actgggagaa cctgctcaaa    600

atctgtgtct tcatcttcgc cttcatcatg ccggtcctca tcatcactgt gtgttatgga    660

ctgatgatct tacgactcaa gagtgtccgc atgctgtcgg gctccaaaga aaaggacagg    720

aacctgcgca ggatcacccg gatggtgctg gtggtcgtgg ctgtatttat tgtctgctgg    780

acccccatcc acatctatgt catcatcaaa gcactgatca cgattccaga aaccactttc    840

cagactgttt cctggcactt ctgcattgcc ttgggttaca caaacagctg cctgaaccca    900

gttctttatg cgttcctgga tgaaaacttc aaacgatgtt ttagagagtt ctgcatccca    960

acttcctcca caatcgaaca gcaaaactct gctcgaatcc gtcaaaacac tagggaacac   1020

cctccacgg ctaatacagt ggatcgaact aaccaccagc caaccctggc agtcagcgtg    1080

gcccagatct ttacaggata tccttctccg actcatgttg aaaaaccctg caagagttgc   1140

atggacagag gaatgaggaa ccttcttcct gatgatggcc caagacagga atccggggaa   1200

ggccagcttg gcaggtgaat gtcatccgaa cacagggatg agctggtgag cagtgtgg     1258
```

<210> SEQ ID NO 28
<211> LENGTH: 84
<212> TYPE: PRT
<213> ORGANISM: Mus Sp.

<400> SEQUENCE: 28

-continued

```
Met Met Glu Ala Phe Ser Lys Ser Ala Phe Gln Lys Leu Arg Gln Arg
1               5                   10                  15

Asp Gly Asn Gln Glu Gly Lys Ser Tyr Leu Arg Ala Cys Pro Cys Lys
            20                  25                  30

Lys Leu Thr Glu Pro Arg Ala Ala Val Arg Gly Arg Gly Trp Gly Ala
        35                  40                  45

Trp Asn Pro Asn Thr Leu Glu Cys Ser Gln Leu Gln Pro Thr Glu Ser
    50                  55                  60

Ala Ala Ser Ile Gln Asn His Gly Gln Gln Arg Arg Pro Arg Glu His
65                  70                  75                  80

Gln Arg Leu Leu


<210> SEQ ID NO 29
<211> LENGTH: 48
<212> TYPE: PRT
<213> ORGANISM: Mus Sp.

<400> SEQUENCE: 29

Met Met Glu Ala Phe Ser Lys Ser Ala Phe Gln Lys Leu Arg Gln Arg
1               5                   10                  15

Asp Gly Asn Gln Glu Gly Lys Ser Tyr Leu Ser Leu Trp Ile Pro His
            20                  25                  30

Ser Pro Cys Ser Leu Pro Ser Thr Gln Arg Val Ala Leu Trp Gly Cys
        35                  40                  45


<210> SEQ ID NO 30
<211> LENGTH: 35
<212> TYPE: PRT
<213> ORGANISM: Mus Sp.

<400> SEQUENCE: 30

Met Met Glu Ala Phe Ser Lys Ser Ala Phe Gln Lys Leu Arg Gln Arg
1               5                   10                  15

Asp Gly Asn Gln Glu Gly Lys Ser Tyr Leu Arg Ser Cys Ala Gly Ala
            20                  25                  30

Leu Leu Leu
        35


<210> SEQ ID NO 31
<211> LENGTH: 39
<212> TYPE: PRT
<213> ORGANISM: Mus Sp.

<400> SEQUENCE: 31

Met Met Glu Ala Phe Ser Lys Ser Ala Phe Gln Lys Leu Arg Gln Arg
1               5                   10                  15

Asp Gly Asn Gln Glu Gly Lys Ser Tyr Leu Arg Leu Pro Leu Ser Ile
            20                  25                  30

Leu Phe Leu Asn Lys Glu Ser
        35


<210> SEQ ID NO 32
<211> LENGTH: 41
<212> TYPE: PRT
<213> ORGANISM: Mus Sp.

<400> SEQUENCE: 32

Met Met Glu Ala Phe Ser Lys Ser Ala Phe Gln Lys Leu Arg Gln Arg
1               5                   10                  15
```

-continued

```
Asp Gly Asn Gln Glu Gly Lys Ser Tyr Leu Arg His Leu Ile Pro Arg
            20                  25                  30

Lys Glu Ile Ile Phe Leu Lys Leu Lys
        35                  40


<210> SEQ ID NO 33
<211> LENGTH: 370
<212> TYPE: PRT
<213> ORGANISM: Mus Sp.

<400> SEQUENCE: 33

Met Met Glu Ala Phe Ser Lys Ser Ala Phe Gln Lys Leu Arg Gln Arg
1               5                   10                  15

Asp Gly Asn Gln Glu Gly Lys Ser Tyr Leu Arg Tyr Thr Lys Met Lys
            20                  25                  30

Thr Ala Thr Asn Ile Tyr Ile Phe Asn Leu Ala Leu Ala Asp Ala Leu
        35                  40                  45

Ala Thr Ser Thr Leu Pro Phe Gln Ser Val Asn Tyr Leu Met Gly Thr
    50                  55                  60

Trp Pro Phe Gly Asn Ile Leu Cys Lys Ile Val Ile Ser Ile Asp Tyr
65                  70                  75                  80

Tyr Asn Met Phe Thr Ser Ile Phe Thr Leu Cys Thr Met Ser Val Asp
                85                  90                  95

Arg Tyr Ile Ala Val Cys His Pro Val Lys Ala Leu Asp Phe Arg Thr
            100                 105                 110

Pro Arg Asn Ala Lys Ile Val Asn Val Cys Asn Trp Ile Leu Ser Ser
        115                 120                 125

Ala Ile Gly Leu Pro Val Met Phe Met Ala Thr Thr Lys Tyr Arg Gln
    130                 135                 140

Gly Ser Ile Asp Cys Thr Leu Thr Phe Ser His Pro Thr Trp Tyr Trp
145                 150                 155                 160

Glu Asn Leu Leu Lys Ile Cys Val Phe Ile Phe Ala Phe Ile Met Pro
                165                 170                 175

Val Leu Ile Ile Thr Val Cys Tyr Gly Leu Met Ile Leu Arg Leu Lys
            180                 185                 190

Ser Val Arg Met Leu Ser Gly Ser Lys Glu Lys Asp Arg Asn Leu Arg
        195                 200                 205

Arg Ile Thr Arg Met Val Leu Val Val Val Ala Val Phe Ile Val Cys
    210                 215                 220

Trp Thr Pro Ile His Ile Tyr Val Ile Ile Lys Ala Leu Ile Thr Ile
225                 230                 235                 240

Pro Glu Thr Thr Phe Gln Thr Val Ser Trp His Phe Cys Ile Ala Leu
                245                 250                 255

Gly Tyr Thr Asn Ser Cys Leu Asn Pro Val Leu Tyr Ala Phe Leu Asp
            260                 265                 270

Glu Asn Phe Lys Arg Cys Phe Arg Glu Phe Cys Ile Pro Thr Ser Ser
        275                 280                 285

Thr Ile Glu Gln Gln Asn Ser Ala Arg Ile Arg Gln Asn Thr Arg Glu
    290                 295                 300

His Pro Ser Thr Ala Asn Thr Val Asp Arg Thr Asn His Gln Pro Thr
305                 310                 315                 320

Leu Ala Val Ser Val Ala Gln Ile Phe Thr Gly Tyr Pro Ser Pro Thr
                325                 330                 335

His Val Glu Lys Pro Cys Lys Ser Cys Met Asp Arg Gly Met Arg Asn
            340                 345                 350
```

```
Leu Leu Pro Asp Asp Gly Pro Arg Gln Glu Ser Gly Glu Gly Gln Leu
        355                 360                 365

Gly Arg
    370


<210> SEQ ID NO 34
<211> LENGTH: 325
<212> TYPE: PRT
<213> ORGANISM: Mus Sp.

<400> SEQUENCE: 34

Met Met Glu Ala Phe Ser Lys Ser Ala Phe Gln Lys Leu Arg Gln Arg
1               5                   10                  15

Asp Gly Asn Gln Glu Gly Lys Ser Tyr Leu Arg Tyr Thr Lys Met Lys
            20                  25                  30

Thr Ala Thr Asn Ile Tyr Ile Phe Asn Leu Ala Leu Ala Asp Ala Leu
        35                  40                  45

Ala Thr Ser Thr Leu Pro Phe Gln Ser Val Asn Tyr Leu Met Gly Thr
    50                  55                  60

Trp Pro Phe Gly Asn Ile Leu Cys Lys Ile Val Ile Ser Ile Asp Tyr
65                  70                  75                  80

Tyr Asn Met Phe Thr Ser Ile Phe Thr Leu Cys Thr Met Ser Val Asp
                85                  90                  95

Arg Tyr Ile Ala Val Cys His Pro Val Lys Ala Leu Asp Phe Arg Thr
            100                 105                 110

Pro Arg Asn Ala Lys Ile Val Asn Val Cys Asn Trp Ile Leu Ser Ser
        115                 120                 125

Ala Ile Gly Leu Pro Val Met Phe Met Ala Thr Thr Lys Tyr Arg Gln
    130                 135                 140

Gly Ser Ile Asp Cys Thr Leu Thr Phe Ser His Pro Thr Trp Tyr Trp
145                 150                 155                 160

Glu Asn Leu Leu Lys Ile Cys Val Phe Ile Phe Ala Phe Ile Met Pro
                165                 170                 175

Val Leu Ile Ile Thr Val Cys Tyr Gly Leu Met Ile Leu Arg Leu Lys
            180                 185                 190

Ser Val Arg Met Leu Ser Gly Ser Lys Glu Lys Asp Arg Asn Leu Arg
        195                 200                 205

Arg Ile Thr Arg Met Val Leu Val Val Val Ala Val Phe Ile Val Cys
    210                 215                 220

Trp Thr Pro Ile His Ile Tyr Val Ile Ile Lys Ala Leu Ile Thr Ile
225                 230                 235                 240

Pro Glu Thr Thr Phe Gln Thr Val Ser Trp His Phe Cys Ile Ala Leu
                245                 250                 255

Gly Tyr Thr Asn Ser Cys Leu Asn Pro Val Leu Tyr Ala Phe Leu Asp
            260                 265                 270

Glu Asn Phe Lys Arg Cys Phe Arg Glu Phe Cys Ile Pro Thr Ser Ser
        275                 280                 285

Thr Ile Glu Gln Gln Asn Ser Ala Arg Ile Arg Gln Asn Thr Arg Glu
    290                 295                 300

His Pro Ser Thr Ala Asn Thr Val Asp Arg Thr Asn His Gln Arg Asn
305                 310                 315                 320

Glu Glu Pro Ser Ser
                325
```

-continued

<210> SEQ ID NO 35
<211> LENGTH: 388
<212> TYPE: PRT
<213> ORGANISM: Mus Sp.

<400> SEQUENCE: 35

```
Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Ala Arg Ile Arg Gln
        355                 360                 365

Asn Thr Arg Glu His Pro Ser Thr Ala Asn Thr Val Asp Arg Thr Asn
    370                 375                 380
```

-continued

```
His Gln Cys Val
385


<210> SEQ ID NO 36
<211> LENGTH: 392
<212> TYPE: PRT
<213> ORGANISM: Mus Sp.

<400> SEQUENCE: 36

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Ala Arg Ile Arg Gln
        355                 360                 365
```

```
Asn Thr Arg Glu His Pro Ser Thr Ala Asn Thr Val Asp Arg Thr Asn
    370                 375                 380

His Gln Thr Ser Leu Thr Leu Gln
385                 390


<210> SEQ ID NO 37
<211> LENGTH: 425
<212> TYPE: PRT
<213> ORGANISM: Mus Sp.

<400> SEQUENCE: 37

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
```

```
            340                 345                 350

Pro Thr Ser Ser Thr Ile Glu Gln Gln Asn Ser Ala Arg Ile Arg Gln
        355                 360                 365

Asn Thr Arg Glu His Pro Ser Thr Ala Asn Thr Val Asp Arg Thr Asn
    370                 375                 380

His Gln Ala His Gln Lys Pro Gln Glu Cys Leu Lys Cys Arg Cys Leu
385                 390                 395                 400

Ser Leu Thr Ile Leu Val Ile Cys Leu His Phe Gln His Gln Gln Phe
                405                 410                 415

Phe Ile Met Ile Lys Lys Asn Val Ser
            420                 425


<210> SEQ ID NO 38
<211> LENGTH: 456
<212> TYPE: PRT
<213> ORGANISM: Mus Sp.

<400> SEQUENCE: 38

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285
```

-continued

```
Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Ala Arg Ile Arg Gln
        355                 360                 365

Asn Thr Arg Glu His Pro Ser Thr Ala Asn Thr Val Asp Arg Thr Asn
    370                 375                 380

His Gln Ile Met Lys Phe Glu Ala Ile Tyr Pro Lys Leu Ser Phe Lys
385                 390                 395                 400

Ser Trp Ala Leu Lys Tyr Phe Thr Phe Ile Arg Glu Lys Lys Arg Asn
                405                 410                 415

Thr Lys Ala Gly Ala Leu Pro Pro Leu Pro Thr Cys His Ala Gly Ser
            420                 425                 430

Pro Ser Gln Ala His Arg Gly Val Ala Ala Trp Leu Leu Pro Leu Arg
        435                 440                 445

His Met Gly Pro Ser Tyr Pro Ser
    450                 455


<210> SEQ ID NO 39
<211> LENGTH: 446
<212> TYPE: PRT
<213> ORGANISM: Homo Sapiens

<400> SEQUENCE: 39

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
        35                  40                  45

Arg Thr Asp Leu Gly Gly Arg Asp Ser Leu Cys Pro Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205
```

-continued

```
Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
        355                 360                 365

Arg Gln Asn Thr Arg Asp His Pro Ser Thr Ala Asn Thr Val Asp Arg
    370                 375                 380

Thr Asn His Gln Cys Leu Pro Ile Pro Ser Leu Ser Cys Trp Ala Leu
385                 390                 395                 400

Glu His Gly Cys Leu Val Val Tyr Pro Gly Pro Leu Gln Gly Pro Leu
                405                 410                 415

Val Arg Tyr Asp Leu Pro Ala Ile Leu His Ser Ser Cys Leu Arg Gly
            420                 425                 430

Asn Thr Ala Pro Ser Pro Ser Gly Gly Ala Phe Leu Leu Ser
        435                 440                 445


<210> SEQ ID NO 40
<211> LENGTH: 418
<212> TYPE: PRT
<213> ORGANISM: Homo Sapiens

<400> SEQUENCE: 40

Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
        35                  40                  45

Arg Thr Asp Leu Gly Gly Arg Asp Ser Leu Cys Pro Pro Thr Gly Ser
    50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
```

```
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
        355                 360                 365

Arg Gln Asn Thr Arg Asp His Pro Ser Thr Ala Asn Thr Val Asp Arg
    370                 375                 380

Thr Asn His Gln Pro Pro Leu Ala Val Ser Met Ala Gln Ile Phe Thr
385                 390                 395                 400

Arg Tyr Pro Pro Pro Thr His Arg Glu Lys Thr Cys Asn Asp Tyr Met
                405                 410                 415

Lys Arg


<210> SEQ ID NO 41
<211> LENGTH: 22
<212> TYPE: PRT
<213> ORGANISM: Mus Sp.

<400> SEQUENCE: 41

Met Glu Ala Phe Ser Lys Ser Ala Phe Gln Lys Leu Arg Gln Arg Asp
1               5                   10                  15

Gly Asn Gln Glu Gly Cys
            20


<210> SEQ ID NO 42
<211> LENGTH: 210
<212> TYPE: DNA
<213> ORGANISM: Mus Sp.

<400> SEQUENCE: 42

tttactgtcc ttgagaatgg agaggatcag caaagctggg aagccctcca ggctcatttc     60
```

-continued

```
agagagaata ttccacagag cttgaaggcg cgggatctgg gccgatgatg gaagctttct    120

ctaagtctgc attccaaaag ctcagacaga gagatggaaa tcaagagggg aagagttacc    180

tcaggttggt ttctcttcag actgtagtga                                     210


<210> SEQ ID NO 43
<211> LENGTH: 179
<212> TYPE: DNA
<213> ORGANISM: Mus Sp.

<400> SEQUENCE: 43

aaaatgaaat attgagaggt cagtctcttg caggtcttgt gcaggtgcac tgctgctgtg     60

aattcatgaa gacaacaccc tcccctttag aagacagtgc ttcacaacac tcccaactag    120

cctctggctc tgatgttcac tttgtcccct cttctgaagc aggtatttat tacagtgtc     179


<210> SEQ ID NO 44
<211> LENGTH: 334
<212> TYPE: DNA
<213> ORGANISM: Mus Sp.

<400> SEQUENCE: 44

tccttctctc tcctccctcc ctctagcctc tggatccctc acagcccatg ctccctccct     60

tccactcaga gagtggcgct ttggggatgc taaggatgcg cctccgtgta cttctaaggt    120

gggagggga tacaagcaga ggagaatatc ggacgctcag acgttccatt ctgcctgccg    180

ctcttctctg gttccactag ggcttgtcct tgtaagaaac tgacggagcc tagggcagct    240

gtgagaggaa gaggctgggg cgcctggaac ccgaacactc ttgagtgctc tcagttacag    300

cctaccgagt ccgcagcaag cattcagaac catg                                334


<210> SEQ ID NO 45
<211> LENGTH: 209
<212> TYPE: DNA
<213> ORGANISM: Mus Sp.

<400> SEQUENCE: 45

agtaaacact aatcaaattt tatttcacag acacctcatt ccaaggaagg aaattatctt     60

tttaaaactg aaataactag gcattccaag caatggcggt gagctgataa agactgagag    120

tgtaatgagt cagaaaattg tgttgggttc ccctcttgag tgtgactaat gtcaaaaggt    180

atgcctttga atcactggtc tatctttgc                                      209


<210> SEQ ID NO 46
<211> LENGTH: 170
<212> TYPE: DNA
<213> ORGANISM: Mus Sp.

<400> SEQUENCE: 46

gattggggga tatattcttc atgctttcag gctccctctg tccattcttt tcctgaacaa     60

agagtcatga caactcaaag aatcaactga aaatcaaaat agaaaatggg ctaaggcaac    120

tggtcgacca ccacaaaggt agttcattct ctcaagcctc ttttaccctt               170


<210> SEQ ID NO 47
<211> LENGTH: 19
<212> TYPE: DNA
<213> ORGANISM: Mus Sp.

<400> SEQUENCE: 47

cgccccagcc tcttcctct                                                  19
```

<210> SEQ ID NO 48
<211> LENGTH: 24
<212> TYPE: DNA
<213> ORGANISM: Mus Sp.

<400> SEQUENCE: 48
gacagtcact ggtgcctatg caat 24

<210> SEQ ID NO 49
<211> LENGTH: 24
<212> TYPE: DNA
<213> ORGANISM: Mus Sp.

<400> SEQUENCE: 49
ctcttcccct cttgatttcc atct 24

<210> SEQ ID NO 50
<211> LENGTH: 24
<212> TYPE: DNA
<213> ORGANISM: Mus Sp.

<400> SEQUENCE: 50
gacgatcacg tgtgctcatg acat 24

<210> SEQ ID NO 51
<211> LENGTH: 1373
<212> TYPE: DNA
<213> ORGANISM: Mus Sp.

<400> SEQUENCE: 51
ggaacccgaa cactcttgag tgctctcagt tacagcctac cgagtccgca gcaagcattc 60
agaaccatgg acagcagcgc cggcccaggg aacatcagcg actgctctga cccccttagct 120 cctgcaagtt gctccccagc acctggctcc tggctcaact tgtcccacgt tgatggcaac 180
cagtccgacc catgcggtcc taaccgcacg gggcttggcg ggagccacag cctgtgccct 240
cagaccggca gcccttccat ggtcacagcc atcaccatca tggccctcta ttctatcgtg 300
tgtgtagtgg gcctctttgg aaacttcctg gtcatgtatg tgattgtaag atataccaaa 360
atgaagactg ccaccaacat ctacattttc aaccttgctc tggcagatgc cttagccact 420
agcacgctgc cctttcagag tgttaactac ctgatgggaa cgtggccctt tggaaacatc 480
ctctgcaaga tcgtgatctc aatagactac tacaacatgt tcaccagtat cttcaccctc 540
tgcaccatga gtgtagaccg ctacattgcc gtctgccacc cggtcaaggc cctggatttc 600
cgtacccccc gaaatgccaa aattgtcaat gtctgcaact ggatcctctc ttctgccatt 660
ggtctgcccg taatgttcat ggcaaccaca aaatacaggc aggggtccat agattgcacc 720
ctcacgttct ctcatcccac atggtactgg gagaacctgc tcaaaatctg tgtcttcatc 780
ttcgccttca tcatgccggt cctcatcatc actgtgtgtt atggactgat gatcttacga 840
ctcaagagtg tccgcatgct gtcgggctcc aaagaaaagg acaggaacct gcgcaggatc 900
acccggatgg tgctggtggt cgtggctgta tttattgtct gctggacccc catccacatc 960
tatgtcatca tcaaagcact gatcacgatt ccagaaacca ctttccagac tgtttcctgg 1020
cacttctgca ttgccttggg ttacacaaac agctgcctga acccagttct ttatgcgttc 1080
ctggatgaaa acttcaaacg atgttttaga gagttctgca tcccaacttc ctccacaatc 1140
gaacagcaaa actctgctcg aatccgtcaa aacactaggg aacacccctc cacggctaat 1200

```
acagtggatc gaactaacca ccagccaacc ctggcagtca gcgtggccca gatctttaca   1260

ggatatcctt ctccgactca tgttgaaaaa ccctgcaaga gttgcatgga caggtgagtg   1320

tgacccggac tcaggtgaca aaataaaagg caagttttag ctttttgcac ggc          1373


<210> SEQ ID NO 52
<211> LENGTH: 416
<212> TYPE: PRT
<213> ORGANISM: Mus Sp.

<400> SEQUENCE: 52

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350
```

```
Pro Thr Ser Ser Thr Ile Glu Gln Gln Asn Ser Ala Arg Ile Arg Gln
        355                 360                 365

Asn Thr Arg Glu His Pro Ser Thr Ala Asn Thr Val Asp Arg Thr Asn
    370                 375                 380

His Gln Pro Thr Leu Ala Val Ser Val Ala Gln Ile Phe Thr Gly Tyr
385                 390                 395                 400

Pro Ser Pro Thr His Val Glu Lys Pro Cys Lys Ser Cys Met Asp Arg
                405                 410                 415


<210> SEQ ID NO 53
<211> LENGTH: 50
<212> TYPE: PRT
<213> ORGANISM: Mus Sp.

<400> SEQUENCE: 53

Met Met Glu Ala Phe Ser Lys Ser Ala Phe Gln Lys Leu Arg Gln Arg
1               5                   10                  15

Asp Gly Asn Gln Glu Gly Lys Ser Tyr Leu Arg Tyr Thr Lys Met Lys
            20                  25                  30

Thr Ala Thr Asn His Gln Leu Glu Asn Leu Glu Ala Glu Thr Ala Pro
        35                  40                  45

Leu Pro
    50


<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 54

Gly Gly Gly Gly Ser Gly Gly Gly Gly Ser Gly Gly Gly Gly Ser
  1               5                  10                  15


<210> SEQ ID NO 55
<211> LENGTH: 90
<212> TYPE: PRT
<213> ORGANISM: Mus sp.

<400> SEQUENCE: 55

Met Met Glu Ala Phe Ser Lys Ser Ala Phe Gln Lys Leu Arg Gln Arg
  1               5                  10                  15

Asp Gly Asn Gln Glu Gly Lys Ser Tyr Leu Arg Tyr Thr Lys Met Lys
             20                  25                  30

Thr Ala Thr Asn His Gln Pro Thr Leu Ala Val Ser Val Ala Gln Ile
         35                  40                  45

Phe Thr Gly Tyr Pro Ser Pro Thr His Val Glu Lys Pro Cys Lys Ser
     50                  55                  60

Cys Met Asp Arg Gly Met Arg Asn Leu Leu Pro Asp Asp Gly Pro Arg
 65                  70                  75                  80

Gln Glu Ser Gly Glu Gly Gln Leu Gly Arg
                 85                  90


<210> SEQ ID NO 56
<211> LENGTH: 45
<212> TYPE: PRT
<213> ORGANISM: Mus sp.
```

-continued

```
<400> SEQUENCE: 56

Met Met Glu Ala Phe Ser Lys Ser Ala Phe Gln Lys Leu Arg Gln Arg
  1               5                  10                  15

Asp Gly Asn Gln Glu Gly Lys Ser Tyr Leu Arg Tyr Thr Lys Met Lys
             20                  25                  30

Thr Ala Thr Asn His Gln Arg Asn Glu Glu Pro Ser Ser
         35                  40                  45
```